US007949545B1

(12) United States Patent
Madras et al.

(10) Patent No.: US 7,949,545 B1
(45) Date of Patent: May 24, 2011

(54) METHOD AND APPARATUS FOR PROVIDING A CENTRALIZED MEDICAL RECORD SYSTEM

(75) Inventors: Peter Madras, Newton, MA (US); Ernest Carabillo, Lexington, MA (US)

(73) Assignee: The Medical RecordBank, Inc., Lexington, MA (US)

( * ) Notice: Subject to any disclaimer, the term of this patent is extended or adjusted under 35 U.S.C. 154(b) by 1028 days.

(21) Appl. No.: 11/122,254

(22) Filed: May 3, 2005

Related U.S. Application Data

(60) Provisional application No. 60/567,736, filed on May 3, 2004, provisional application No. 60/645,062, filed on Jan. 18, 2005.

(51) Int. Cl.
*A61B 5/00* (2006.01)
*G06F 19/00* (2006.01)

(52) U.S. Cl. ............ 705/3; 705/2; 705/4; 707/9; 707/10

(58) Field of Classification Search .................. 705/2–4; 707/9, 10
See application file for complete search history.

(56) References Cited

U.S. PATENT DOCUMENTS

| | | | |
|---|---|---|---|
| 5,832,450 A | 11/1998 | Myers et al. ...................... 705/3 |
| 5,876,821 A | 3/1999 | Chapman et al. ............. 428/64.1 |
| 5,974,389 A | 10/1999 | Clark et al. ......................... 705/3 |
| 6,272,468 B1 | 8/2001 | Melrose .............. 705/2 |
| 6,289,316 B1 | 9/2001 | Aghili et al. ...................... 705/3 |
| 6,304,848 B1 | 10/2001 | Singer ............................... 705/3 |
| 6,415,295 B1 | 7/2002 | Feinberg ................... 707/104.1 |
| 6,523,009 B1 | 2/2003 | Wilkins ............................ 705/3 |
| 6,602,469 B1 | 8/2003 | Maus et al. .................. 422/68.1 |
| 6,651,060 B1 * | 11/2003 | Harper et al. ...................... 707/9 |
| 6,684,188 B1 | 1/2004 | Mitchell et al. ................... 705/3 |
| 2001/0039503 A1 | 11/2001 | Chan et al. ........................ 705/2 |
| 2001/0041991 A1 | 11/2001 | Segal et al. ....................... 705/3 |
| 2002/0004727 A1 | 1/2002 | Knaus et al. ...................... 705/3 |
| 2002/0026332 A1 | 2/2002 | Snowden et al. |
| 2002/0029157 A1 * | 3/2002 | Marchosky ....................... 705/3 |
| 2002/0082868 A1 | 6/2002 | Pories et al. ...................... 705/3 |
| 2002/0138306 A1 | 9/2002 | Sabovich ......................... 705/3 |

(Continued)

FOREIGN PATENT DOCUMENTS

DE 19951070 4/2001

(Continued)

OTHER PUBLICATIONS

Whitfield. *The Missing Link Yonline Health Services*; Health Service Journal, pp. 10-11; Sep. 11, 2003.

(Continued)

*Primary Examiner* — Linh Michelle Le
(74) *Attorney, Agent, or Firm* — Sunstein Kann Murphy & Timbers LLP

(57) ABSTRACT

An embodiment of the present invention provides a method of creating and maintaining a centralized medical record system. The method of this embodiment includes establishing, in a computer system, a record associated with a client. (The computer system is in communication with a network to which the client has access and is capable of storing records from a multiplicity of clients having medical information developed at a multiplicity of sources). The method also includes receiving medical data from a source pursuant to a written request by the client to the source for transfer of the medical data to the centralized medical record system. Also the method includes storing and logically associating a representation of the medical data with the record and providing the client with access to the record over the network such that the client may review the representation of the medical data.

28 Claims, 99 Drawing Sheets

U.S. PATENT DOCUMENTS

| | | | |
|---|---|---|---|
| 2003/0028402 A1 | 2/2003 | Ulrich et al. | 705/3 |
| 2003/0115083 A1 | 6/2003 | Masarie, Jr. et al. | 702/2 |
| 2003/0125983 A1 | 7/2003 | Flack et al. | 705/2 |
| 2003/0130872 A1 | 7/2003 | Dvorak et al. | 705/2 |
| 2003/0140044 A1 | 7/2003 | Mok et al. | 707/10 |
| 2003/0144885 A1* | 7/2003 | Sachdev | 705/3 |
| 2003/0158754 A1* | 8/2003 | Elkind | 705/3 |
| 2003/0191671 A1 | 10/2003 | Ulrich et al. | 705/2 |
| 2004/0059603 A1* | 3/2004 | Brown et al. | 705/2 |
| 2004/0078217 A1 | 4/2004 | Bacevice et al. | 705/2 |
| 2004/0078227 A1 | 4/2004 | Morris | 705/2 |
| 2004/0078229 A1 | 4/2004 | Gay et al. | 705/2 |

FOREIGN PATENT DOCUMENTS

| | | |
|---|---|---|
| EP | 0591439 B1 | 10/1897 |
| EP | 0875035 B1 | 12/1907 |
| EP | 0978070 A1 | 12/1910 |
| EP | 1158448 A1 | 11/1915 |
| EP | 1303823 A1 | 5/1919 |
| GB | 2301685 A | 11/1996 |
| GB | 2376109 A | 4/2002 |
| GB | 2386228 A | 10/2003 |
| GB | 2394807 A | 5/2004 |
| GB | 2396933 A | 7/2004 |
| JP | 01125811 | 5/1989 |
| JP | 01142999 | 6/1989 |
| JP | 01143001 | 6/1989 |
| JP | 01155100 | 6/1989 |
| JP | 01184439 | 7/1989 |
| JP | 01297154 | 11/1989 |
| JP | 01306704 | 12/1989 |
| JP | 02015070 | 1/1990 |
| JP | 02056089 | 2/1990 |
| JP | 02056104 | 2/1990 |
| JP | 02073807 | 3/1990 |
| JP | 02117142 | 5/1990 |
| JP | 02117143 | 5/1990 |
| JP | 02140685 | 5/1990 |
| JP | 02153427 | 6/1990 |
| JP | 02189803 | 7/1990 |
| JP | 02259555 | 10/1990 |
| JP | 02269535 | 11/1990 |
| JP | 03016184 | 1/1991 |
| JP | 03036312 | 2/1991 |
| JP | 03070733 | 3/1991 |
| JP | 03076787 | 4/1991 |
| JP | 03076788 | 4/1991 |
| JP | 03085279 | 4/1991 |
| JP | 03132148 | 6/1991 |
| JP | 03186996 | 8/1991 |
| JP | 03186997 | 8/1991 |
| JP | 04005522 | 1/1992 |
| JP | 04021380 | 1/1992 |
| JP | 04029896 | 1/1992 |
| JP | 04038910 | 2/1992 |
| JP | 04054375 | 2/1992 |
| JP | 04062285 | 2/1992 |
| JP | 04086506 | 3/1992 |
| JP | 04094316 | 3/1992 |
| JP | 04094490 | 3/1992 |
| JP | 04133826 | 5/1992 |
| JP | 09274626 | 10/1997 |
| JP | 11353404 | 12/1999 |
| JP | 00200314 | 7/2000 |
| JP | 00285189 | 10/2000 |
| JP | 01338062 | 12/2001 |
| JP | 01344342 | 12/2001 |
| JP | 01344344 | 12/2001 |
| JP | 01344346 | 12/2001 |
| JP | 03337858 | 8/2002 |
| JP | 03337860 | 8/2002 |
| JP | 03345900 | 9/2002 |
| JP | 03345903 | 9/2002 |
| JP | 03108666 | 2/2005 |
| WO | WO 9512857 A1 | 11/1995 |
| WO | WO 96/41275 | 12/1996 |
| WO | WO 96/41288 | 12/1996 |
| WO | WO 9641275 A1 | 12/1996 |
| WO | WO 9641288 A1 | 12/1996 |
| WO | WO 9921114 A1 | 4/1999 |
| WO | WO 9942932 A2 | 8/1999 |
| WO | WO 9942932 A3 | 8/1999 |
| WO | WO 9942933 A1 | 8/1999 |
| WO | WO 9944162 A1 | 9/1999 |
| WO | WO 0014652 A1 | 3/2000 |
| WO | WO 0026823 A1 | 5/2000 |
| WO | WO 0026823 R6 | 5/2000 |
| WO | WO 0029983 A1 | 5/2000 |
| WO | WO 0051028 A1 | 8/2000 |
| WO | WO 0051028 A4 | 8/2000 |
| WO | WO 0013274 A2 | 2/2001 |
| WO | WO 013274 A3 | 2/2001 |
| WO | WO 01/45015 A1 | 6/2001 |
| WO | WO 0140967 A2 | 6/2001 |
| WO | WO 0141037 A2 | 6/2001 |
| WO | WO 0141037 A3 | 6/2001 |
| WO | WO 0141037 R1 | 6/2001 |
| WO | WO 0145015 A1 | 6/2001 |
| WO | WO 0165449 A1 | 9/2001 |
| WO | WO 0167345 A1 | 9/2001 |
| WO | WO 0180117 A1 | 10/2001 |
| WO | WO 0186506 A1 | 11/2001 |
| WO | WO 02/08941 A1 | 1/2002 |
| WO | WO 0203298 A1 | 1/2002 |
| WO | WO 0208941 A1 | 1/2002 |
| WO | WO 0227998 A2 | 4/2002 |
| WO | WO 0227998 A3 | 4/2002 |
| WO | WO 0227998 R5 | 4/2002 |
| WO | WO 0229664 A1 | 4/2002 |
| WO | WO 0237398 A2 | 5/2002 |
| WO | WO 0237398 A3 | 5/2002 |
| WO | WO 0242985 A1 | 5/2002 |
| WO | WO 0242985 R5 | 5/2002 |
| WO | WO 0242985 R7 | 5/2002 |
| WO | WO 02063503 A2 | 8/2002 |
| WO | WO 02063503 A3 | 8/2002 |
| WO | WO 03/025798 A1 | 3/2003 |
| WO | WO 03019422 A1 | 3/2003 |
| WO | WO 03025798 A1 | 3/2003 |
| WO | WO 03030069 A1 | 4/2003 |
| WO | WO 03034294 A2 | 4/2003 |
| WO | WO 03034294 A3 | 4/2003 |
| WO | WO 03040965 A2 | 5/2003 |
| WO | WO 03040965 A3 | 5/2003 |
| WO | WO 03071443 A1 | 8/2003 |
| WO | WO 03085574 A1 | 10/2003 |
| WO | WO 03085577 A1 | 10/2003 |
| WO | WO 2004021213 A2 | 3/2004 |
| WO | WO 2004021213 A3 | 3/2004 |
| WO | WO 2004/044778 A1 | 5/2004 |
| WO | WO 2004042596 A1 | 5/2004 |
| WO | WO 2004044778 A1 | 5/2004 |

OTHER PUBLICATIONS

Cao et al, *Assessing Explicit Error Reporting in the Narrative Electronic Medical Record Using Keyword Searching*; Journal of Biomedical Informatics; vol. 35, No. 1-2, pp. 99-105, Feb.-Apr. 2003.

Bizzell, *Capitol ENT*, Health Management Technology, vol. 24, No. 5, pp. 28, May 2003.

Rogoski, *Having It Your Way Yelectronic Medical Records*, Heath Management Technology, vol. 24, No. 5, pp. 12-14, 16, May 2003.

Zhang et al, *Develop Security Architecture for Both In-House Healthcare Information Systems and Electronic Patient Record*, Proc. SPIE—Int. Soc. Opt. Eng., vol. 5033, pp. 392-402, 2003.

Coyle et al, *Standards for detailed clinical models as the basis for medical data exchange and decision support*, Int. J. Med. Inform (Ireland), vol. 69, No. 2-3, pp. 157-174, Mar. 2003.

Kuzmak et al, *Experience with DICOM for the clinical specialties in the healthcare enterprise*, Proc. SPIE—Int. Soc. Opt. Engl. vol. 5033, pp. 18-29, 2003.

Murff, et al, *Primary care physician attitudes concerning follow-up of abnormal test results and ambulatory decision support systems*, Int. J. Med. Inform. (Ireland), vol. 71, No. 2-3, pp. 137-149, Sep. 2003.

Cimino, et al, *The Patient Clinical Information System (PatCIS): technical solutions for and experience with giving patients access to their electronic medical records*, Int. J. Med. Inform. (Ireland), vol. 68, No. 1-3, pp. 113-127, Dec. 2002.

Hall, et al, *Enabling remote access to personal electronic medical records*, IEEE Eng. Med. Biol, Mag., vol. 22, No. 3, pp. 133-9, May-Jun. 2003.

Preston, et al, *Estimation of radiographic doses in a case-control study of acute myelogenous leukemia*, Health Phys., vol. 84, No. 2, pp. 245-259, Feb. 2003.

Cimino, et al, *What do patients do with access to their medical records?*, Medinfo 2001, vol. 2, pp. 1440-4.

LeDuff, et al, *Sharing medical data for patient path analysis with data mining method*, Medinfo 2001, vol. 2, pp. 1364-8.

*IT outsourcing secures confidentiality*, Health Manage. Technol. (USA), vol. 23, No. 10, pp. 46-48, Nov. 2002.

Doupi, et al, *Structured physical examination data: a modeling challenge*, Medinfo 2001, vol. 1, pp. 614-618.

Johnson, et al, *Achieving reuse of computable guideline systems*, Medinfo 2001, vol. 1, pp. 99-103.

Tschirley, et al, *Patient-oriented segmentation and visualization of medical data*, Proceedings of the Fift IASTED International Conference Computer Graphics and Imaging, pp. 214-9, 2002.

Portoni, et al, *User-oriented views in health are information system*, IEEE Trans. Biomed. Eng. (USA), vol. 49, No. 12, pp. 1387-1398, Dec. 2002.

Mukherji, et al, *Architecture for a large healthcare information system*, IT Prof. (USA), vol. 6, No. 4, pp. 19-27, Nov.-Dec. 2002.

Maskens, *Standards in electronic health care records: the EADG/BACH paradigm*, Electronic Health Records and Communication for Better Health Care, Proceedings for EuroRec '01, pp. 98-101, 2001.

Janczewski, et al, *Development of information security baselines for healthcare information systems in New Zealand*, Comput. Ssecur. (UK), vol. 21, No. 2, pp. 172-192, 2002.

Sostrom, et al, *Reviewing and reforming policy in health enterprise information security*, Proc. SPIE-Int. Soc. Opt. Eng. (USA), vol. 4323, pp. 118-125, 2001.

Ingenerf, et al, *Standardized terminological services enabling semantic interoperability between distributed and heterogeneous systems*, Int. J. Med. Inform. (Ireland), vol. 64, No. 2-3, pp. 223-240, Dec. 2001.

Dionisio, et al, *Individually tailored multimedia physician-patient communication*, Proceedings of the International Conference on Mathematics and Engineering Techniques in Medicine and Biological Sciences. MTMBS'00, vol. 2, pp. 513-519, 2000.

Boxwala, et at, *Toward a representation format for sharable clinical guidelines*, J. Biomed Inf. (USA), vol. 34, No. 3, pp. 157-169, Jun. 2001.

Rogoski, *Integration crossroads Ŷhealth care*, Health Manage. Technol. (USA), vol. 22, No. 10, pp. 14-16, 20, Oct. 2001.

Shah, *Proteus—a model for clinical protocols created from knowledge components*, Proceedings 14$^{th}$ IEEE Symposium on Computer-Based Medical Systems. CBMS, pp. 59-64, 2001.

Giversen, et al, *IT in medical [practice: an exploratory case study in Denmark's publicly financed healthcare system*, Int. J. Healthc. Technol. Manag. (Switzerland), vol. 3, No. 1, pp. 24-47, 2001.

Beird, *How to satisfy both clinical and information technology goals in designing a successful picture archiving and communication system*, J. Digit Imaging (USA), vol. 13, No. 2, pp. 10-12, May 2001.

Warner, *Good isn't enough Ŷnatural language processing in healthcare*, Health Manage. Technol. (USA), vol. 22, No. 6, pp. 30-31, Jun. 2001.

Caccia, et al, *Java DICOM programming interface ((JDPI): a simple tool to manage medical images through the network*, Phys. Med. (Italy), vol. 16, No. 4, pp. 181-6, Oct.-Dec. 2000.

Pallawala, et al, *EMR based telegeriatric system*, Int. J. Med. Inform. (Ireland), vol. 61, No. 2-3, pp. 229-234, May 2001.

Chien-Tsai, et al, *Sharing patient care records over the World Wide Web*, Int. J. Med. Inform. (Ireland), vol. 61, pp. 189-205, May 2001.

Treiber, *The security and patient privacy issues of widespread PACS usage*, From PACS to Internet/Intranet, Information-Systems, Multimedia and Telemedicine, EuroPACS 2000. Proceedings of the 18$^{th}$ International Conference, pp. 307-316, 2000.

Gamberger, et al, *Inconsistency tests for patient records in a coronary heart disease database*.

Alaoui, et al, *Development of a secure medical research environment*, Proceedings 2000 IEEE EMBS International Conference on Information Technology Applications in Biomedicine. ITAB-IT IS 2000. Joint Meeting Third IEEE EMBS International Conference on Information Technology Applications in Biomedicine (ITAB'00). Third Workshop of the International Telemedical Information Society (IT IS'00) (Cat. No. 00$^{th}$8523), pp. 44-49, 2000.

Rowberg, et al, *Developing a framework for worldwide image communication Ŷfor healthcare*, J. Digit. Imaging (USA), vol. 12, No. 2, pp. 189-190, May 1999.

Wymer, *Managing documents and images efficiently Ŷin health care*, Health Manage. Technol. (USA), vol. 21, No. 10, pp. 20-21, Oct. 2000.

Van der Meijden, et al, *An experimental electronic patient record for stroke patients. 2. System description*, Int. J. Med. Inform. (USA), vol. 58-59, pp. 127-140, Sep. 2000.

Kemper, *Losing the paper trail. Electronic records save $3000 a month secure information and save time*, Health Manage. Technol. (USA), vol. 21, No. 7, pp. 50, Jul. 2000.

Kilbridge, *E-healthcare: urging providers to embace the Web*, M.D. Comput. (USA), vol. 17, No. 1, pp. 36-39, Jan.-Feb. 2000.

Gregg, et al, *Imaging vs. electronic medical record at Texas Scottish Rite Hospital for Children*, Toward an Electronic Patient Record'99. Conference and Exposition. TEPR'99, vol. 2, pp. 428-430, 1999.

Oppenheim, *Legal aspects of EPRs: the problem of authentication maintaining security and legal trustworthiness*, Toward and Electronic Patient Record'99. Conference and Exposition. TEPR'99, vol. 2, pp. 302-312, 1999.

Bishop, et al, *FRAMEMED moves to an XML browser system*, Toward and Electronic Patient Record'99. Conference and Exposition. TEPR'99, vol. 1, pp. 737-739, 1999.

*Health Records: Social Needs and Personal Privacy*, Conference Proceedings, Washington DC, Feb. 11-12, 1993, Omni Shoreham Hotel.

NetView: Online Medical Services: The Second Generation; Oct. 20, 2003.

PC World; Oct. 20, 2003.

Search Engine Strategies 2003 Conf & Expo, Oct. 20, 2003.

MRO Medical Records Online: Simple and Effective Medical Record Solutions, Feb. 13, 2004.

Expert describes phases of medical record computerization, Feb. 12, 2004.

Testimony: National Committee on Vital and Health Statistics, Feb. 12, 2004.

The Push for Online Medical Info, Feb. 12, 2004.

The Personal Internetworked Notary and Guardian, International Journal of Medical Informatics.

Medical Records Projects; Feb. 10, 2004.

Pew Internet & American Life, Health Privacy Project, Nov. 26, 2000.

Rapid Responses for Schoenberg and Safran, Feb. 10, 2004.

The Internet Law Journal, TILJcom News Desk Health Care, Feb. 11, 2004.

The Electronic Medical Record: Promises and Threats, Feb. 10, 2004.

WWW and the Electronic Medical Record, Feb. 10, 2004.

IS4ALL highlights electronic health record in second seminar on Universal Access in Health Telematics, Feb. 10, 2004.

2001: A Personal Health Space Odyssey, Feb. 10, 2004.

*Visions of Privacy*: Policy Choices for the Digital Age.

*Health Records: Social Needs and Personal Privacy*, Conference Proceedings, Washington DC, Feb. 11-12, 1993, Omni Shoreham Hotel.

*Net View: Online. Medical Services:* The Second Generation; Oct. 20, 2003.

Kenneth Mandl et al., "Public standards and patients' control: how to keep electronic medical records accessible but private," BMJ, vol. 322, Feb. 3, 2001, pp. 283-287.

\* cited by examiner

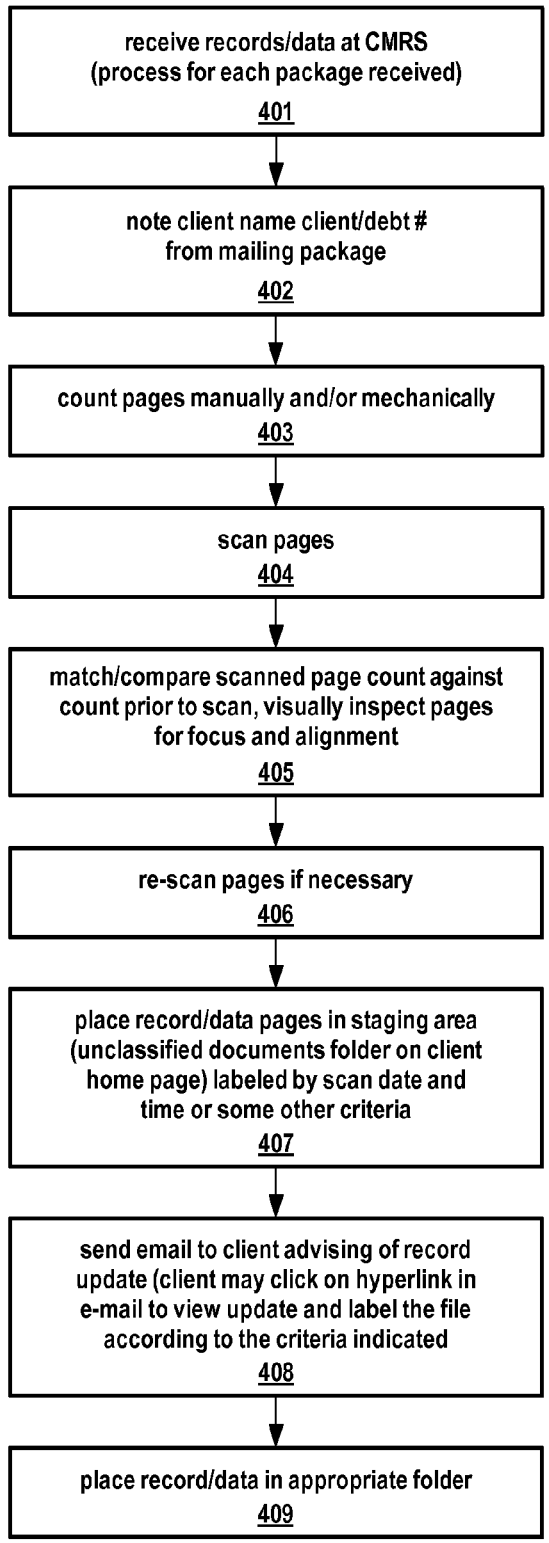
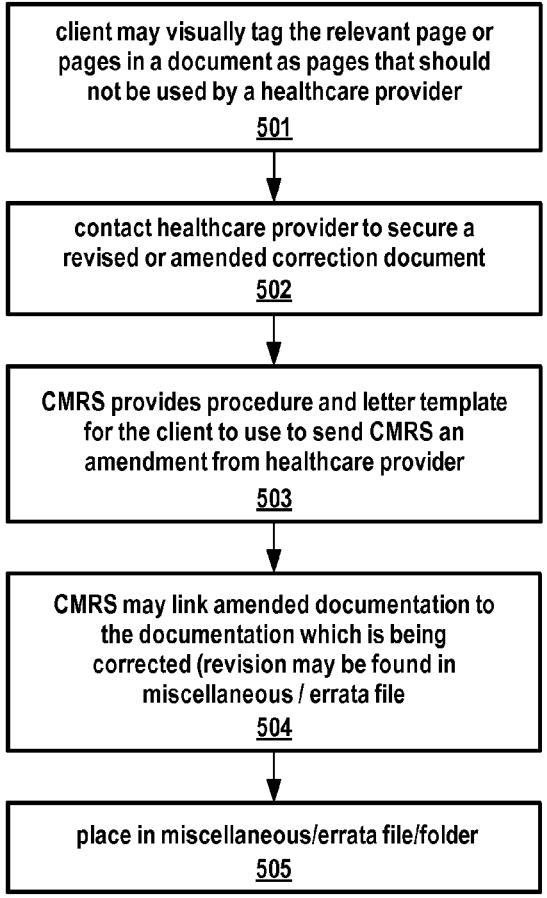
*FIG. 4*   *FIG. 5*

The Medical Record Bank - Microsoft Internet Explorer

File   Edit   View   Favorites   Tools   Help

← Back   →   ⟳   ⌂   🔍   ★ Favorites   ...

http://www.medicalrecordbank.com/followupletter.html

Medical Record Department

[Type the healthcare facility name here]

[First Address Line]

[Second Address Line]

[City]   [St]   [ZIP]

To Whom it may concern,

I requested that a copy of the salient pages in my medical record be sent to me at the following address: c/o The Medical Record Bank, 35 Great Oak Road, Mashpee, MA 02649.

In particular, I request only the History and Physical, The Discharge Summary, the Lab results and any operative report, pathology report or consultations be included. There is no need to included daily progress notes, nurses or daily orders in this request. I recognize that I may be responsible for a copying fee. This may be sent to me at my home address as listed in the chart.

*FIG. 28*

Worldwide Instant Access to your Healthcare Information

| Home | Client Homepage | Logout |

Logged In As: Jane Doe
Master Account

Critical Health Information Summary

Patient Information [EDIT]

DOB: March 22, 1943 • Sex: Female • Weight: 145   Height: 5 feet 7 inches.
Address: 32 Montrose Street, Newton, MA 02458 (E) 123-456-7890
Health Insurance Company name: XYZ Eastern • Policy Number: 12345xyz2

General Health [EDIT]

I am a fairly healthy 62 year old woman on pills for blood pressure and diabetes. I had my gall bladder removed in January of 05, but that's in the past and I'm fine now. I'm currently on a diet to lose 25 pounds

Present Diagnosis [EDIT] [NEW]

O  Diabetes : 2003 • Paul McGregor • No Hospital Treatment • 102 345-6789

O  High Blood Pressure : 1998 • Paul McGregor • No Hospital Treatment • 102 345-

THE MEDICAL RECORD BANK Inc.™

▲ Client Homepage
▲ Account Maintenance
▲ Help

Previous Diagnosis [EDIT] [NEW]

○ Gall Bladder Surgery : 2005 • Nestor Beraltian • Wellington Hospital • 111 222-4444

Precription Medications [EDIT] [NEW] [DEL]

○ Diabeta : 1 pill (5mg), daily

○ Lisinopril : 10 mg, daily

○ HCTZ : 25 mg, daily

Herbal on Non-prescription Medications [EDIT] [NEW] [DEL]

○ Aspirin : 1 pill, Daily

○ Multi-Vitamin : 1 pill, daily

Operations [EDIT] [NEW]

*FIG. 34*

○ Gall Bladder Surgery : 2005 • Nestor Beraltian, Wellington Hospital, 111 222-4444
○ Hysterectomy : 2003, Amanda Robertson, Wellington Hospital, 111 222-3333
Implants 
Allergies 
○ Penicillin
○ Dander
○ Ragweed
Blood 
Type :
Number of Transfusions : 0
Blood donor : No
Accept Blood Transfusion : No
Accepts Blood Projects : No
FIG. 35

General Considerations 

Religious preference : Congregationalist

Organ Donor : No

Physician Contact in Case of Emergency  

○ Surgeon : Nestor Beraltian, 43 Weston Way, Wellington MA • 111 222-4444

○ PCP : Paul Mcgregor, 987 Beauregard Street, Newton MA • 102 345-6789

Emergency Contact   

○ Brother : James Doe, 987 Rutherford Street, Cambridge MA • 123 456-7890

○ Brother : John Doe, 34 Heathdale Street, Wellington MA • 102 345-6789

Special Instructions 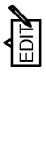

In the event of an emergency, please contact one of my brothers. I have no restrictions in terms of my care, but I do have an advance directive. If I am in danger of death please contact my attorney Ms. Kate at 123-456-7890 for instructions.

*FIG. 36*

Worldwide Instant Access to your Healthcare Information

| Home | Client Homepage | Logout |

Logged In As: Jane Doe
Master Account

Medical Records

THE MEDICAL RECORD BANK Inc. ™

- Client Homepage
- Account Maintenance
- Help

Medical Records

Status : [ Rejected ▶ ]

*Name : [ Hospital Discharge Sur ]

Comment : [ Record of my gall bladd ]

*Doctor : [ Nestor Beraltian : Surgeon ▶ ]

*Date : [ Jan ▶ ] [ 08 ▶ ] [ 2005 ▶ ]

[ << Back ] [ Update >> ]

*shows the required fields

Return To Client Homepage

About Us          Privacy and Security          Contact Us

*FIG. 42*

Worldwide Instant Access to your Healthcare Information

| Home | Client Homepage | Logout |

Logged In As: Jane Doe
Master Account

New Client Questionnaire

In this section, we will guide you through a questionnaire that asks about your medical status. Your answers will be used to create your Critical Health Information Summary. Please have the following information available :

- Get all of your pill bottles and other medications and have them at hand. You will need not only your prescription medications, but your OTC (over the counter) medications such as vitamins and herbal supplements as well.
- If you have a medical implant, your doctors probably gave you some paperwork to go with it. Have them handy.
- Please have names, addresses, telephone numbers for your doctors and hospitals.

You need to be as accurate and descriptive as possible when answering these questions because doctors will rely on this information. If you forget something, skip the question and come back to the questionnaire later. Be very sure to update your summary whenever there is a change in your health, a change in medications, or a change in your treatment. Simply click on the Critical Health Information Summary hyperlink on your homepage and you will see that every section has tools for updating.

As you proceed, you will periodically see this icon: [?] Click it for help in answering a question! Please click the link below to get started!

On to the Questionnaire>>

Return To Setting Up Your Account

FIG. 46

Worldwide Instant Access to your Healthcare Information

| Home | Client Homepage | Logout |

Logged In As: Jane Doe
Master Account

New Client Questionnaire

THE MEDICAL RECORD BANK Inc.™

▸ Client Homepage
▸ Account Maintenance
▸ Help

Patient Information

Health Insurance Company Name: [XYZ Eastern]

Policy Number: [12345xyz2]

Date of Birth: [Mar ▸] [22 ▸] [1943 ▸]

Gender: ○ Male ● Female

Weight: [145]

Height: [5 feet 7 inches]

Preferred Contact Person

Relationship: [Brother]

*FIG. 47*

FIG. 48

Address 1 : 987 Rutherford Street

Address 2 : Apt 405

City : Cambridge

State : Massachusetts ▶

Zip : 02110

*Day Phone : 123 456 - 7890

Evening Phone :

Cell Phone :

<< Back   Continue >>

* shows the required fields.

Return To Setting Up Your Account

About Us     Privacy and Security     Contact Us
Copyright © 2004-2005 The Medical RecordBank Inc.™ All Rights Reserved.  Patent Pending.
PO Box 290, Lexington, MA 02420

Worldwide Instant Access to your Healthcare Information

| Home | Client Homepage | Logout |

Logged In As: Jane Doe
Master Account

New Client Questionnaire

THE MEDICAL RECORD BANK Inc. ™

General Health

- Client Homepage
- Account Maintenance
- Help

I am a fairly healthy 62 year old woman on pills for blood pressure and diabetes. I had my gall bladder removed in January of 05, but that's in the past and I'm fine now. I'm currently on a diet to lose 25 pounds

[<< Back] [Continue >>]

Return To Setting Up Your Account

About Us          Privacy and Security          Contact Us

Worldwide Instant Access to your Healthcare Information

Home | Client Homepage | Logout

Logged In As: Jane Doe
Master Account

New Client Questionnaire

THE MEDICAL RECORD BANK Inc. ™

- Client Homepage
- Account Maintenance
- Help

Primary Care Physician

First Name : Paul
*Last Name : McGregor
Address 1 : 987 Beauregard Street
Address 2 : Suite 202
City : Newton
State : Massachusetts
Zip : 02459
*Phone : 102 345-6789

FIG. 52

FIG. 53

Other Doctors
E-mail : pmcgreg@gmamds.org
Emergency Contact : ⦿ Yes ○ No
Number of Other Doctors : 2 ▼
<< Back   Continue >>
* shows the required fields.
Return To Setting Up Your Account
About Us    Privacy and Security    Contact Us
*FIG. 54*

Worldwide Instant Access to your Healthcare Information

Home | Client Homepage | Logout

Logged In As: Jane Doe
Master Account

New Client Questionnaire

Other Doctors

Other Doctor 1

Type : Gynecologist

First Name : Amanda

*Last Name : Robertson

Address 1 : 43 Weston Way

Address 2 : Suite "D"

City : Wellington

State : Massachusetts

THE MEDICAL RECORD BANK Inc. ™

Account Maintenance

Help

*FIG. 55*

Zip : 02445

*Phone : 111 222-3333

E-mail : amrob@xywdoc.org

Emergency Contact : ○ Yes ● No

Other Doctor 2

Type : Surgeon

First Name : Nestor

*Last Name : Beraltian

Address 1 : 43 Weston Way

Address 2 : Suite "L"

City : Wellington

State : Massachusetts ▶

Zip : 02445

*Phone : 111 222-4444

*FIG. 56*

E-mail : [nerek@xxxdoc.org]

Emergency Contact : ⦿ Yes ○ No

Facilities

Number of Facilities : [0 ▼]

[<< Back] [Continue >>]

* shows the required fields.

Return To Setting Up Your Account

About Us    Privacy and Security    Contact Us
Copyright © 2004-2005 The Medical RecordBank Inc.™ All Rights Reserved. Patent Pending.
PO Box 290, Lexington, MA 02420

*FIG. 57*

FIG. 59

Medication 3

Dose : [1 pill (5 mg)]

Frequency : [daily]

Current Medication : ⊙ Yes ○ No

*Type : [Herbal or Non-prescription ▶]

*Name : [Multi-Vitamin]

Dose : [1 pill]

Frequency : [daily]

Current Medication : ⊙ Yes ○ No

Medication 4

*Type : [Prescription ▶]

*Name : [Lisinopril]

Dose : [10 mg]

Frequency : [daily]

Current Medication : ⊙ Yes ○ No

FIG. 61

Medication 5

*Type : [Prescription ▶]

*Name : [HCTZ]

Dose : [25 mg]

Frequency : [daily]

Current Medication : ⊙ Yes ○ No

[<< Back]  [Continue >>]

* shows the required fields.

Return To Setting Up Your Account

About Us       Privacy and Security       Contact Us

Implants
Facility : | Wellington Hospital, Wellington, MA ▶ |
Number of Implants : | 0 ▶ |
| << Back | Continue >> |
* shows the required fields.
Return To Setting Up Your Account
About Us     Privacy and Security     Contact Us
*FIG. 65*

Worldwide Instant Access to your Healthcare Information

| Home | Client Homepage | | Logout |
|---|---|---|---|
| | | Logged In As: Jane Doe | |
| | | Master Account | |

New Client Questionnaire

THE MEDICAL RECORD BANK Inc.™

General Consideration

If it comes to this, I would like to be an organ donor: ○ Yes ⦿ No

Religious Preference [Congregationalist]

Special Instructions

In the event of an ermency, please contact one of my brothers. I have no restrictions in terms of my care, but I do have an advance directive.

If I am in danger of death please contact my attorney Ms. Kate at 123-456-7890 for instructions.

▶ Client Homepage
▶ Account Maintenance
▶ Help

[<< Back] [Continue >>]

*FIG. 68*

Worldwide Instant Access to your Healthcare Information

| Home | Client Homepage | Logout |

Logged In As: Jane Doe
Master Account

Username and Password Administration and Account Billing Information

Your Billing Information                                    [EDIT]

Status : ACTIVE • Renewal Date • February 12th, 2006
Name : Jane Doe
Address : 32 Montrose Street, Newton, Massachusetts 02548
Fee : 30.00 • Credit Card Number : 4111XXXXXXXX1111 • Expiration : 01/06

Your Passwords                                    [NEW] [EDIT] [DEL]

◉ Master : jdheefe2bb
Total Number of Login : 178 Last Login : May 3rd, 2005 11:37:22

○ Record Reader : jane
Total Number of Login : 4 Last Login : March 10th, 2005 09:52:50

○ Record Reader : janedoc
Total Number of Login : 26 Last Login : March 22nd, 2005 14:00:26

○ Record Reader : Elizabeth

▲ Client Homepage
▲ Account Maintenance
▲ Help

THE MEDICAL RECORD BANK Inc.™

*FIG. 69*

Total Number of Login : 0 Last Login :

O Record Reader : Elizabeth2
Total Number of Login : 0 Last Login :

Return To Account Maintenance

About Us      Privacy and Security      Contact Us
Copyright © 2004-2005 The Medical RecordBank Inc.™ All Rights Reserved. Patent Pending.
PO Box 290, Lexington, MA 02420

Worldwide Instant Access to your Healthcare Information

| Home | Client Homepage | Logout |
|------|-----------------|--------|

Logged In As: Jane Doe
Master Account

Physicians List

| | First Name | Last Name | City | State | Zip | Phone | E-mail | Type | |
|---|---|---|---|---|---|---|---|---|---|
| NEW | | | | | | | | | |
| EDIT | Amanda | Robertson | Wellington | MA | 02445 | 111 222-3333 | amrob@xywdoc.org | Gynecologist | DEL |
| EDIT | Nestor | Berallian | Wellington | MA | 02445 | 111 222-4444 | nerek@xxxdoc.org | Surgeon | DEL |
| EDIT | Paul | McGregor | Newton | MA | 02459 | 102 345-6789 | pmcgreg@gmamds.org | PCP | DEL |

- Client Homepage
- Account Maintenance
- Help

THE MEDICAL RECORD BANK Inc.™

Return To Account Maintenance

About Us     Privacy and Security     Contact Us

Day Phone :

Alternative Phone :

E-mail :

Is your PCP? ○ Yes ◉ No

Add as Emergency Contact : ◉ Yes ○ No

<< Back | Continue >>

* shows the required fields.

Return To Account Maintenance

About Us     Privacy and Security     Contact Us

Worldwide Instant Access to your Healthcare Information

Home | Client Homepage | Logout

Logged In As: Jane Doe
Master Account

THE MEDICAL RECORD BANK Inc.™

Client Homepage
Account Maintenance
Help

Edit Physician

Physicians List

Type : Gynecologist
*First Name : Amanda
Middle Name :
*Last Name : Robertson
Address 1 : 43 Weston Way
Address 2 : Suite "D"
City : Wellington
State : Massachusetts
Zip : 02445

*FIG. 76*

Day Phone : 111 222-3333

E-mail : amrob@xywdoc.org

Is your PCP? ○ Yes ● No

Add as Emergency Contact : ○ Yes ● No

<< Back   Continue >>

* shows the required fields.

Return To Account Maintenance

About Us   Privacy and Security   Contact Us

Jane Doe
C/O The Medical Record Bank, Account ID jdheefe2bb
PO Box 290, Lexington, MA 02420

Nestor Beraltian
43 Weston Way
Suite "L"
Wellington, MA 02445

May 03, 2005

RE: REQUEST FOR MEDICAL RECORDS

Dear Dr.Beraltian

I am working with the Medical Record Bank to create and maintain my own comprehensive and readily available medical record. Accordingly, I am requesting the following information today:

___Past Medical Records

___Medical Records for my most recent visit

___A specific part of my record_____

I am interested in receiving only information that would be of use to any physician who may need to treat me in the future. Hence, I am asking only for the salient features of my record such as a recent H&P, lab tests, imaging and EKG studies, consultations from other specialists, recent notes, etc. If my file is 50 pages or less, please feel free to copy the entire file if that is easier for you. Please send the requested information to me at the following address: NOTE: PLEASE TAKE CARE TO USE THE ENTIRE ADDRESS INDICATED BELOW, INCLUDING THE ACCOUNT ID!

Jane Doe
C/O The Medical Record Bank
ACCOUNT ID jdheefe2bb
PO BOX 290, Lexington, MA 02420

Nothing you submit to me will be altered in any way. The information will be scanned, and I will have access to it whenever I need it. Access to the record will be strictly under my control, but I will be pleased to make it available to you if it will assist in my care. Working with the Medical Record Bank, my goal is to ensure that any of my doctors has access to my complete records if and when needed, even in an emergency. This will presumably be of assistance to my physicians while improving the efficiency of the limited time we spend together. If you wish, you can learn more about the Medical Record Bank by visiting www.medicalrecordbank.com. Please let me know if there will be a charge for the copying service.

With sincere appreciation,

_____
Jane Doe

*FIG. 83*

Worldwide Instant Access to your Healthcare Information

| Home | Client Homepage | Logout |

Logged In As: Jane Doe
Master Account

Emergency Card Maintenance

Replacement E-Card Order
Details

New Emergency Cards $10

Leave current card active : ○ Yes ○ No

Your personal data

Salutation : ○ Mr., ⦿ Ms., ○ Mrs., ○ Doctor

*First Name : [Jane]

Middle Name : [Patricia]

*Last Name : [Doe]

Jr., Sr., II, III etc. : [ ]

Date of Birth : [Dec ▶] [31 ▶] [1969 ▶]

- ▲ Client Homepage
- ▲ Account Maintenance
- ▲ Help

THE MEDICAL RECORD BANK Inc. ™

*FIG. 87*

Gender : ○ Male ● Female

*Email : [janedoe@yahoo.com]

Your Billing Information

*Address 1 : [123 Montrose Street]

Address 2 : [　　　　　]

*City : [Newton]

*State : [Massachusetts ▼]

*Zip : [02458]

Country : [United States]

Day Phone : [123-456-7890]

Evening Phone : [123-456-7890]

Your Mailing Information

Same as billing : ☑

*Address 1 : [123 Montrose Street]

Address 2 : [　　　　　]

*FIG. 88*

METHOD AND APPARATUS FOR PROVIDING A CENTRALIZED MEDICAL RECORD SYSTEM

The present application claims priority from U.S. Provisional Application No. 60/567,736, filed May 3, 2004, and U.S. Provisional Application No. 60/645,062, filed Jan. 18, 2005. Both of the above referenced applications are hereby incorporated herein, in their entirety, by reference.

TECHNICAL FIELD

The present invention relates to medical record keeping and, more particularly, to a method and apparatus for providing a centralized medical record system.

BACKGROUND ART

It is know that typically a healthcare facility, such as a doctor's office, clinic or hospital, collects medical data related to each particular subject or patient that is treated at the facility. Such medical data is usually stored at the facility as a medical record for the particular patient. If the patient or subject is treated at more than one medical facility, a number of medical records may exist with respect to the patient. If a first healthcare facility involved in treating the patient requires the patient's medical data or records associated with treatment the patient received at second healthcare facility, the patient must request that medical data or records kept at the second facility be sent to the first facility. Such a process for is time consuming and costly. Further, the patient has little knowledge or control over what one healthcare facility sends another.

SUMMARY OF THE INVENTION

An embodiment of the present invention provides a method of creating and maintaining a centralized medical record system. The method of this embodiment includes establishing, in a computer system, a record associated with a client. (The computer system is in communication with a network to which the client has access and is capable of storing records from a multiplicity of clients having medical information developed at a multiplicity of sources). The method also includes receiving medical data from a source pursuant to a written request by the client to the source for transfer of the medical data to the centralized medical record system. Also the method includes storing and logically associating a representation of the medical data with the record and providing the client with access to the record over the network such that the client may review the representation of the medical data.

In accordance with a related embodiment, the receiving medical data from a source may include receiving medical data from a health care entity which may be a physician, a clinic or a hospital. In accordance with another related embodiment, providing the client with access to the record over the network may include providing the client with access to the record via the Internet and providing the client with access to the record via the Internet may include providing the client with access to the record via a web page.

In accordance with a further related embodiment, the method may also include providing the client with access to a letter template for generating a letter to request medical data from a source. The letter template may cause the letter to be imprinted with a machine readable code identifying at least the client. The code may in addition, or in the alternative, identify the source of the medical data.

In accordance with other related embodiments, the method may include providing the client with an interface that enables the client to accept or reject the association of the medical data with the record and/or providing the client with access over the network such that the client may make a notation on the record with respect to the medical data. The notation may include a date associated with the medical data, a name of a health care entity associated with the medical data and/or the client's comments regarding the medical data.

In accordance with yet further related embodiments, providing the client with access to the record over the network includes providing the client with at least one set of passwords and the client may restrict access to the record as provided by one or more of the set of passwords. Providing the client access to the record may also include permitting another party to obtain access to the record via a password previously forwarded to the client so that the client may grant access to the record by communicating the password to the other party. The other party may have been identified by the client as being in a category of authorized parties.

In yet another related embodiment, the method may also include providing the client with an interface that enables the client to activate one or more emergency cards.

BRIEF DESCRIPTION OF THE DRAWINGS

The foregoing features of the invention will be more readily understood by reference to the following detailed description, taken with reference to the accompanying drawings, in which:

FIG. 4 is a flow diagram illustrating a process by which medical records are included in the centralized medical history in accordance with the embodiment of FIG. 1;

FIG. 5 is a flow diagram illustrating a process by which medical records are edited in accordance with the embodiment of FIG. 1;

FIGS. 25-28 are illustrations of web pages whereby the user may view form letters in accordance with the embodiment of FIG. 24;

FIGS. 33-36 are illustrations of a web page for providing a critical health information summary in accordance with the embodiment of FIG. 30;

FIGS. 40-42 are illustrations of web pages whereby a client may edit a notation to, label of or comment on medical data and review, accept or reject a medical record or data in accordance with the embodiment of FIG. 30;

FIGS. 46-68 are illustrations of web pages for providing a client questionnaire in accordance with the embodiment of FIG. 30;

FIGS. 69-70 are illustrations of a web page for creating and maintaining one or more user name and password sets in accordance with the embodiment of FIG. 30;

FIG. 73 is an illustration of a web page for creating and maintaining a physician list in accordance with the embodiment of FIG. 30;

FIGS. 74-75 is an illustration of web page for adding a physician to the physician list in accordance with the embodiment of FIG. 30;

FIGS. 76-77 is an illustration of a web page for editing physician information in accordance with the embodiment of FIG. 30;

FIG. 83 is an illustration of a medical record request letter in accordance with the embodiment of FIG. 30;

FIGS. 85-89 are an illustration of web pages whereby a client may maintain, order, activate and de-activate an emergency access card in accordance with the embodiment of FIG. 30;

DETAILED DESCRIPTION OF SPECIFIC EMBODIMENTS

Embodiments of the present invention provide a consumer-centric, client controlled process and system that provides a client with a tool that enables the client to manage the creation, acquisition, updating, retrieval and deletion of medical information and healthcare records in a centralized medical record system. Embodiments of the invention enable the client to initiate and approve of information and medical data as well as control access to the medical data.

Figure 1:
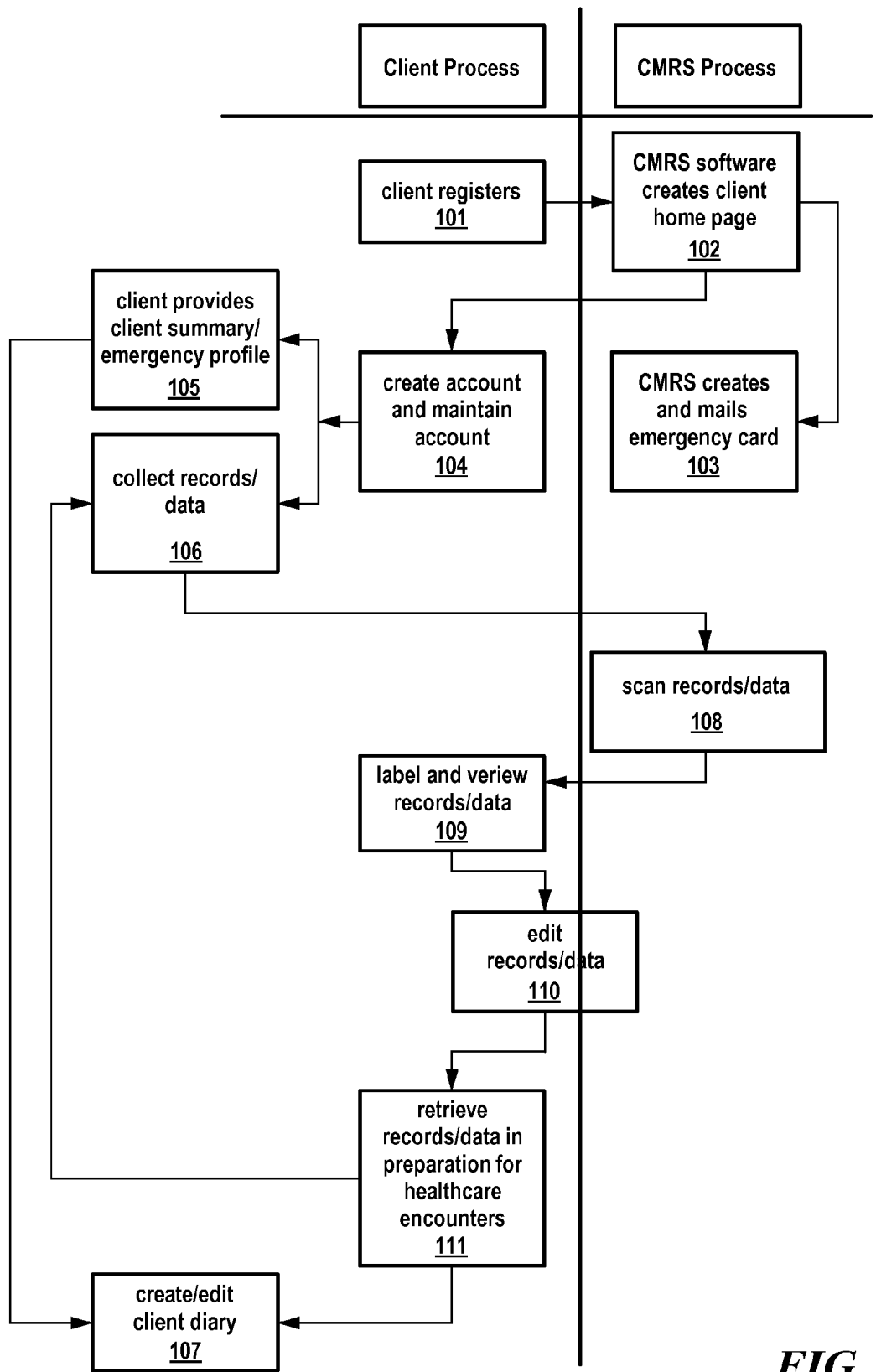
FIG. 1 is a flow diagram illustrating a method for providing a centralized medical history over a network in accordance with an embodiment of the invention.

FIG. 1 is a flow diagram illustrating a method for providing a centralized medical history over a network in accordance with an embodiment of the invention. In accordance with process 101, a client registers with a centralized medical record system service provider (the "CMRS" service provider). Note that the "CMRS service provider" and the "CMRS" are used somewhat interchangeably herein, since it will be appreciated that various tasks can be prepared, or caused to be prepared, automatically or manually in accordance with the business goals and system design constraints.

Figure 10:
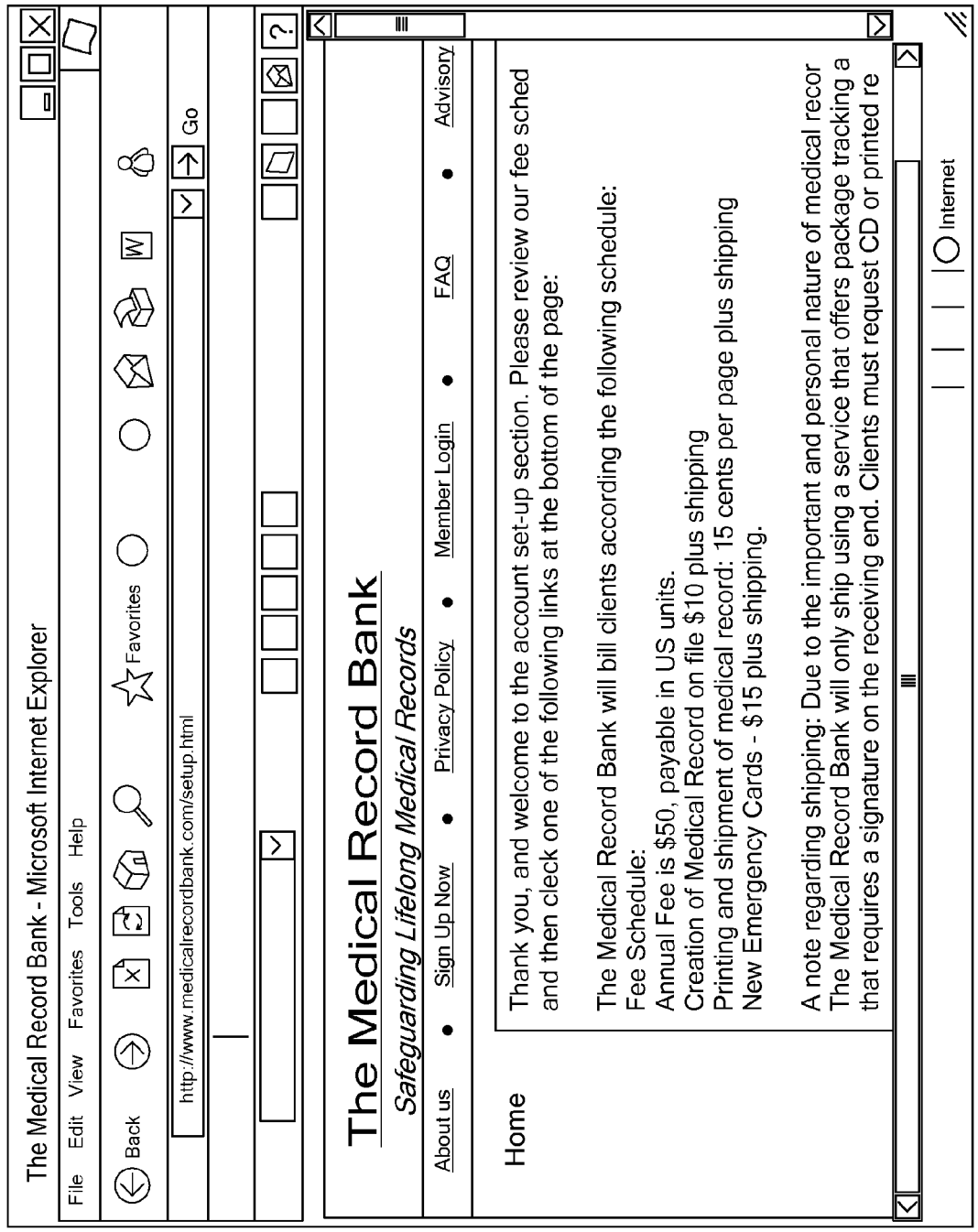
Figure 11:
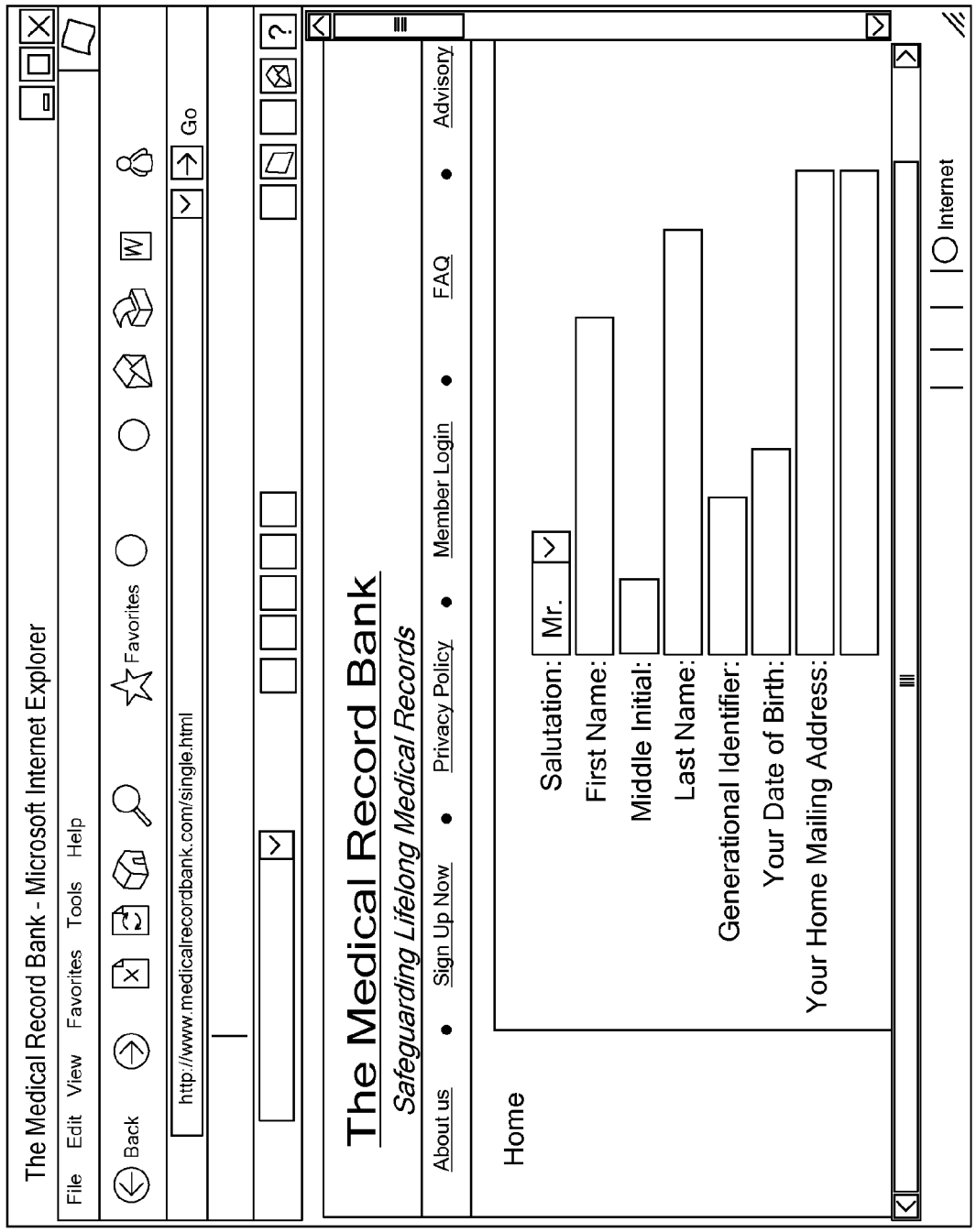

In accordance with this embodiment, the client registers over a computer network and the computer network may be a local area network or a wide area network. For example, in one embodiment of the invention, the wide area network is the Internet. The client may register via one or more graphical user interface, such as the graphical user interface shown in FIGS. 9-11. The graphical user interface may be a series of web pages associated with a website of the CMRS service provider such as the web page illustrated in FIG. 8. In accordance with the embodiment of FIG. 8, a client may click on the "Sign Up Now" hyperlink 801 and the centralized medical history service provider may provide one or more web pages whereby the client may create a centralized medical history account over the network.

Figure 2:
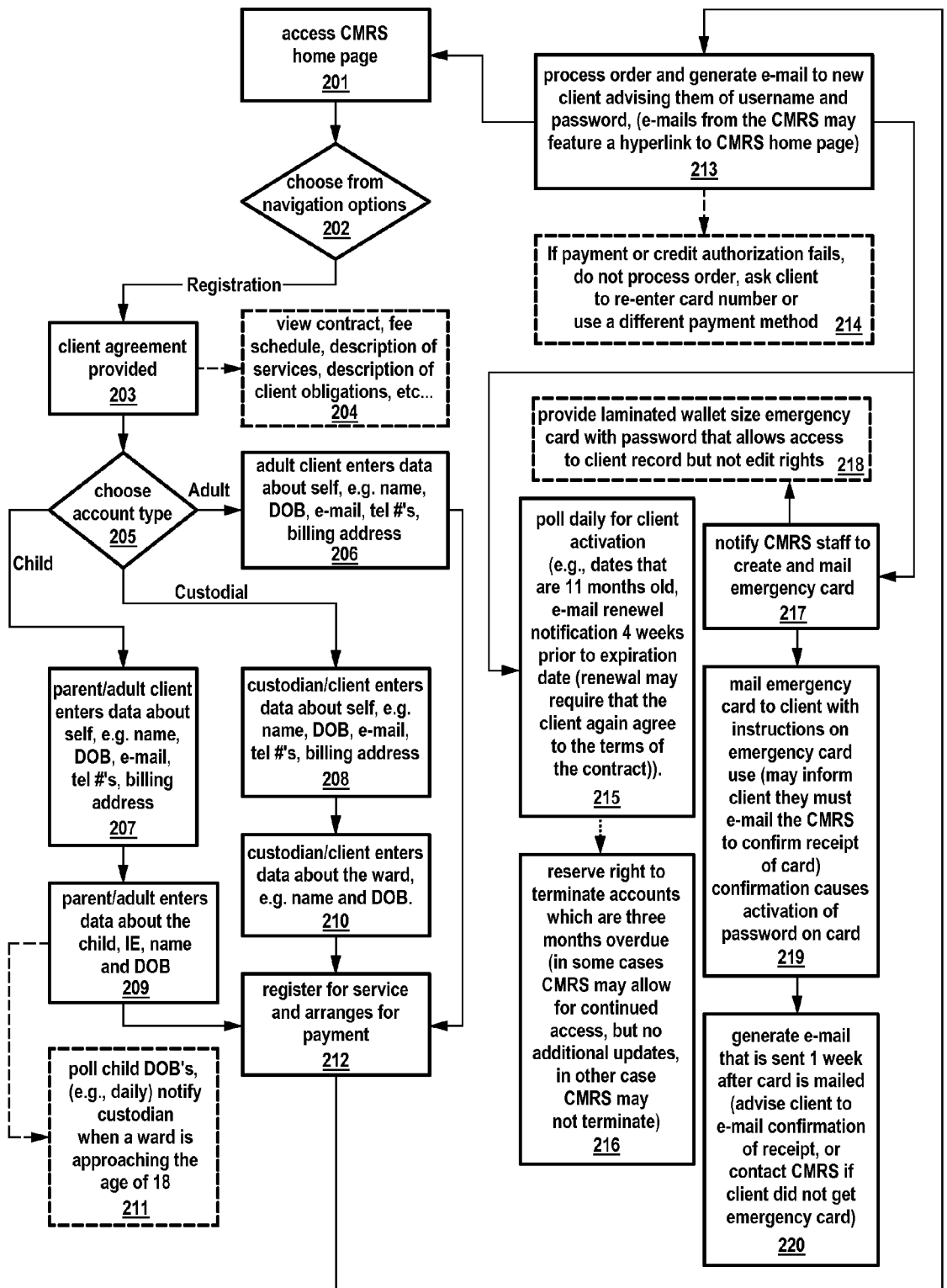
FIG. 2 is a flow diagram illustrating a registration process in accordance with the embodiment of FIG. 1.
Figure 8:
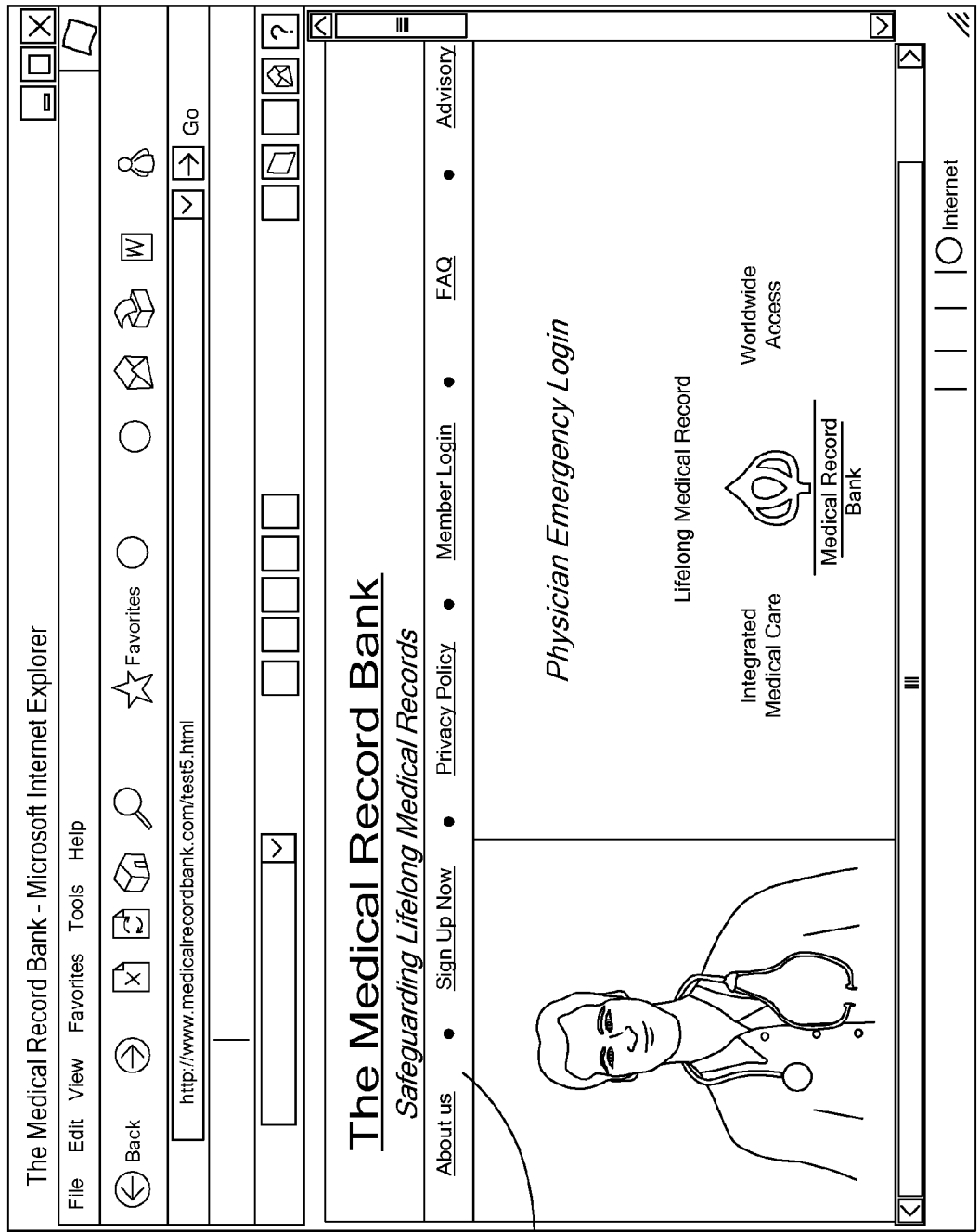
FIG. 8 is an illustration of a web page for providing a centralized medical history in accordance with another embodiment of the invention.
Figure 9:
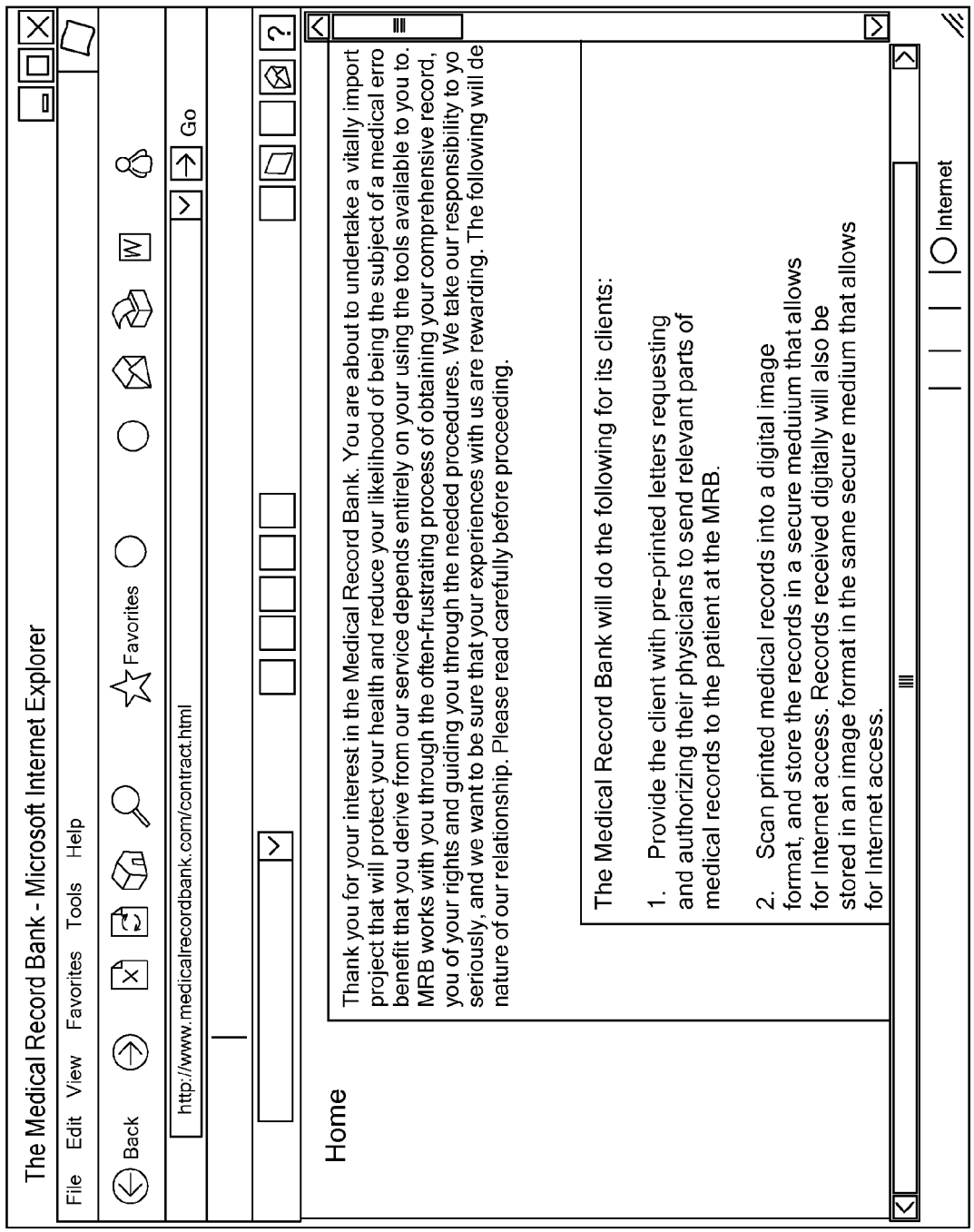
FIGS. 9-11 are illustrations of web pages whereby a client may create an account for a centralized medical history in accordance with the embodiment of FIG. 8.

FIG. 2 is a flow diagram illustrating a registration process which may be performed in accordance with the embodiment of FIGS. 1 and 8. The client accesses the home page of the CMRS service provider in process 201. In process 202, the client chooses from navigation options provided by the CMRS (such as the "Sign Up Now" hyperlink 801 discussed above). If the client chooses the hyperlink 801, the client may then navigate, via hyperlinks, to another web page, as shown in FIG. 9, whereby the client is provided with general information regarding how the CMRS service works. The client may then be provided, in process 203 with one or more web pages (such as that illustrated in FIG. 10) whereby the client may view a client agreement. In accordance with the client agreement, the client may view, in process 204, among other things, a contract, fee schedule, descriptions of the services provided by the CMRS service provider and descriptions of client obligations. The client may submit pertinent information about himself or herself via another web page, such as the web page shown in FIG. 11. If the client agrees to the terms of the client agreement, the client will required, in process 205, to choose an account type. For example, if the client is an adult and the account she wishes to create is for herself, the client will click on a hyperlink which will lead her to an user interface where, in process 206, she will enter data about herself such as her name, date of birth, email address, telephone numbers, billing address, credit card number, etc. If the client is a parent, she may wish to open an account for her child. In this case, she will click on a hyperlink that designates her as a parent/adult client and she will use one or more interfaces similar to that shown in FIG. 11 to enter, in process 207, data about herself and, in process 209, data about her child, including the child's name, date of birth, etc. If the client is a custodian, she may wish to open an account for her ward. In this case, she will click on a hyperlink that designates her as a custodian client and she will use one or more interfaces similar to that shown in FIG. 11 to enter, in process 208, data about herself and, in process 210, data about her ward, including the ward's name, date of birth, etc. Note that the CMRS service provider may poll, in process 211, the dates of birth of parent/child and guardian/child and automatically notify the parent or guardian when a child is approaching the age of 18. Note also that an adult may establish several different types of accounts (one for herself, one for her child, one for her ward) if she so desires. (Alternatively, account types may include an adult account and a custodial account and a parent may set up an account for his or her child as a custodian.) Upon selecting the type of account (or accounts) she wishes to establish, the client will be submit the information she has provided and arrange for payment methods in process 212.

The CMRS service provider processes the account order and generates an email to the client advising them of the username and primary password in process 213. All emails to the client from the CMRS may feature a hyperlink to a CMRS web page. If payment authorization fails, the order will not be processed and the client will be asked to re-enter payment information as shown in process 214. For example, if the client has chosen to pay for the service using a credit card and credit card authorization fails, the order will not be processed and the client will be asked to re-enter the credit card number or the enter another credit card number. The CMRS service provider may poll, in process 215, existing system accounts daily to find client activation dates that indicate that the account is about to expire. In this example an account will last 12 months, thus the CMRS service provider will poll the system for client accounts that are 11 months old. For those accounts that are 11 months old, the CMRS service provider may send a renewal notification some time prior to the expiration date, here four weeks, so that a client may renew his or her account. In accordance with this embodiment, renewal will require the client to again agree to the terms of the client agreement. The CMRS may reserve the right to terminate, in process 216, client accounts that are a predetermined amount of time overdue (here three months). In some cases, the CMRS service provider may permit continued access to the account without permitting additional updates of the account. In other cases, the CMRS service provider may not terminate the account.

Figure 12:
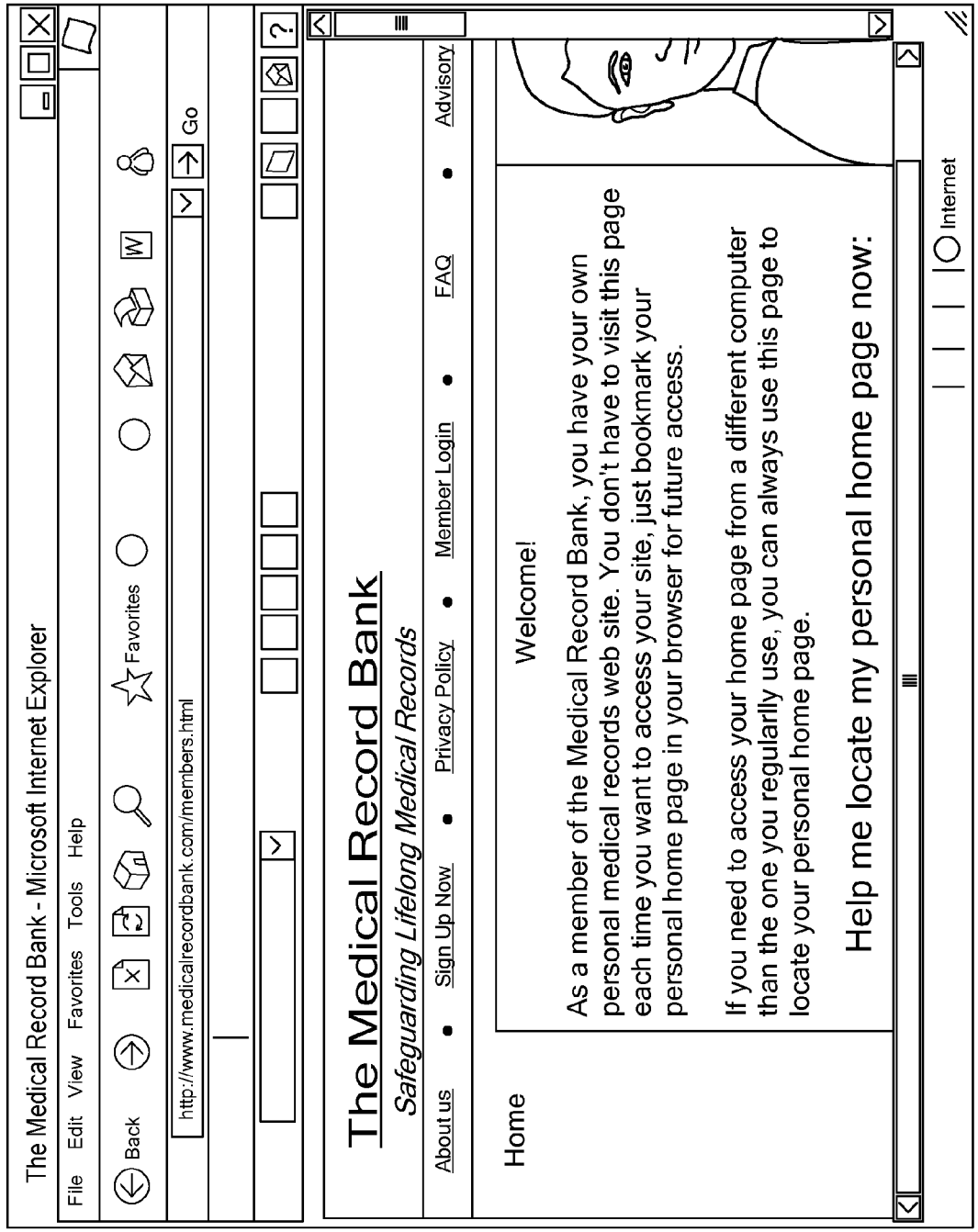
FIGS. 12-15 are illustrations of web pages whereby the user may access a medical history in accordance with the embodiment of FIG. 8.
Figure 13:
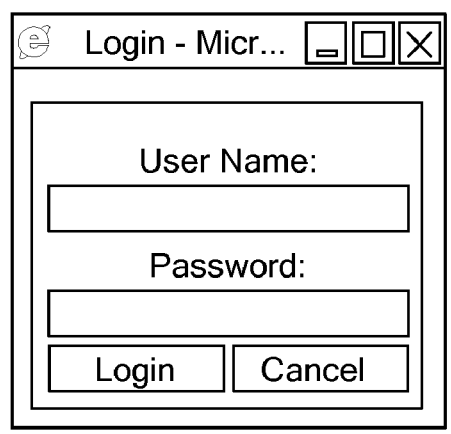
Figure 14:
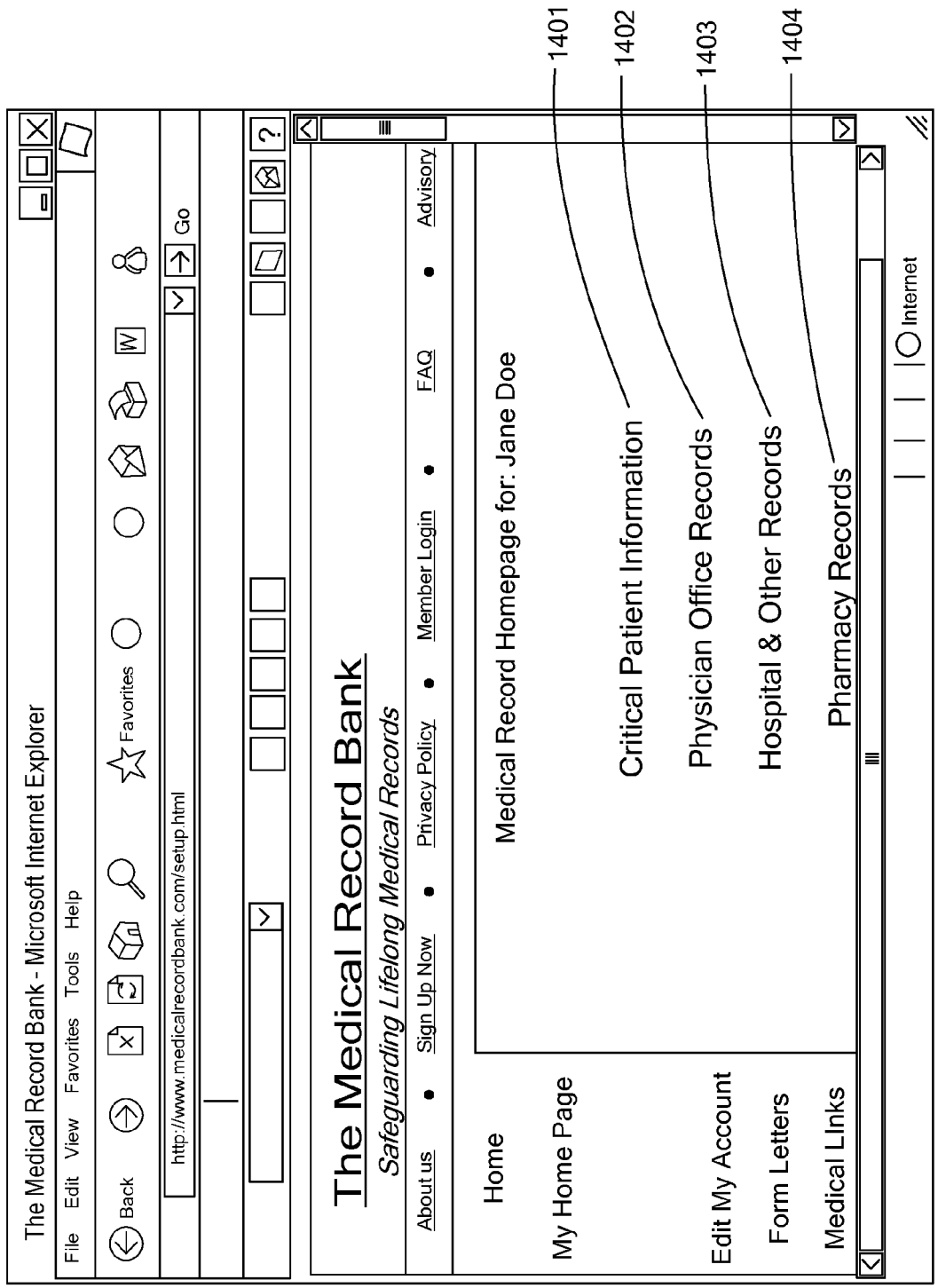

Turning again to FIG. 1, the CMRS service provider creates, in process 102, a "home page" for the client whereby the client may access his or her medical history. FIGS. 12-13 are illustrations of web pages whereby the user may access a medical history and FIG. 14 is an illustration of such a home page (the "client home page") customized for a client for purposes of medical history access. The CMRS service provider also creates and mails, in process 103 of FIG. 1 an emergency card to the client. In accordance with the embodiment of FIG. 2, the CMRS staff is notified, in process 217, that an emergency card should be created and mailed to the client. The CMRS service provider provides, in process 218, an emergency card may be a wallet sized card that features a secondary CMRS generated password that permits access to the client's record in case of a medical emergency but does not allow the user edit the record. In a medical emergency, when an adult or child client is away from loved ones, the emergency access card will give care givers access to all the information they need to treat the patient, and reach next of kin. The emergency card is mailed to the client, in process 219 with instructions associated with emergency card use. The client is also asked to email the CMRS service provider to confirm that the client has received his or her emergency card. Confirmation of receipt of the emergency card will cause the secondary password associated with the card to be activated in the CMRS system. The CMRS may also generate, in process 220, an email a predetermined amount of time after mailing out the emergency card, such a one week later, advising the client to confirm receipt of his or her emergency card or to contact the CMRS service provider if the card was not received. If a client loses his or her emergency care, the CMRS service provider may, upon notification of the loss. The CMRS service provided the replacement card at no cost to the client or for a fee.

The CMRS service provider creates and maintains account for the client in process 104. In accordance with account maintenance, the client provides, in process 105, a client summary and emergency profile. As will be explained in more detail below, in accordance with one embodiment of the invention, each client answers a series of questions online, and a client health summary is generated. The summary delivers critical information about the patient in a concise format, and it can be updated at any time. The summary includes patient demographics such as name, address, age, occupation, etc. The summary also includes a patient health status, including information about medical allergies, prescription drugs, medical implants, and diagnosis, etc. The summary also includes contact information, including physician names and contact information, next or kin/emergency contact information, authority to contact for advance directive or living will, etc. The summary further includes patient comments. Patients can write a note to emergency care providers advising them of any issue or concern not addressed through our automated question system.

The client may begin collecting medical records and data in process 106. The client may also create or edit a client diary in process 107. The client diary accommodates any type of information that the client wises to record, and automatically dates the entries. The diary can be updated at any time. In accordance with one embodiment, a client may create or edit one or more disease-specific diaries to follow the progression of any particular illness or condition.

Figure 3:
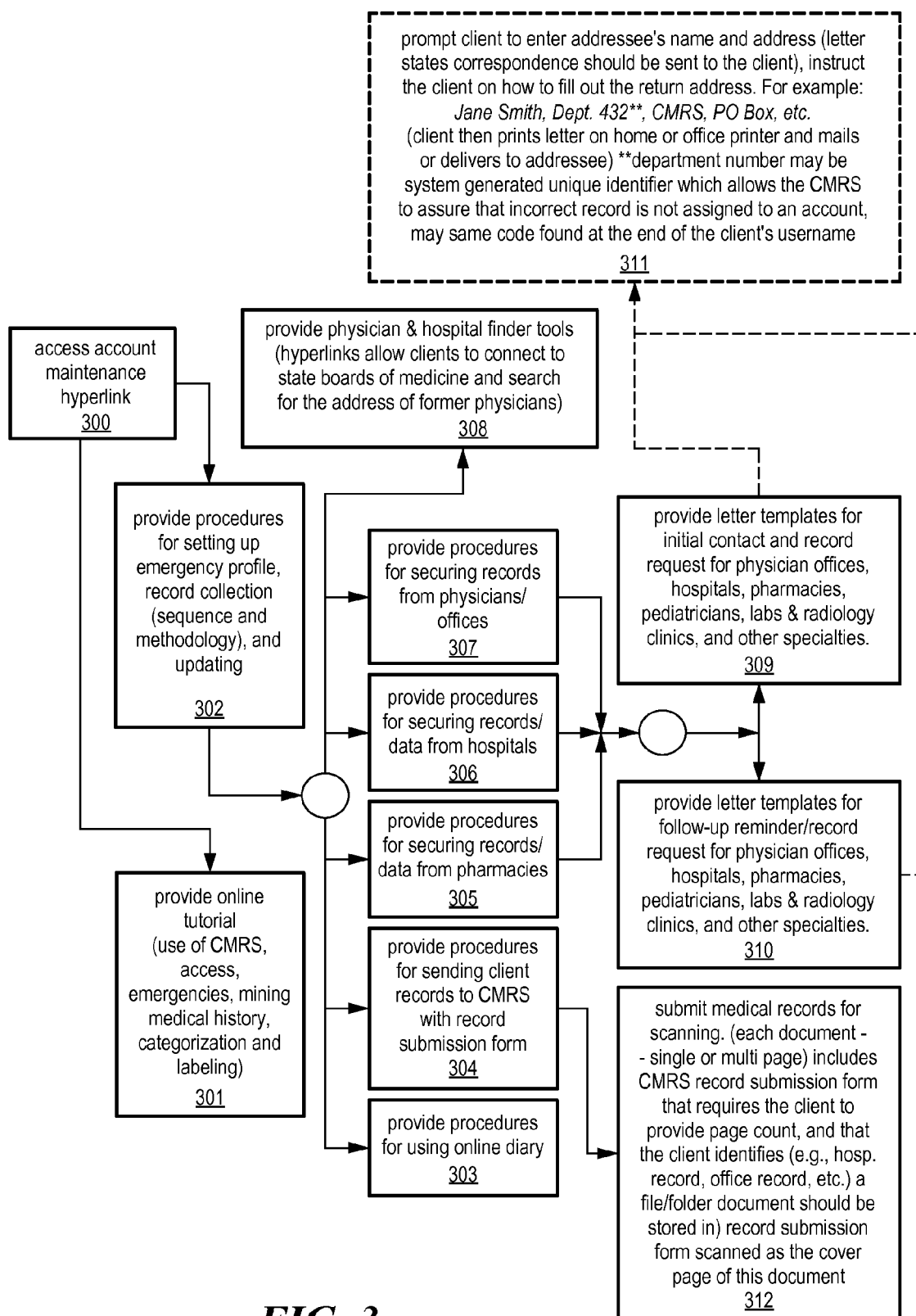
FIG. 3 is a flow diagram illustrating a process by which medical records are collected and a medical history is maintained in accordance with the embodiment of FIG. 1.

FIG. 3 is a flow diagram illustrating a process by which a client account is created, medical records are collected and a medical history is maintained. The client accesses, in process 300, an account maintenance hyperlink provided on an appropriate web page, an on-line tutorial will be provided to the client in process 301. The on-line tutorial may include instructions related to use of the CMRS system, access to the CMRS system, information regarding medical emergencies, information regarding mining or searching a medical history, and information on categorizing and labeling medical data. Via the maintenance hyperlink, procedures for setting up an emergency profile, collecting medical records and data and updating medical records and data (such records and data may include, but are not limited to a paper document or an electronic version of a paper document or other data, for example. pdf or .ehr documents) will be provided in process 302. Further, if a physician or healthcare facility or entity keeps electronic versions of its patient records, the client may request that the physician or healthcare facility or entity transfer the electronic record to the CMRS service provider. The CMRS service provider may create web-page views of electronic records in whatever format they are provided.

Procedures that may be provided to the client may include procedures for using an online medical diary (process 303) (or a disease-specific online diary) and procedures for sending client medical records and data to the CMRS service provider (process 304). For example, clients may submit, in process 312, any medical records or data that the client has collected for scanning by the CMRS service provider. In accordance with this embodiment, to submit such data in the form of one or more page documents, the document may be accompanied by a CMRS record submission form. The form may require the client to provide a page count and identification of a file (such as hospital record, physician office record, etc.) that the client wants the document to be stored in. The record submission form may also be scanned as a cover page of the document.

Other procedures that may be provided to the client include procedures for securing records and data from pharmacies (process 305), procedures for securing records and data from hospitals (process 306), and/or procedures for securing medical records and data from physicians' offices (process 307). Hyperlinks may be provided, in process 308, that permit the client to contact state medical boards and search for information related to physicians (such as a client's former physician's address). The CMRS service provider may also provide, in process 309, letter templates for the client to use to initially request a physician, hospital, pharmacy, laboratory or clinic to forward medical data to the CMRS service provider. Similarly, the CMRS service provider may provide, in process 310, letter templates that a client may use to request that follow-up medical data be forwarded to the CMRS service provider or to remind a physician, hospital, pharmacy, laboratory or clinic to forward records to the CMRS service provider. A letter template may cause the letter to be imprinted with a machine readable code identifying at least the client. The code may in addition, or in the alternative, identify the source of the medical data. Such letter templates may include code which may be scanned, such as bar code, which identifies the client, the health care entity, the letter, the purpose of the letter, the contents of the letter or other information associated with the letter.

Figure 24:
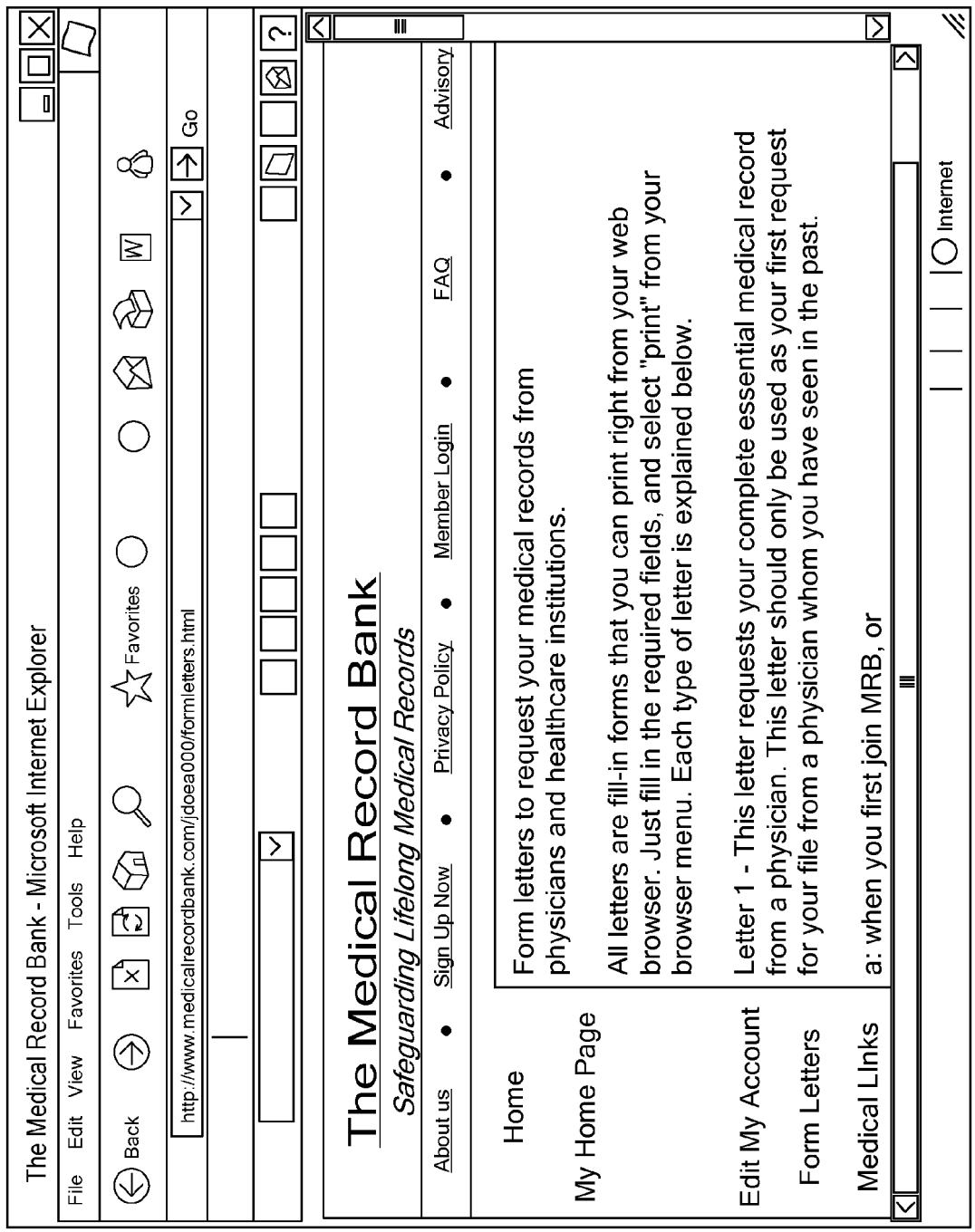
FIG. 24 is an illustration of a web page whereby the user may access form letters in accordance with the embodiment of FIG. 8.
Figure 25:
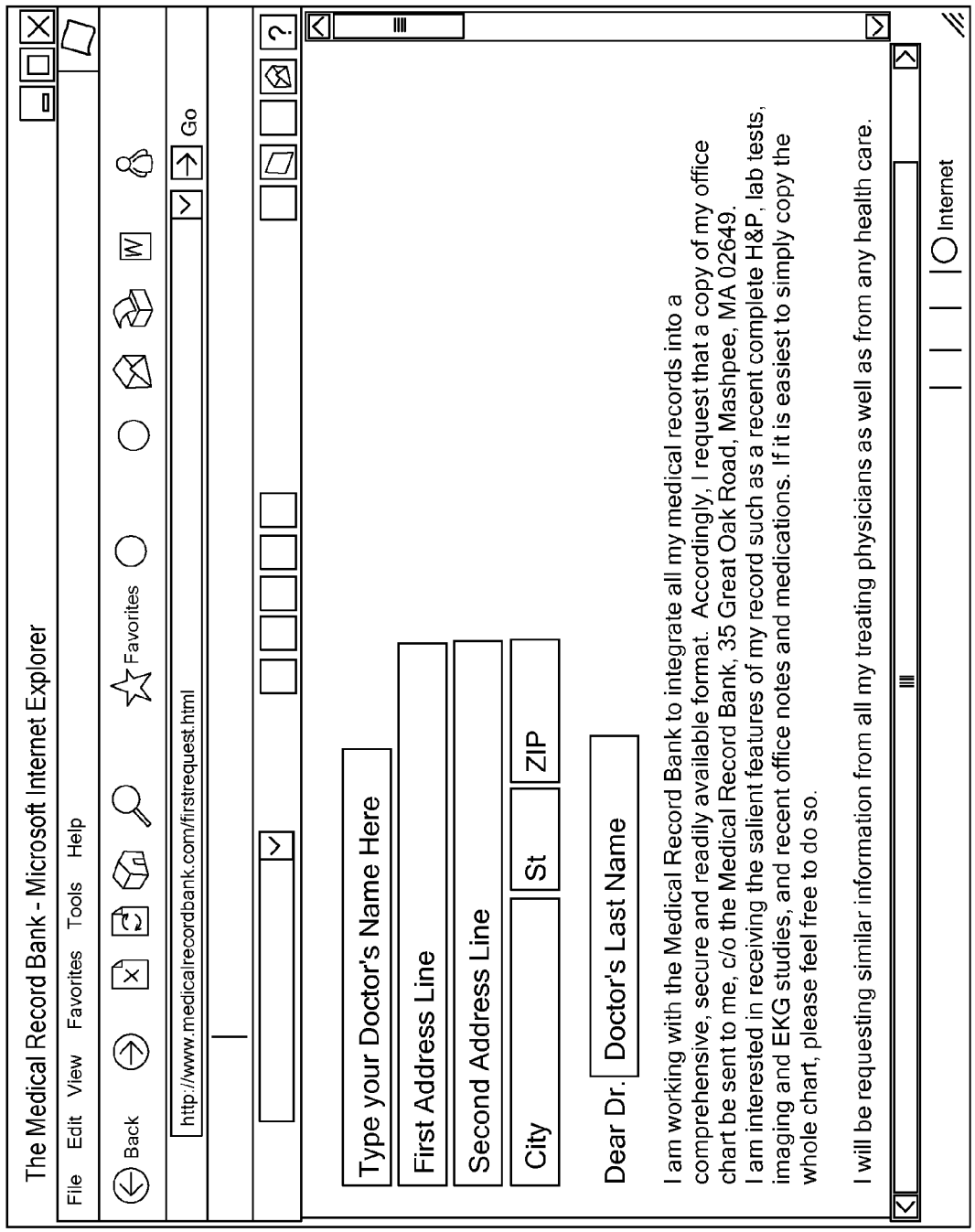
Figure 26:
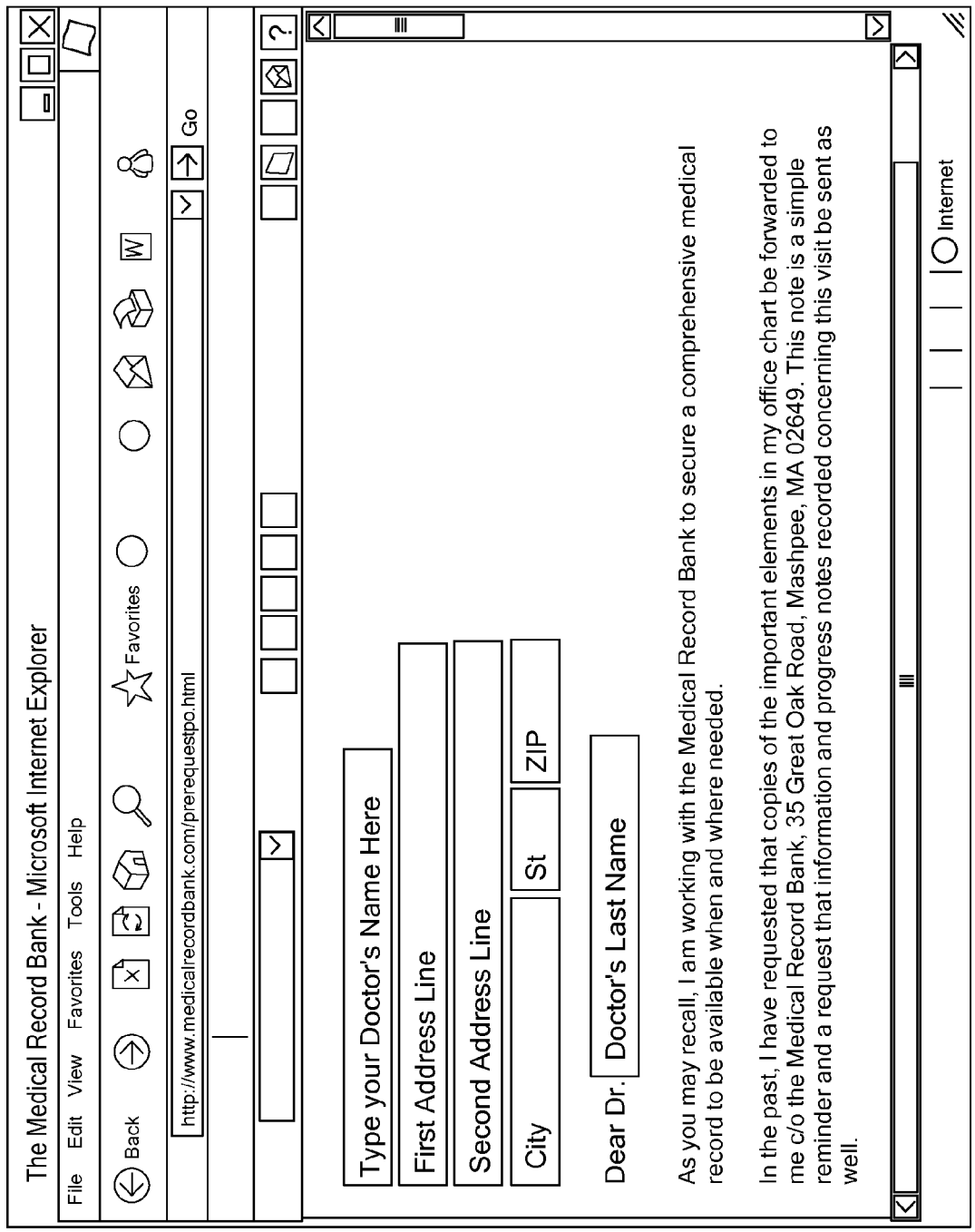
Figure 27:
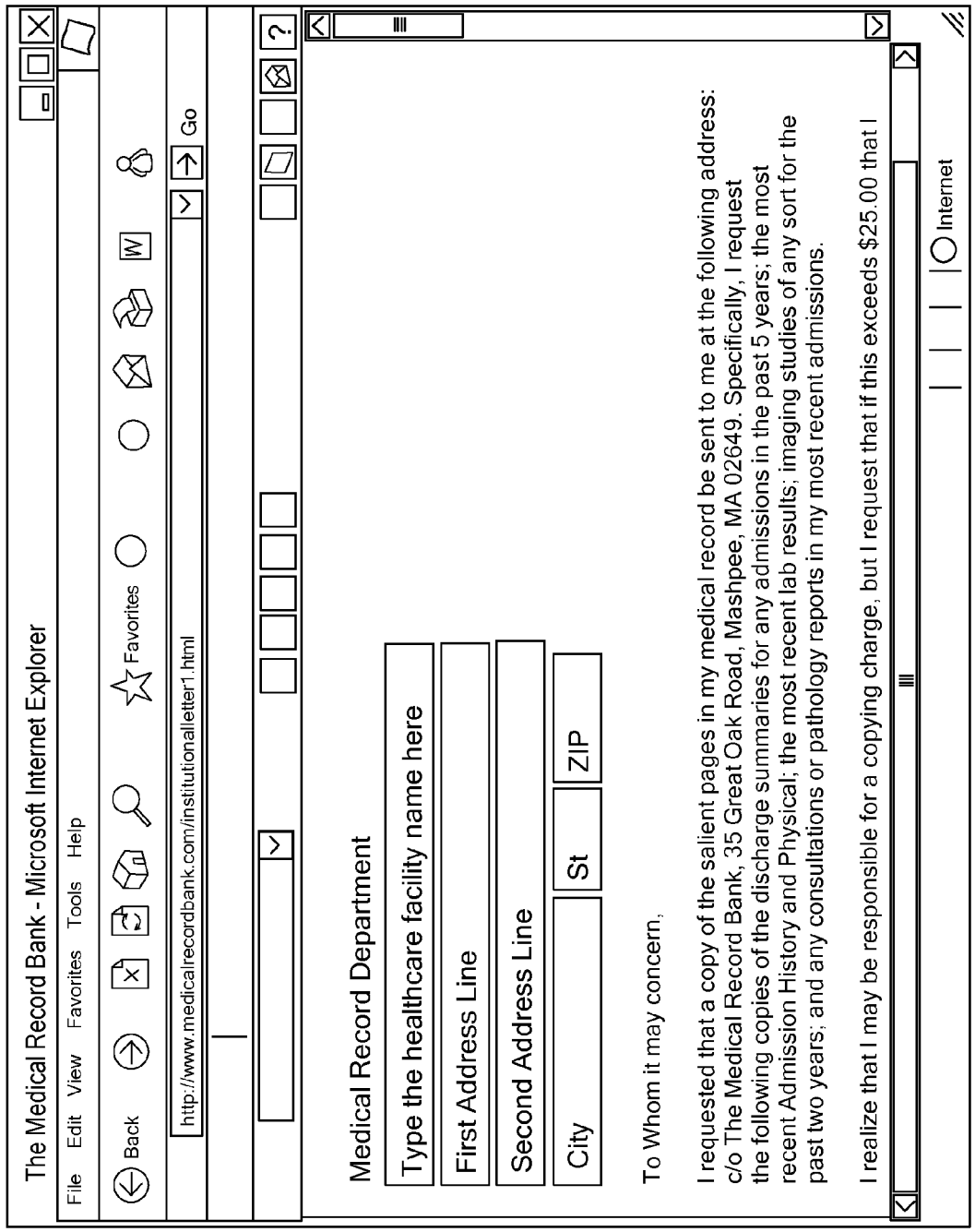
Figure 29A:
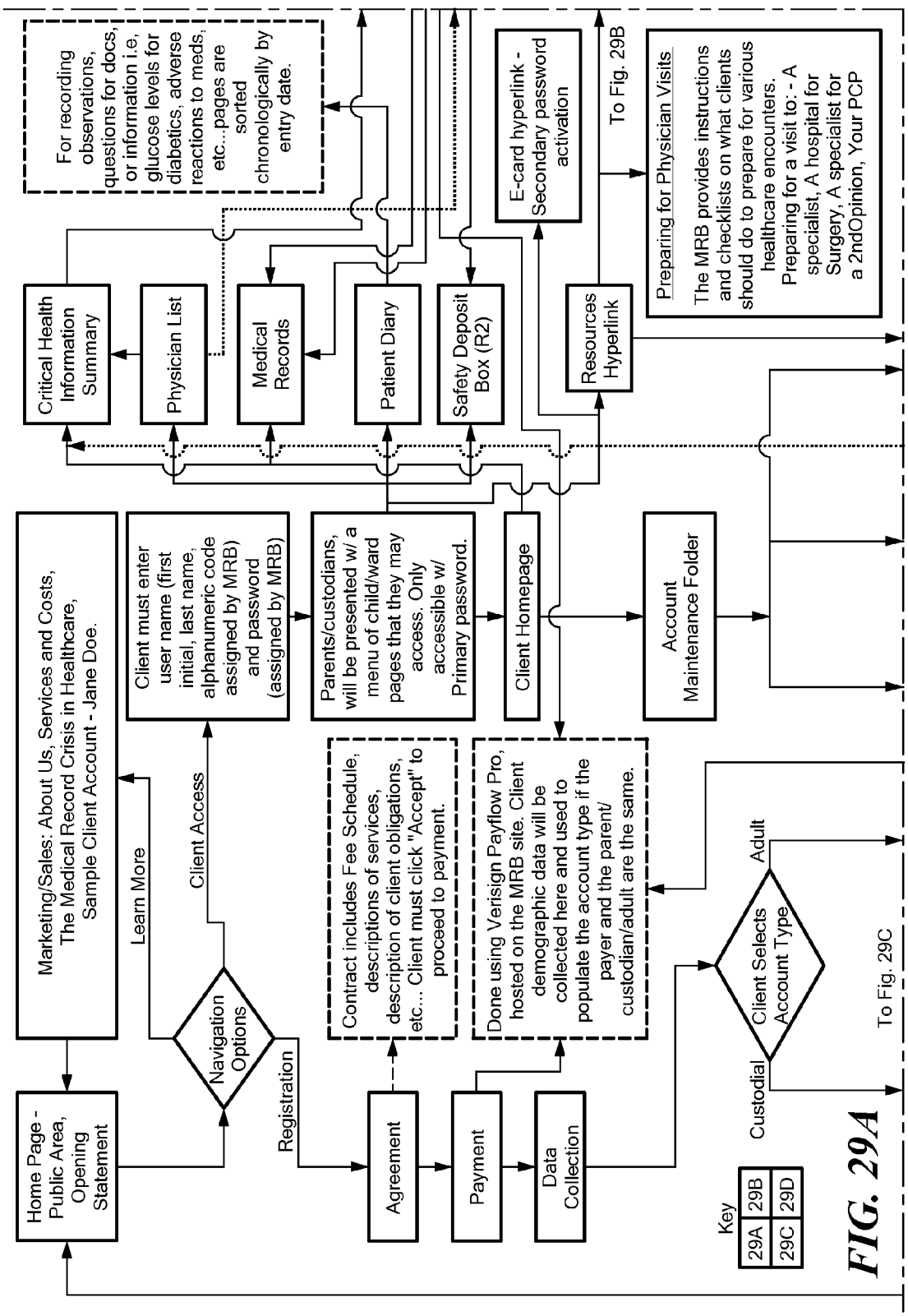
FIG. 29 is a flow diagram illustrating an overview of a method of providing a centralized medical history in accordance with another embodiment of the invention.
Figure 29B:
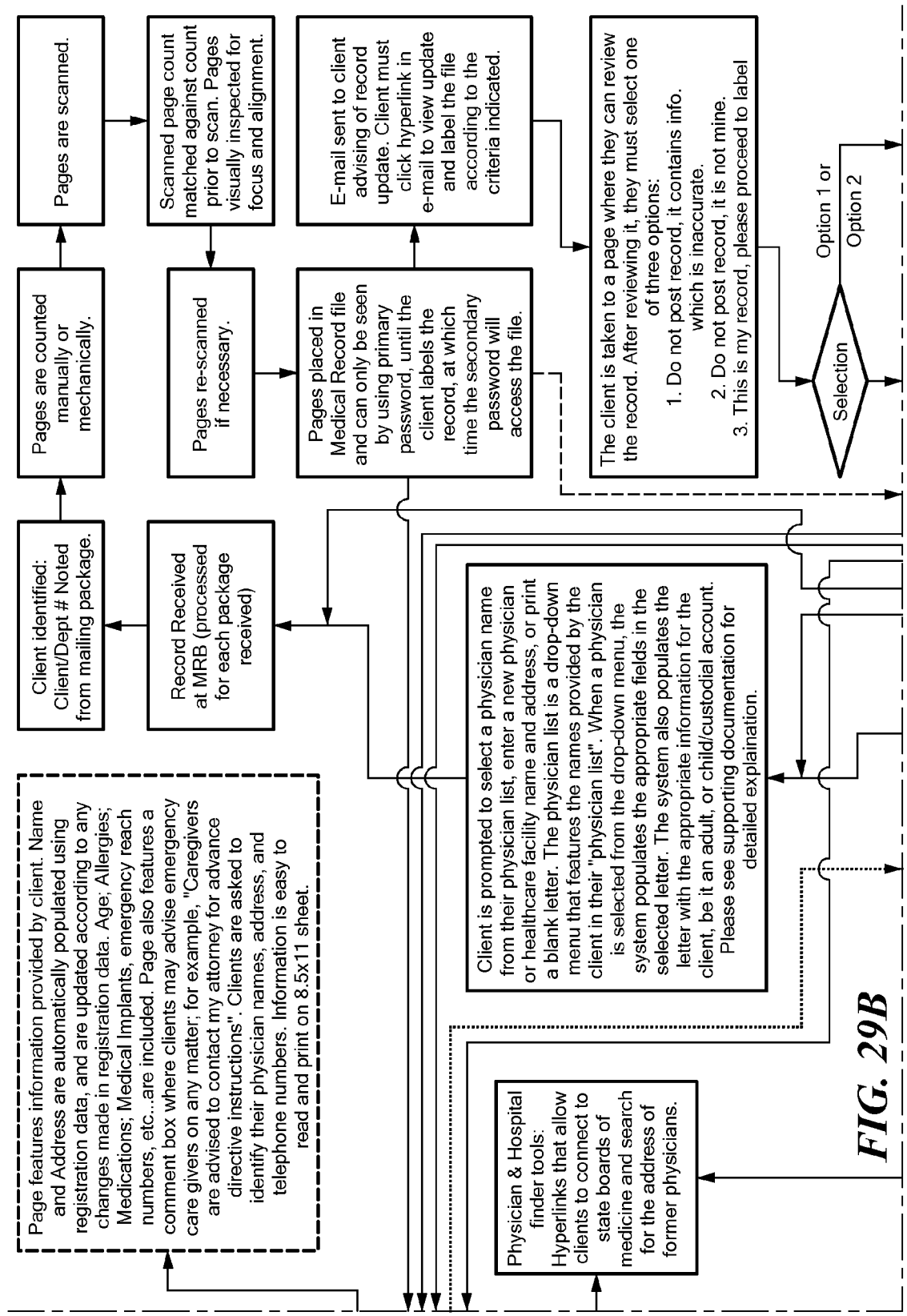
Figure 29C:
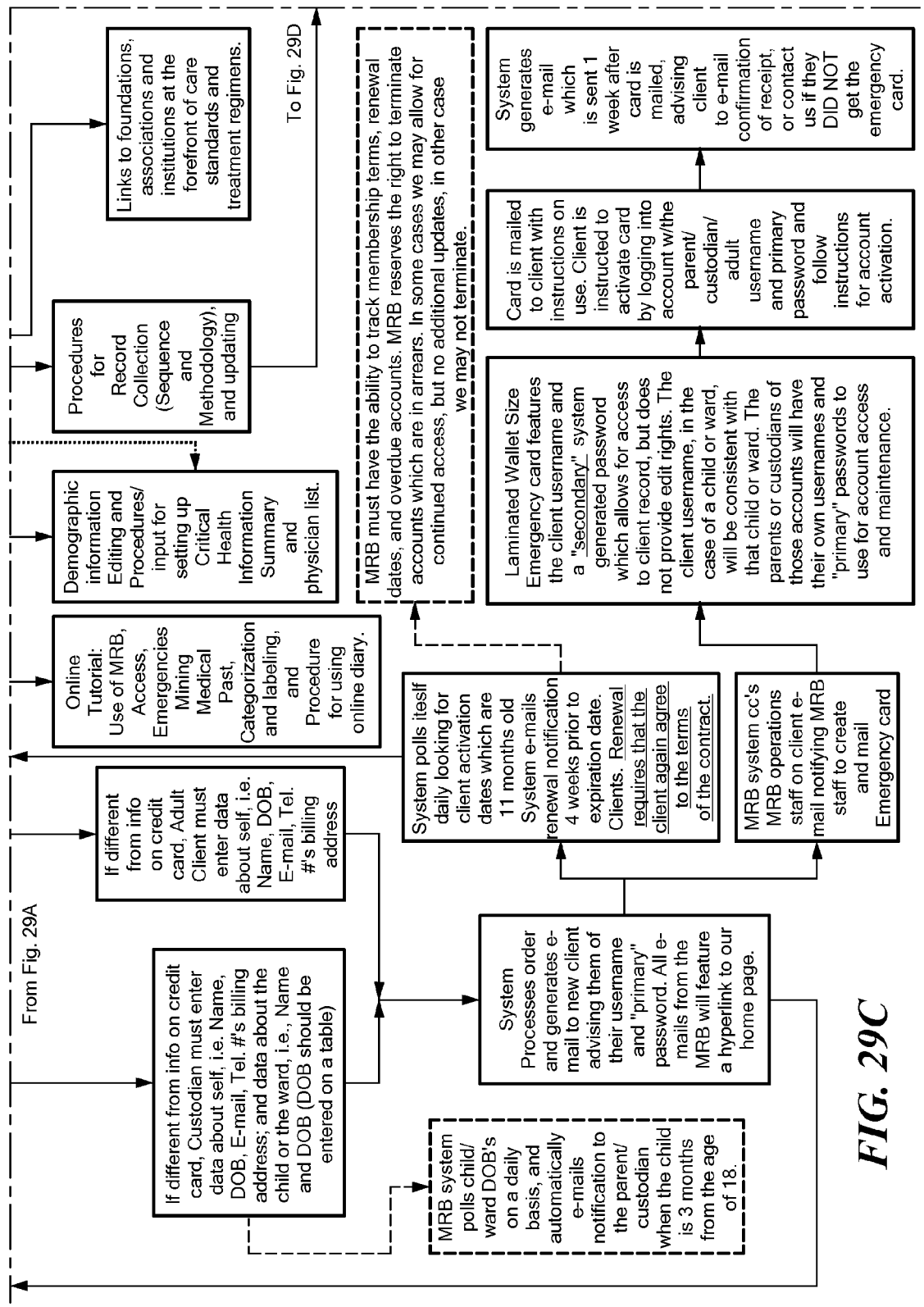
Figure 29D:
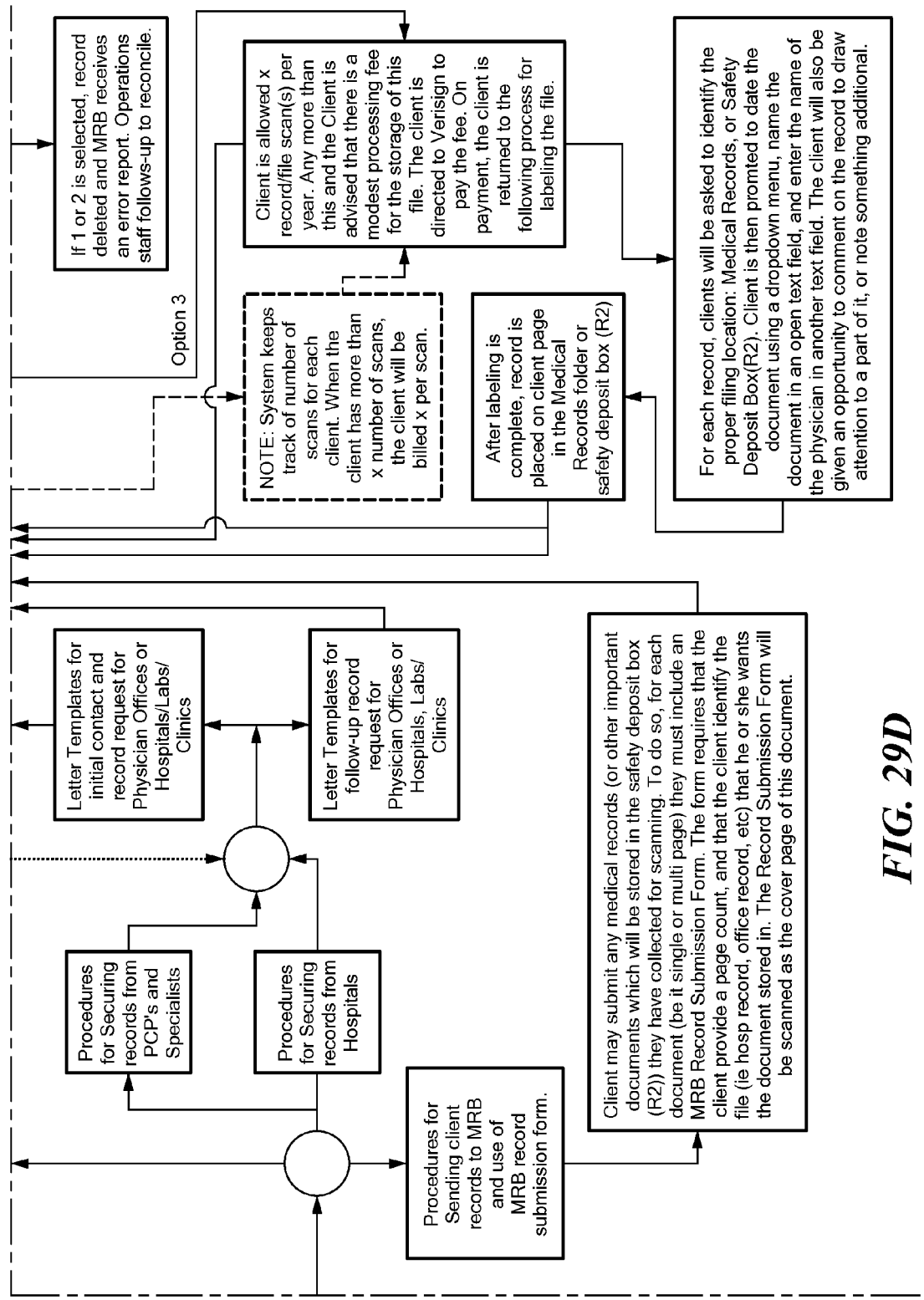
Figure 30A:
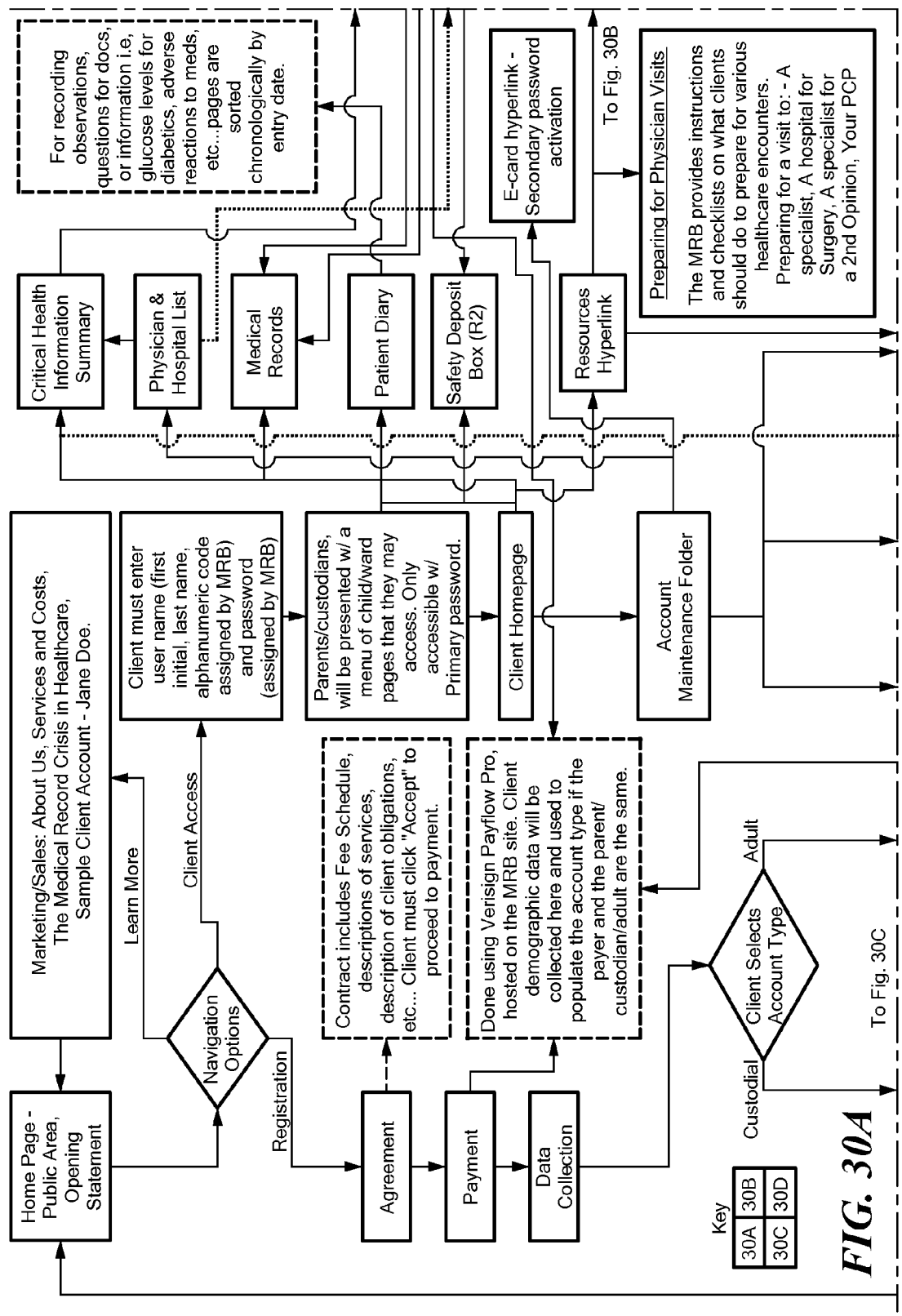
FIG. 30 is a flow diagram illustrating an overview of another method of providing a centralized medical history in accordance with another embodiment of the invention.
Figure 30B:
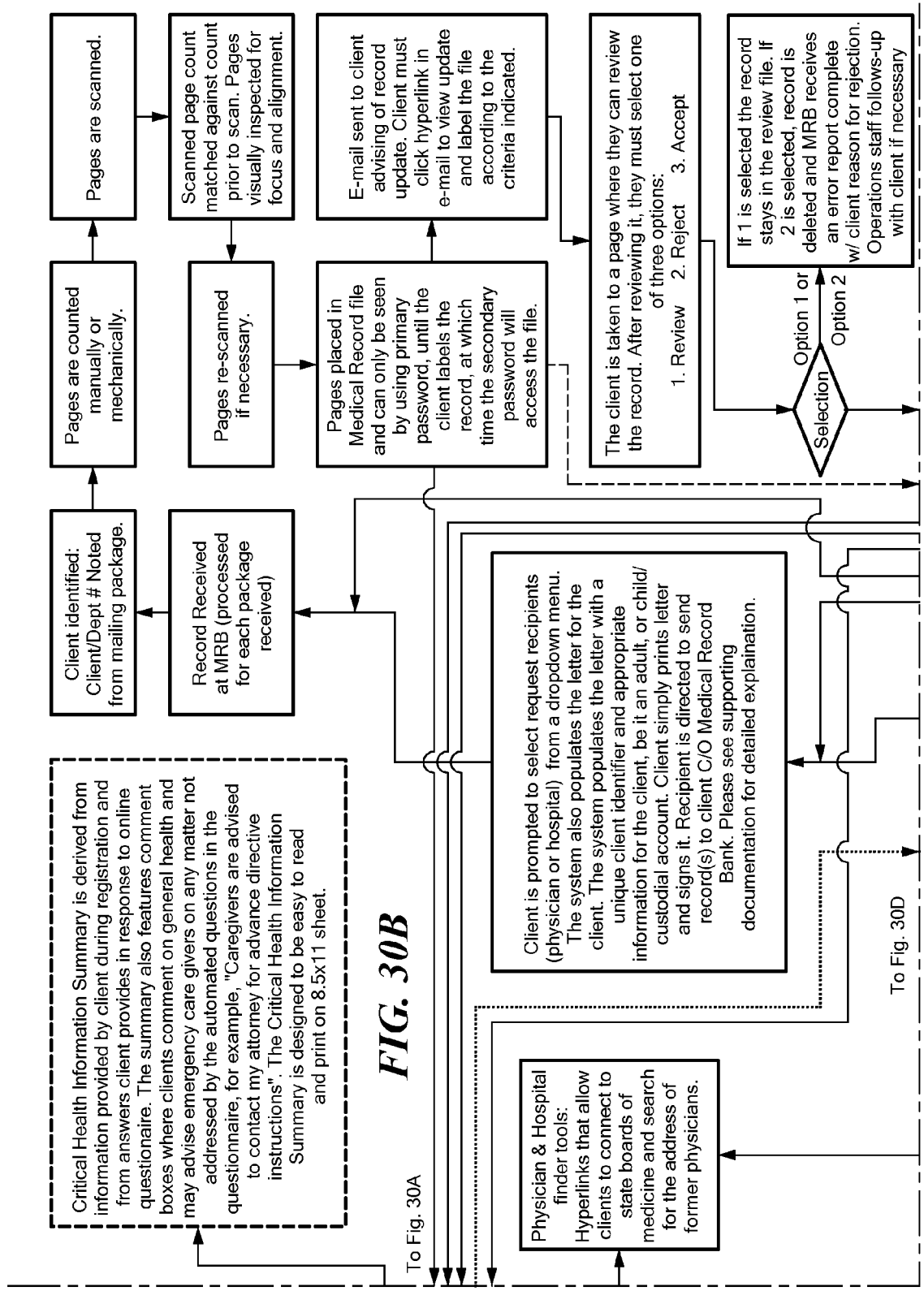
Figure 30C:
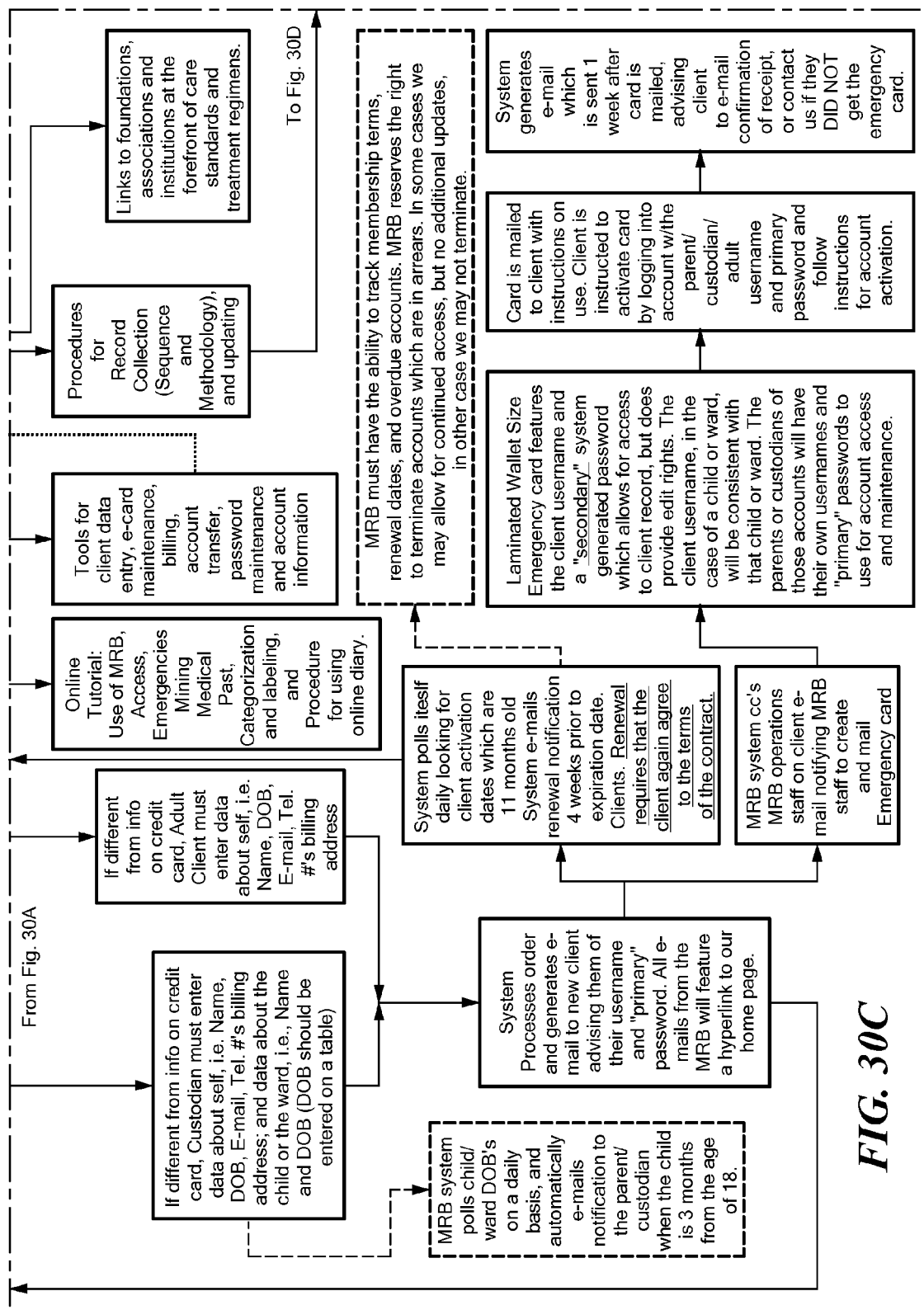
Figure 30D:
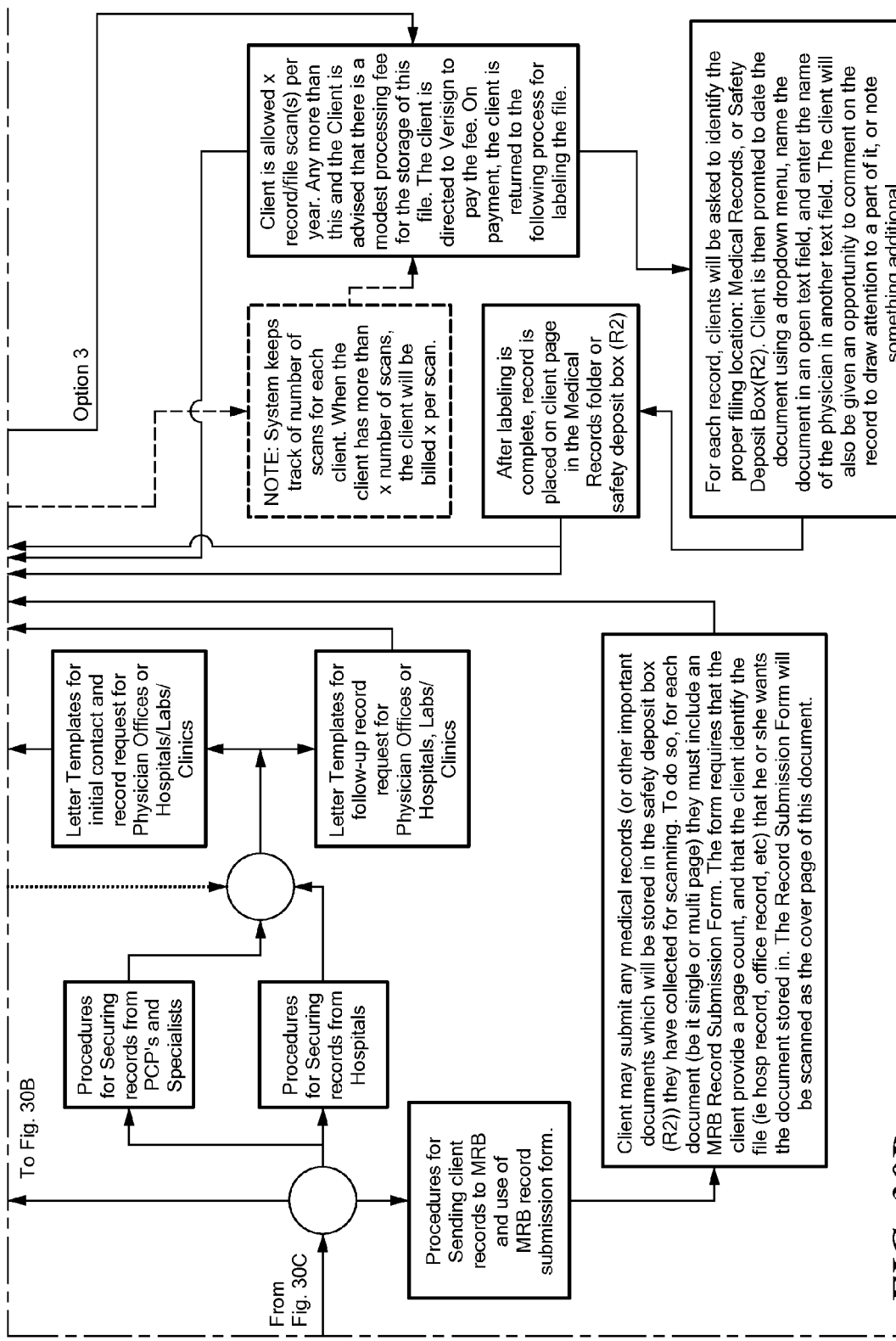

FIG. 24 is an illustration of a web page whereby the user may access form letters in accordance with the embodiment of FIGS. 1 and 8. Similarly, FIGS. 25-28 are illustrations of web pages whereby the user may view form letters in accordance with the embodiment of FIG. 24. In accordance with such form letters, the client may be prompted, in process 311, to enter a physical (or other medical facility) name and address. In accordance with this embodiment, each letter clearly states that correspondence concerning the client should be sent to the client (or to the client "in care of" the CMRS). The CMRS service provider may also instruct the client as to how to fill out the fields related to a return address and such fields may include a number which identifies the client so that data received from a physician or other medical facility or entity as a result of the letter in not assigned to the wrong account when the data is received by the CMRS service provider. Such an identifier may be part of the client's user name. The client may then print the letter out and mail it to the physician or other medical facility.

In process 108 of FIG. 1, the CMRS service provider scans any medical records or data provided by the client or provide as a result of the client's request to a physician, hospital, pharmacy, laboratory or clinic so that such medical records and data may be included in the client's centralized medical history. For example, the CMRS service provider may provide the client with a means to secure a copy of his or her medical records from the client's primary care provider or hospital one a regular basis, for example, once a year. The client's primary care physician's records may be complete with hospital discharge summaries and correspondence to and from any medical specialist that the client has been referred to that year. A client may be entitled to a free medical record scan, with no page limit, on a such periodic basis. Additional scanning of documents of any size may be provided at any time. The medical records or data are reviewed and labeled and placed into an electronic folder (which may describe, for example, a source of the record or data such as physician, hospital, clinic, pharmacy or other source) by the client in process 109.

Figure 23:
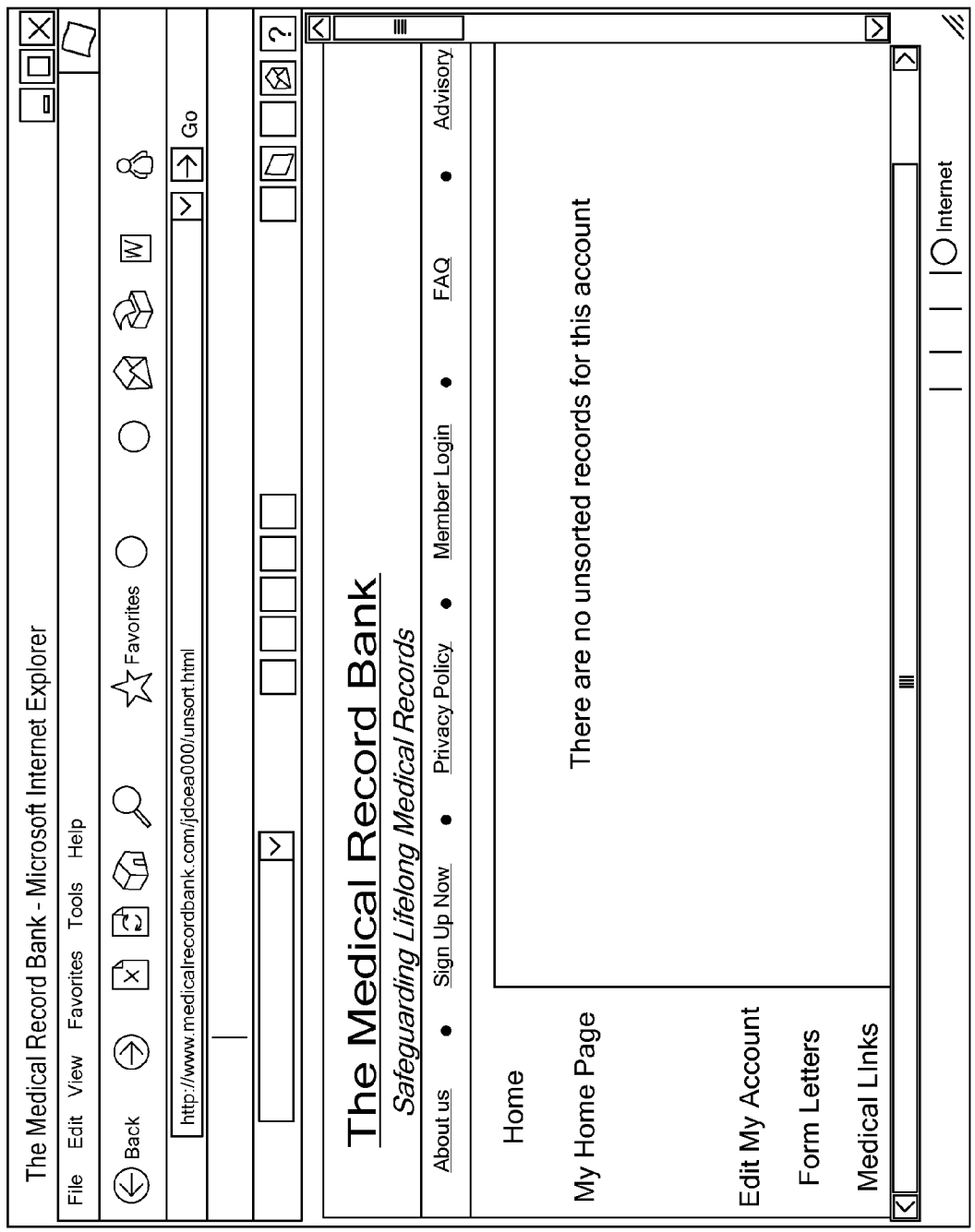
FIG. 23 is an illustration of a web page whereby the user may view unsorted medical records in accordance with the embodiment of FIG. 8.

FIG. 4 is a flow diagram illustrating a process by which medical records are included in the centralized medical history. In process 401, medical records and data are received by the CMRS service provider. The client's name and identifier number are noted, in process 402, from the mailing package or from client's email. Pages of documents containing the medical records or data are scanned, in process 403, by the CMRS service provider. The scanned page count is compared or matched, in process 405, with the page count of the document prior to scanning and the pages are inspected visually for focus and alignment. If necessary, the pages may be re-scanned in process 406. The scanned pages are placed, in process 407, in a staging area such as an "unclassified documents" folder on the client's home page and may be labeled with a scan date and/or time and/or other pertinent information. FIG. 23 is an illustration of a web page whereby the user may view unsorted medical records.

Such an unclassified documents folder may be accessible by the client's primary password or by a secondary password. An email is sent to the client, in process 408, whereby the client is notified of a medical record update. The client may click on a hyperlink in the email to view the updated information. Upon viewing the updated information, the client may select one of several hyperlinks to indicate, for example, that the record should not be included in the client's medical history because it does not belong to the client or that the record does belong to the client and that the labeling process should proceed.

The client may make notations with respect to and/or label the updated information with the appropriate physician, hospital, laboratory, clinic or other name, and categorize the updated information as desired. During the labeling process, the client may be prompted by the CMRS to provide an online description of the medical record or data and a service date. In process 409, the labeled information the client may place the updated information in an appropriate folder in accordance with the client's system of categorization.

In process 110 of FIG. 1, the medical records or data may be edited by the client. FIG. 5 is a flow diagram illustrating a process by which medical records are edited. In accordance with the embodiment of FIG. 5, if a client believes that information contained in a file is misleading or inaccurate, the client may visually tag, in process 501, the relevant page or pages as pages that should not be used by a healthcare provider. The client may also contact, in process 502, the appropriate healthcare provider to secure revised or amended medical records or data. The CMRS service provider, in process 503, may provide a procedure and/or a form letter template for the client to use to send the CMRS service provider an amendment after the client has secured such an amendment from the healthcare provider. The CMRS may also link, in process 504, any amended medical record or data to the original medical record or data that has been amended. Such revisions may be placed, in process 505, in a "miscellaneous/errata" file or folder. Dental and/or optical records or data may also be placed in this folder.

Alternatively, when the client receives an email is notifying him or her of a medical record update, the client may view the updated information and select a hyperlink to indicate, for example, that the record should not be included in the client's medical history because it does not belong to the client or that the record does belong to the client and that the labeling process should proceed. In this manner, if the updated information is inaccurate or misleading, the client may prevent the information from being included in his or her history. In this case, information on advance directives may be found in the client's health summary and the client is not able to edit or tag the record itself.

Figure 6:
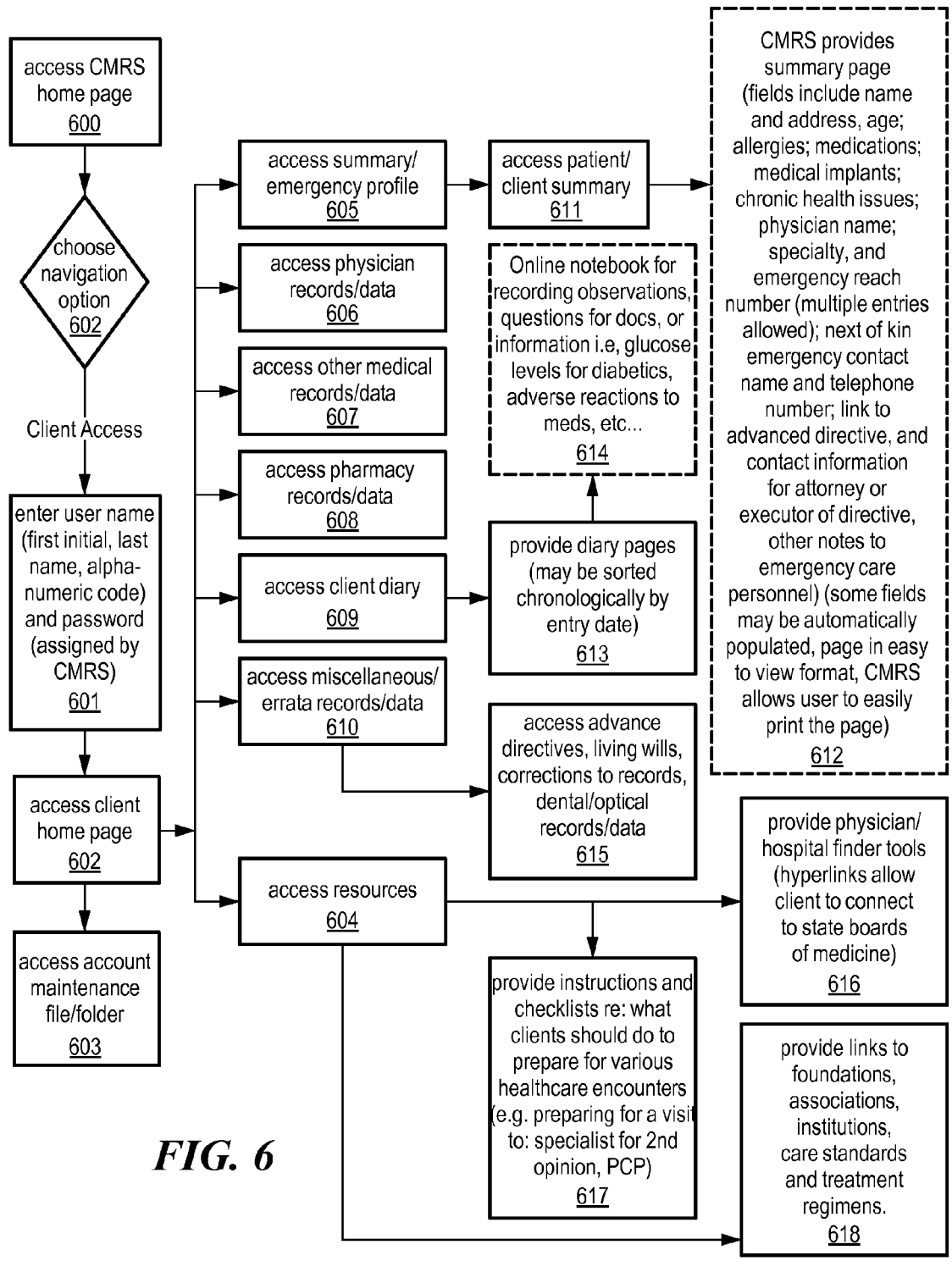
FIG. 6 is a flow diagram illustrating a process by which a client may navigate through a medical history in accordance with the embodiment of FIG. 1.
Figure 7A:
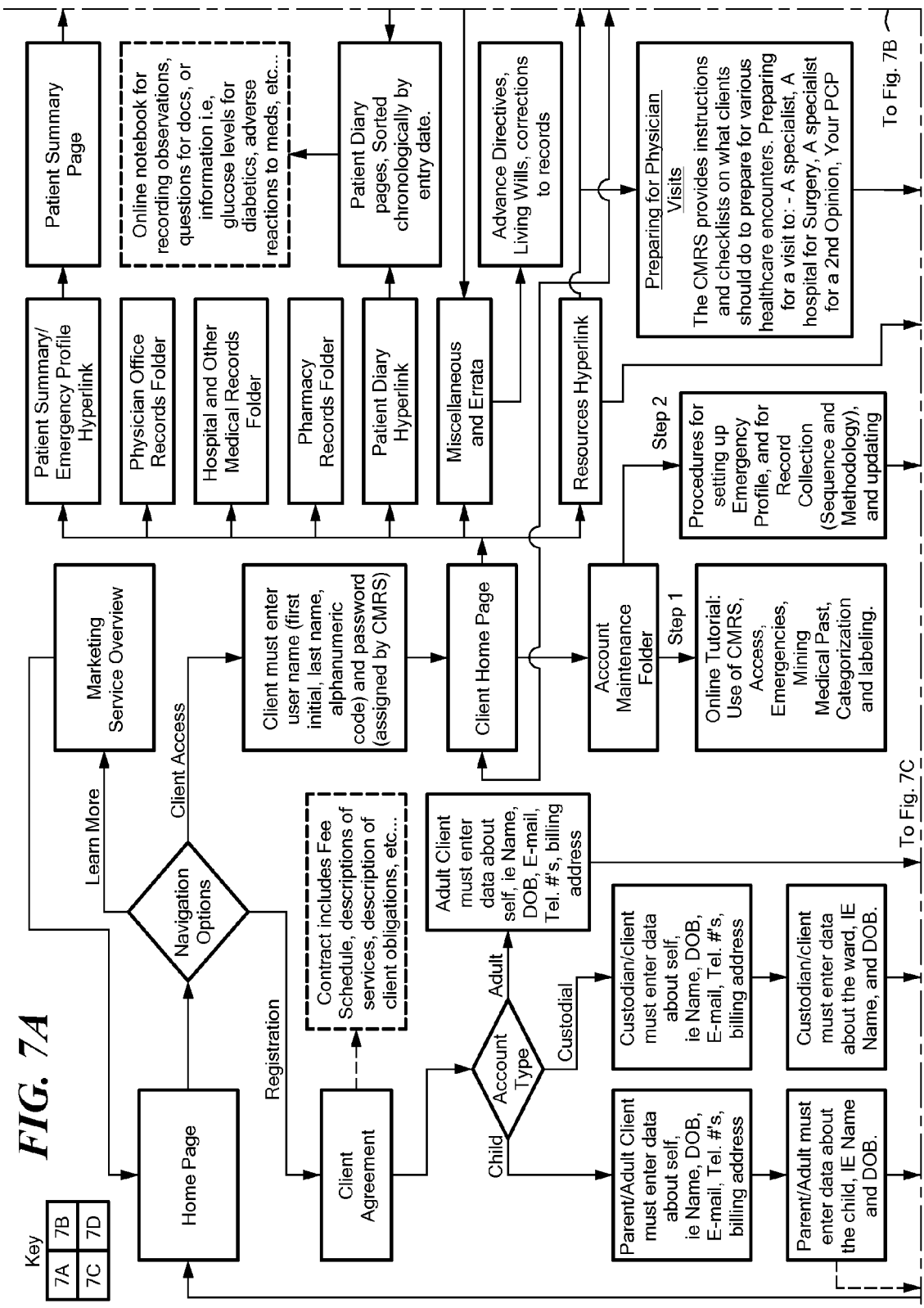
FIG. 7 is a flow diagram illustrating an overview of a method of providing a centralized medical history in accordance with another embodiment of the invention.
Figure 7B:
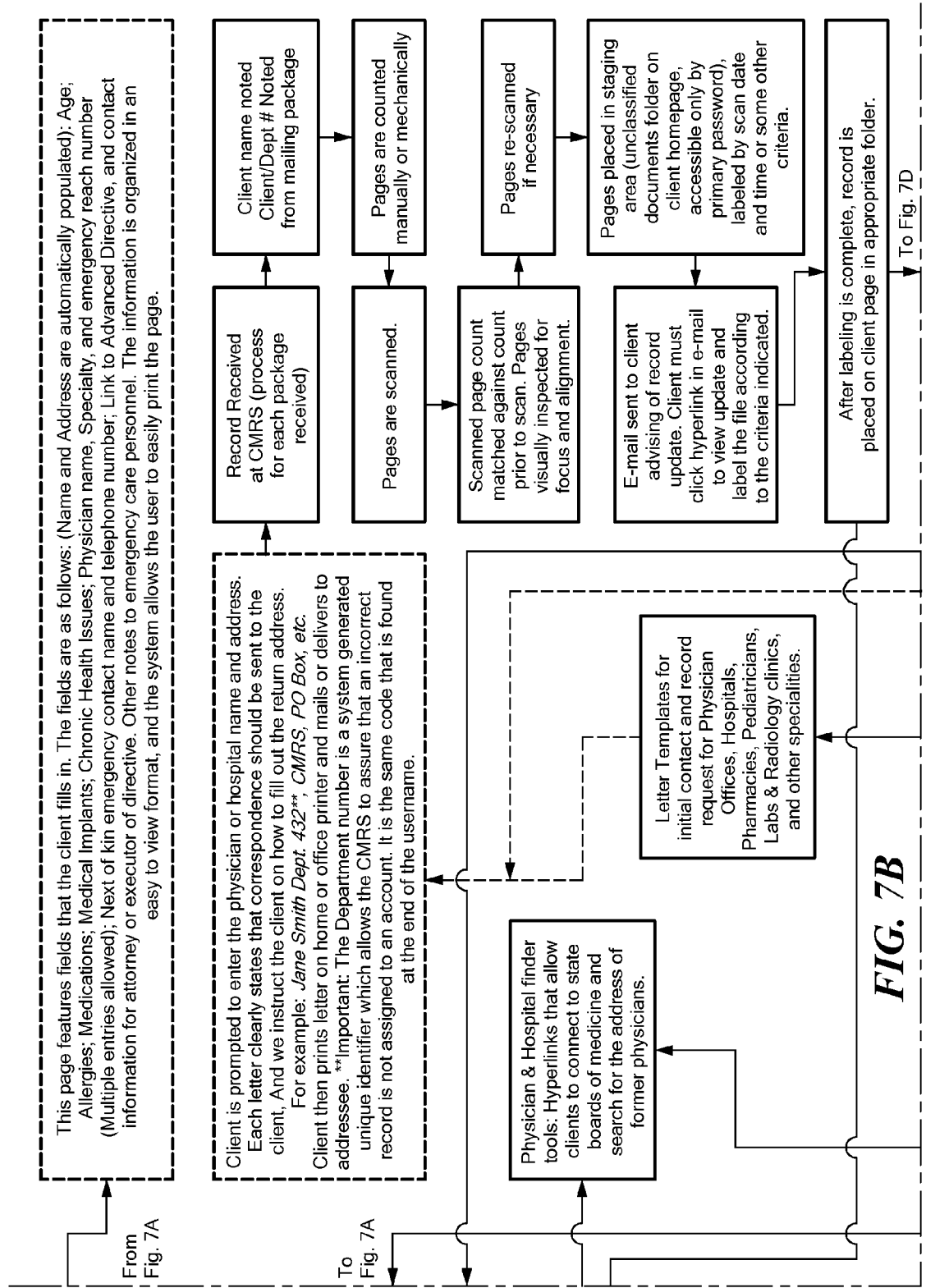
Figure 7C:
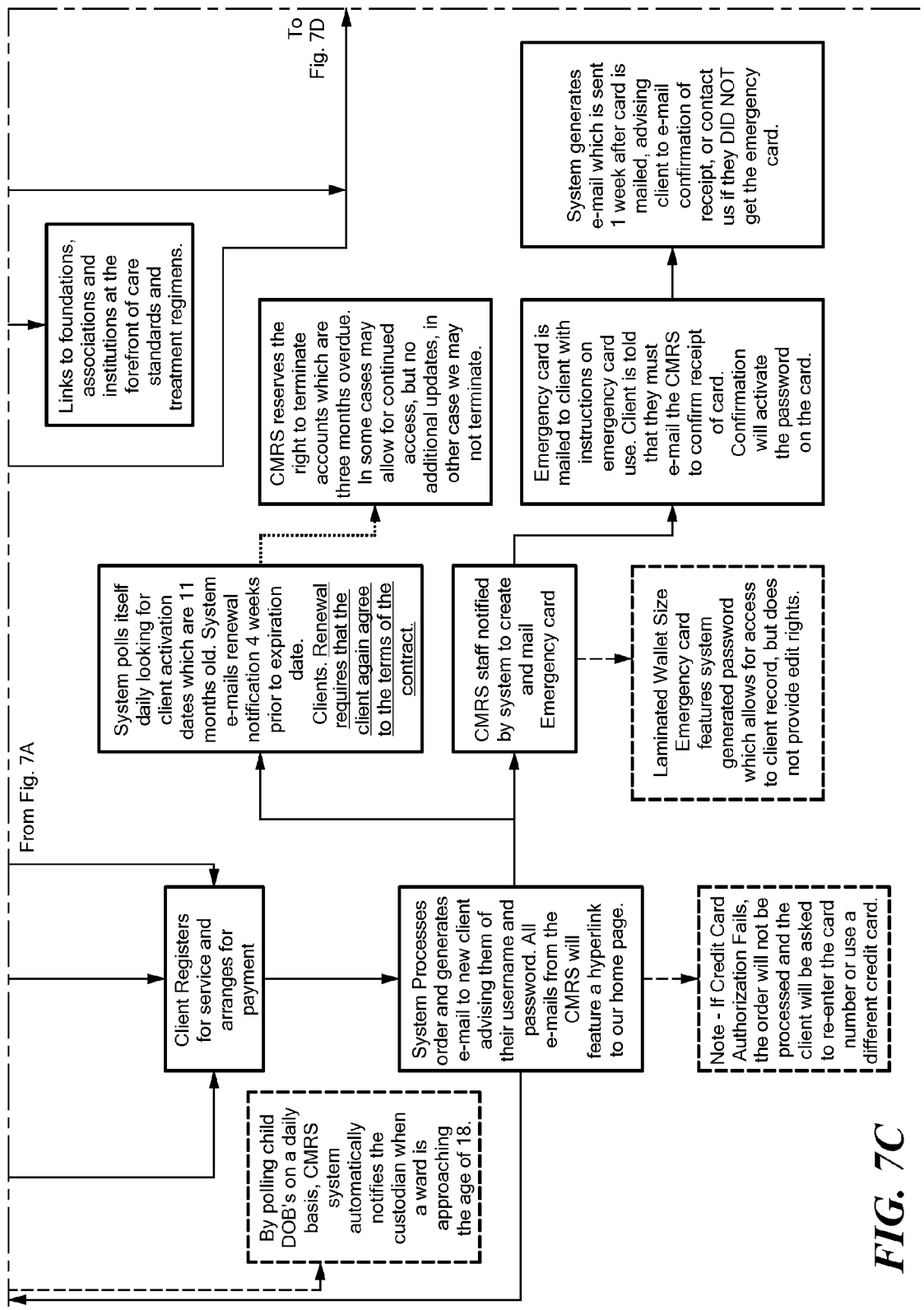
Figure 7D:
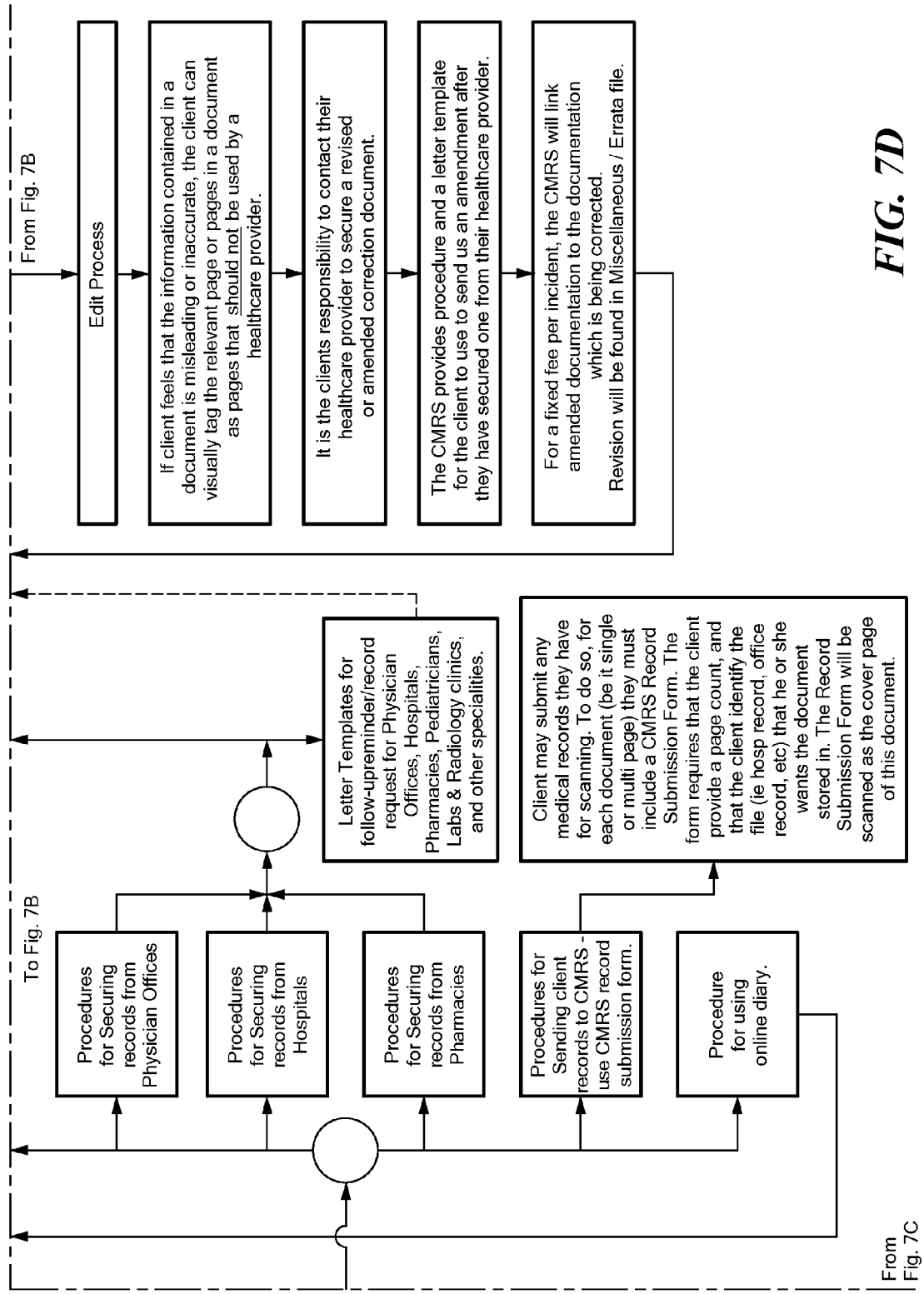

The medical records and/or data may be retrieved and prepared for healthcare encounters in process 111 of FIG. 1 and the client may update his or her client diary in process 107. FIG. 6 is a flow diagram illustrating a process by which a client may navigate through a medical history to retrieve medical records or data. In process 600, the client accesses the CMRS home page and chooses, in process 620, navigation options. In process 601, the client must enter a user name (such as a first initial, last name, and/or alphanumeric code) as well as his or her primary password. FIG. 13 is an illustration of a web page that provides a graphical user interface whereby a client by submit his or her user name and password for medical record or data retrieval. The client will be allowed access, in process 602, to his or her client home page such as the client home page illustrated in FIG. 14. The client may access an account maintenance file or folder, in process 603, via his or her home page. Further, the CMRS service provider may provide a folder that allows a client to store any type of document he or she wishes to be included in the online file. In accordance with one embodiment, access to such a file may be provided to the client via the client's primary password. Similarly, the client may access other medical resources, in process 604, via his or her home page. When the client or other user accesses these resources, the CMRS may provide, in process 616, physician and hospital finder tools, such as hyperlinks that allow the client or user to connect to state boards of medicine and search for information about physicians (such as a former physician's address). The CMRS may also provide, in process 618, links to foundations, associations and instructions relating to standards of care and treatment regimens.

The client may further access his or her medical history via his or her home page. For example, if the client would like to access the critical information about herself, she may do so through hyperlink 1401. If the client would like to access physician office records related to her healthcare, she may do so through hyperlink 1402. Similarly, if the client would like to access hospital or other healthcare facility or entity records (such as records from laboratories and/or clinics) the client may do so via hyperlink 1403. Alternatively, both physician and hospital records may be accessed via one hyperlink.

Figure 15:
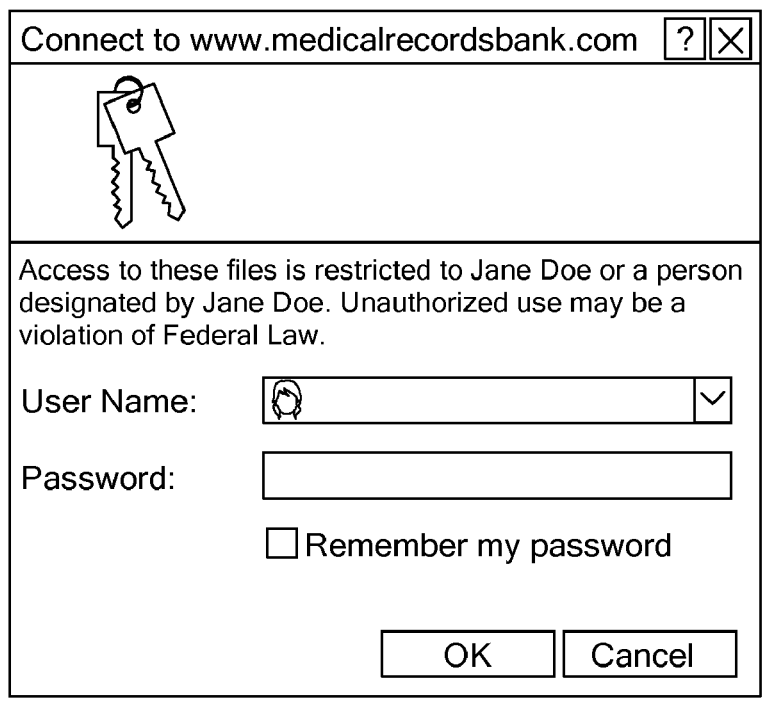

If the client would like to access pharmacy records, the client may do so via hyperlink 1404. Alternatively, such information may be access via the client health summary. There may also be hyperlinks whereby the client may access any miscellaneous and errata data and his or her client diary. When the client clicks on one of these hyperlinks, the CMRS will provide another graphical interface, such as shown in FIG. 15, to notify the user that access to the medical records or data is restricted to the client or a user designated by the client. The CMRS may then require the user to provide his or her user name and either the primary password or the secondary password described above in relation to the emergency card. (Note that the patient's primary care physician or other healthcare provider may also be designated as a user and be given a secondary password if the client so desires.)

Figure 16:
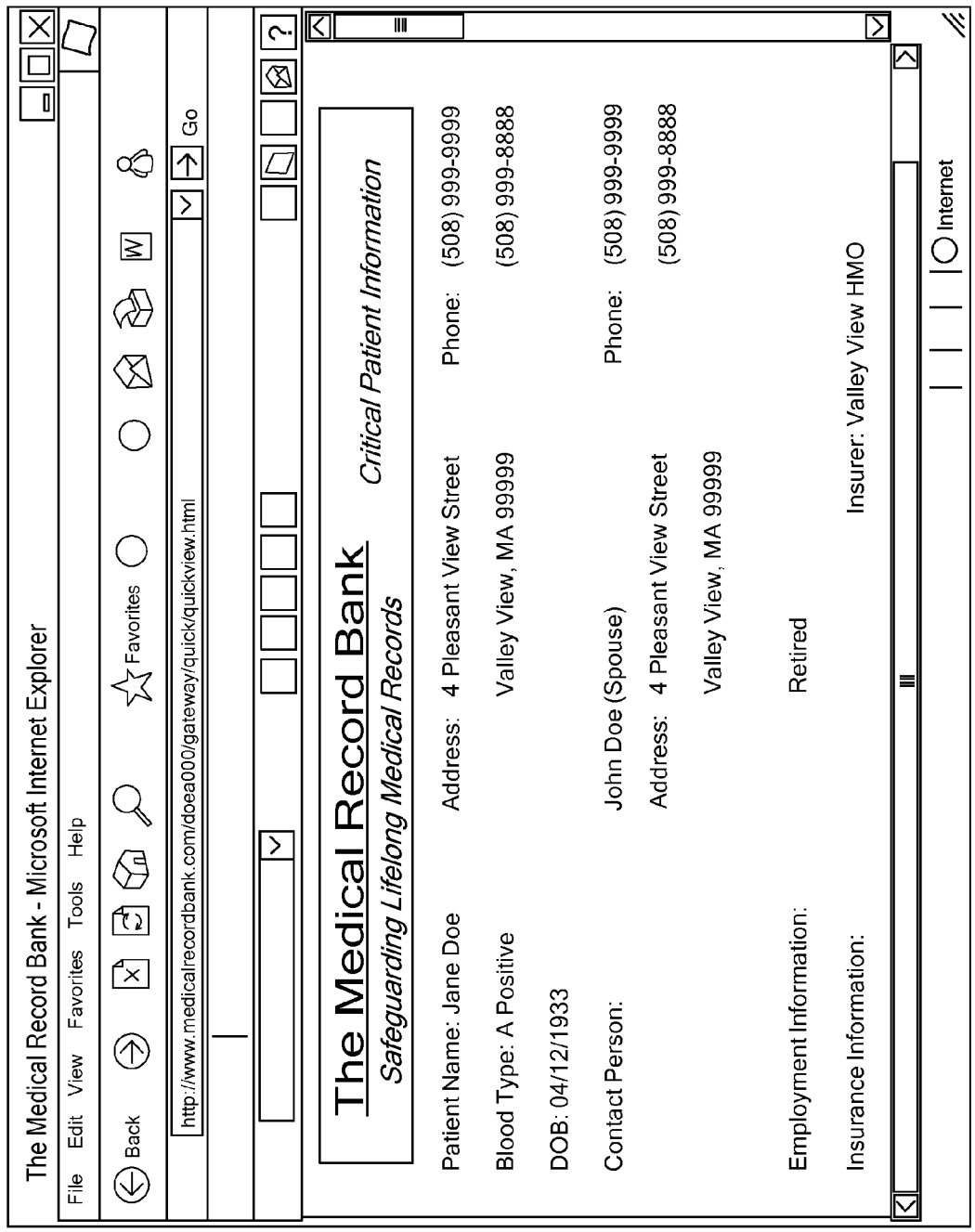
FIG. 16 is an illustration of a web page whereby the user may view critical patient information in accordance with the embodiment of FIG. 8.

The client (or other designated user) may then access, in process 605 his or her patient summary page and/or emergency profile. If the client chooses access his or her patient summary page, as in process 611, the CMRS service provider may provide, in process 612, a page that features fields that the client fills in to create a patient summary. The fields may include a "name" field and an "address", an "age" field, one or more "allergies" fields, one or more "medication" fields, one or move "medical implants" fields, one or more "chronic health issues" fields one or more "physician name" fields, one or more "physician specialty" fields and one or more "emergency contact name" and "emergency contact number" fields. The fields may also include one or more "emergency reach telephone number" fields as well as one or more fields for supplying a link to an "advanced directive" and one or more fields for "attorney contact" information or "executor of directive contact" information. The fields may also include field for "notes" to emergency care personnel. Some fields may be automatically populated by the CMRS, the information may be organized in an easy to view format, and the CMRS may permit the client or other user to easily print the page. FIG. 16 is an illustration of a web page whereby the user may view such critical patient information.

Figure 17:
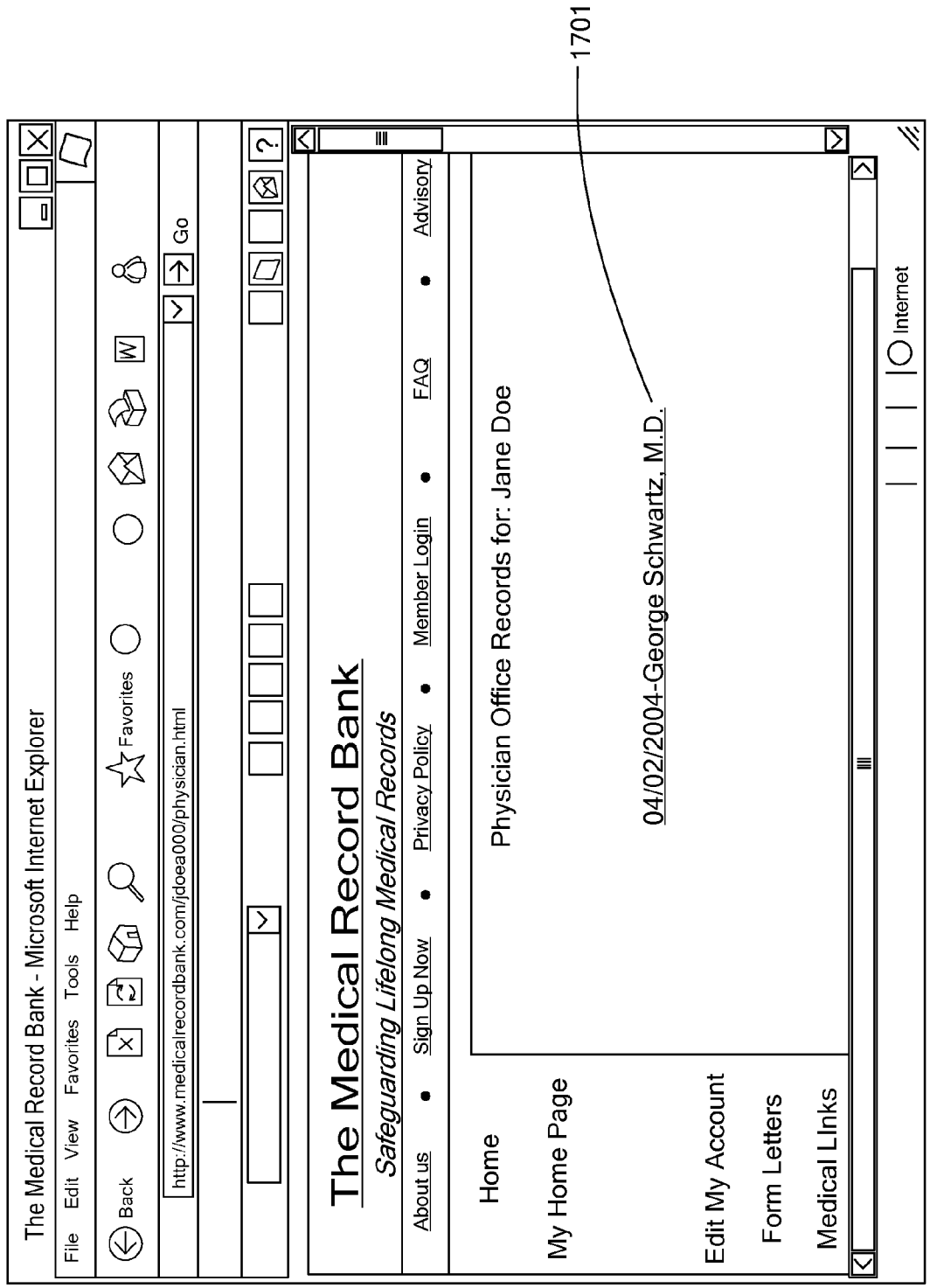
FIGS. 17-18 are illustrations of web pages whereby the user may view physician office records in accordance with the embodiment of FIG. 8.
Figure 18:
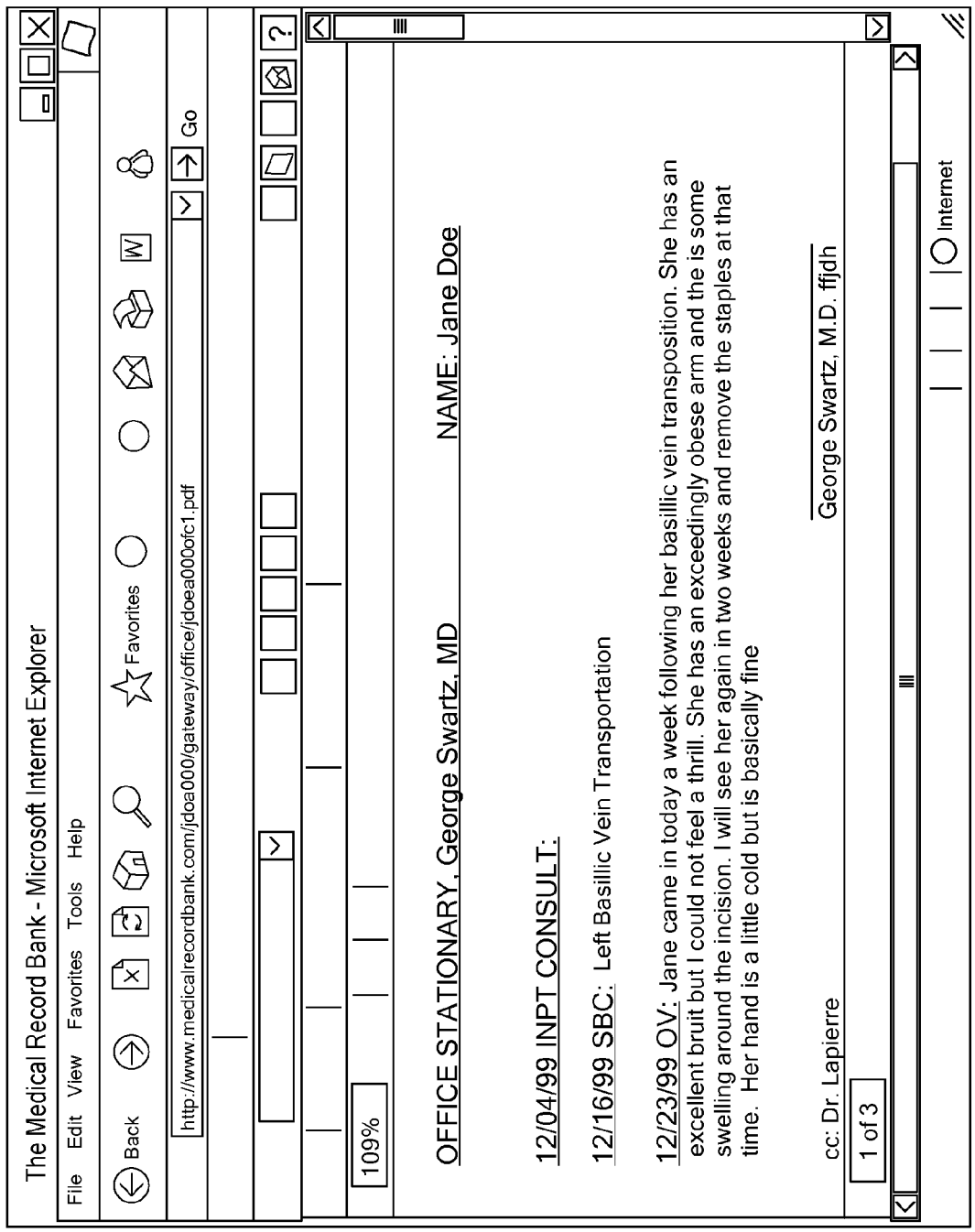
Figure 19:
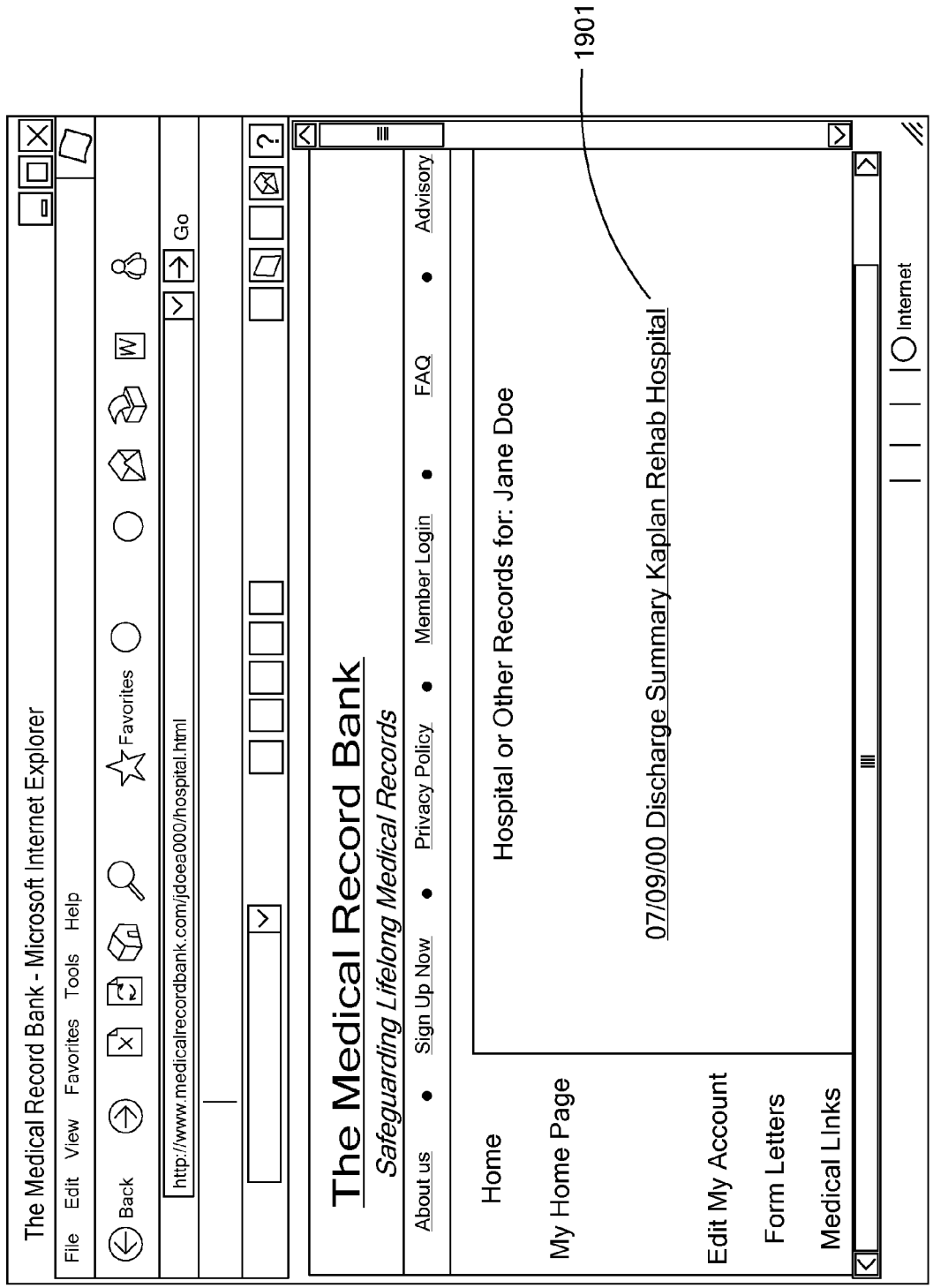
FIGS. 19-20 are illustrations of web pages whereby the user may view hospital records in accordance with the embodiment of FIG. 8.
Figure 20:
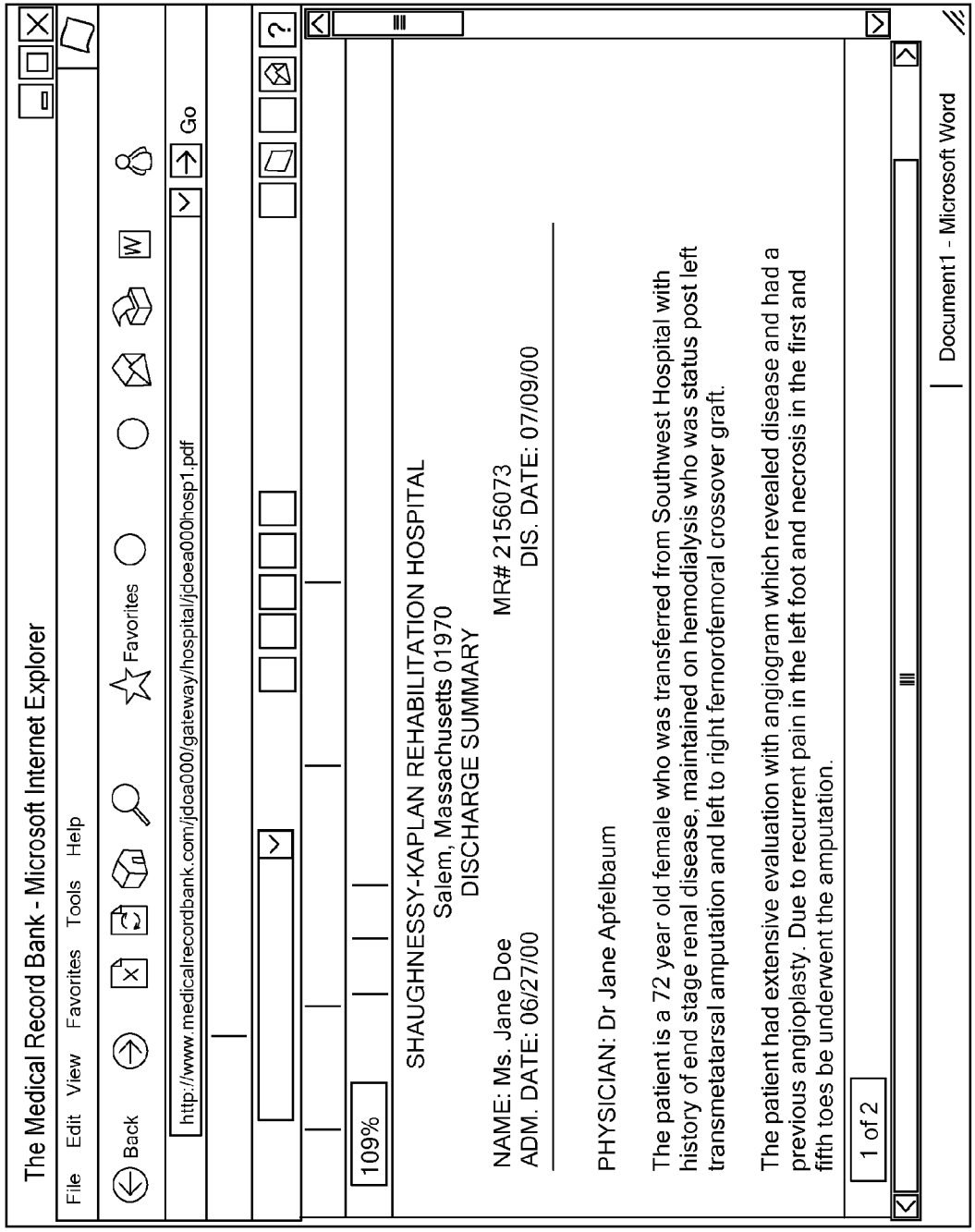
Figure 21:
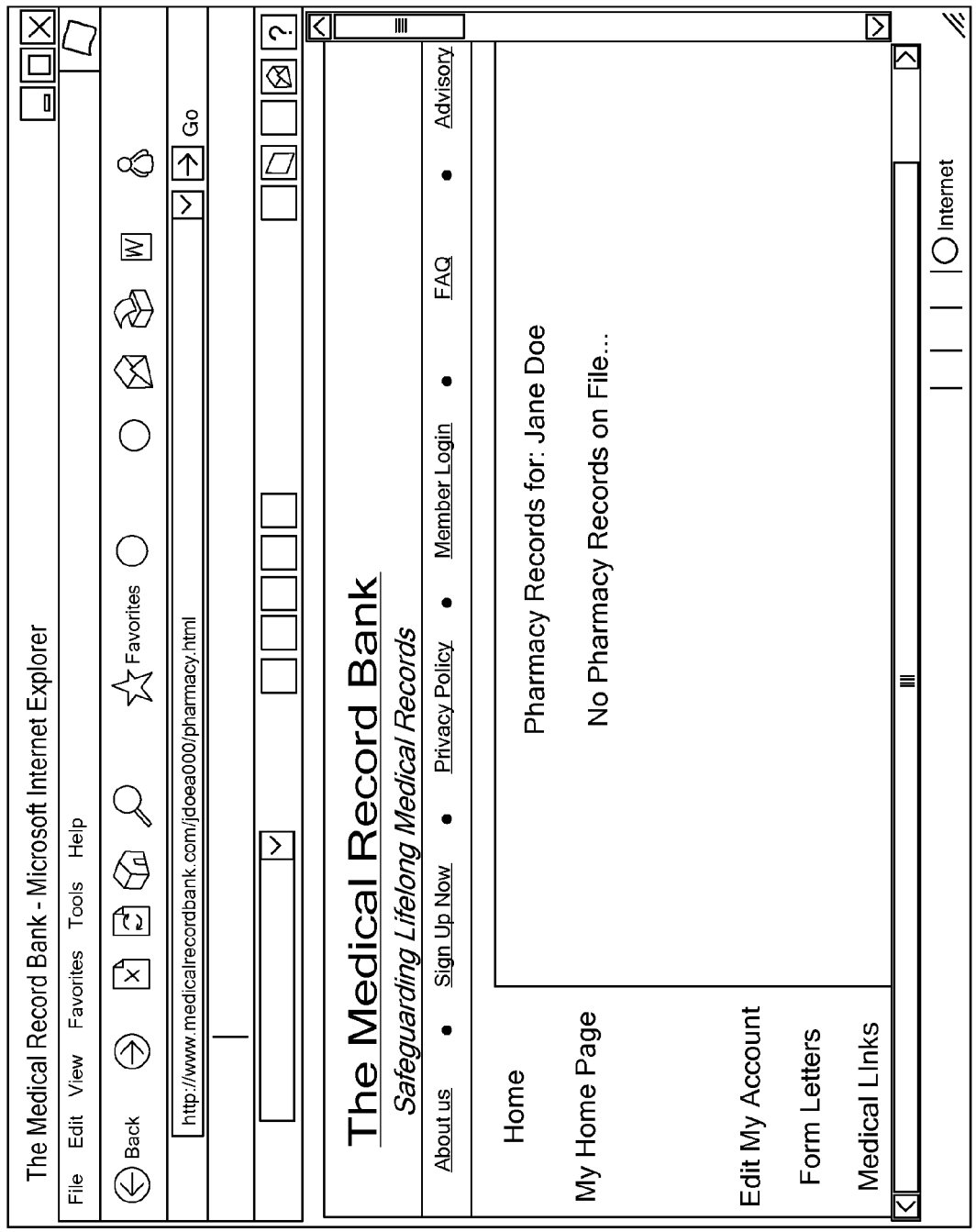
FIG. 21 is an illustration of a web page whereby the user may view pharmaceutical records in accordance with the embodiment of FIG. 8.

A client or other user may access, in process 606, information provided by a physician or a physician's office. FIGS. 17-18 are illustrations of web pages whereby the user may view such physician records or data. For example, the user may click on the hyperlink labeled by the date of the record and the physician's name shown at 1701. The CMRS service provider will provide the scanned record, as shown in FIG. 18, for the client or other user to view. Similarly, the user may access, in process 607, hospital or other healthcare facility or entity records (such as records from laboratories and/or clinics). FIGS. 19-20 are illustrations of web pages whereby the user may view such records. For example, the client or other user may click on the hyperlink labeled by the date of the record and the name of the hospital as shown at 1901. The CMRS service provider will provide the scanned record as shown in FIG. 20 for the client to view. The user may access, in process 608, information associated with a pharmacy or pharmaceuticals. FIG. 21 is an illustration of a web page whereby the user may view such records or data. (Note that data provided by physicians or physician offices, hospitals, clinic, laboratories or pharmacies may not be edited by the client or other user directly. To make amendments the client must use the process discussed in relation to FIG. 5).

Figure 22:
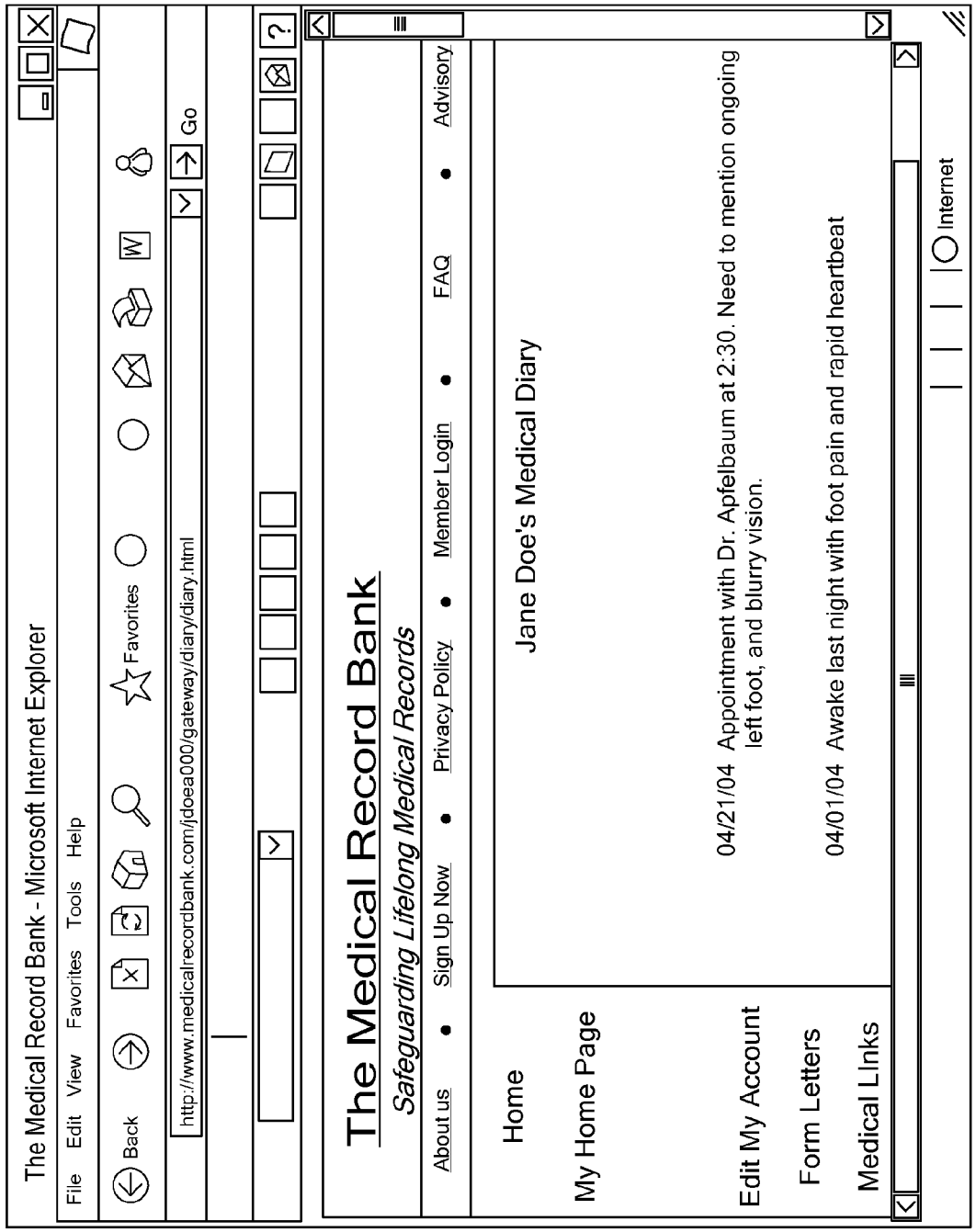
FIG. 22 is an illustration of a web page whereby the user may view a medical diary in accordance with the embodiment of FIG. 8.

The client may also access his or her client diary for viewing and editing in process 609. The CMRS will provide, in process 613, pages sorted chronologically by entry date. The CMRS may also provide, in process 614, an online notebook for recording observations, questions for physicians, or recording information such as glucose levels for diabetics, adverse reactions to medications, etc. FIG. 22 is an illustration of a web page whereby the client may view his or her diary. In process 610, the client or other user may also view miscellaneous or errata information. The client or other user may also access, in process, 615, any advance directives, living wills, corrections to records, or dental or optical records or data.

To aid the client in preparing for a physician visit, the CMRS may provide, in process 617, instructions and checklists related to what a client should do to prepare for various healthcare encounters. For example, the CMRS may provide instructions for preparing for a visit to a specialist, preparing for a visit to a hospital for surgery, preparing for a visit to a physician for a second opinion, and preparing for a visit to the client's primary care physician.

FIG. 7 is a flow diagram illustrating an overview of a method of providing a centralized medical history in accordance with another embodiment of the invention, and FIG. 29 is a flow diagram illustrating an overview of a method of providing a centralized medical history in accordance with another embodiment of the invention.

Figure 31:
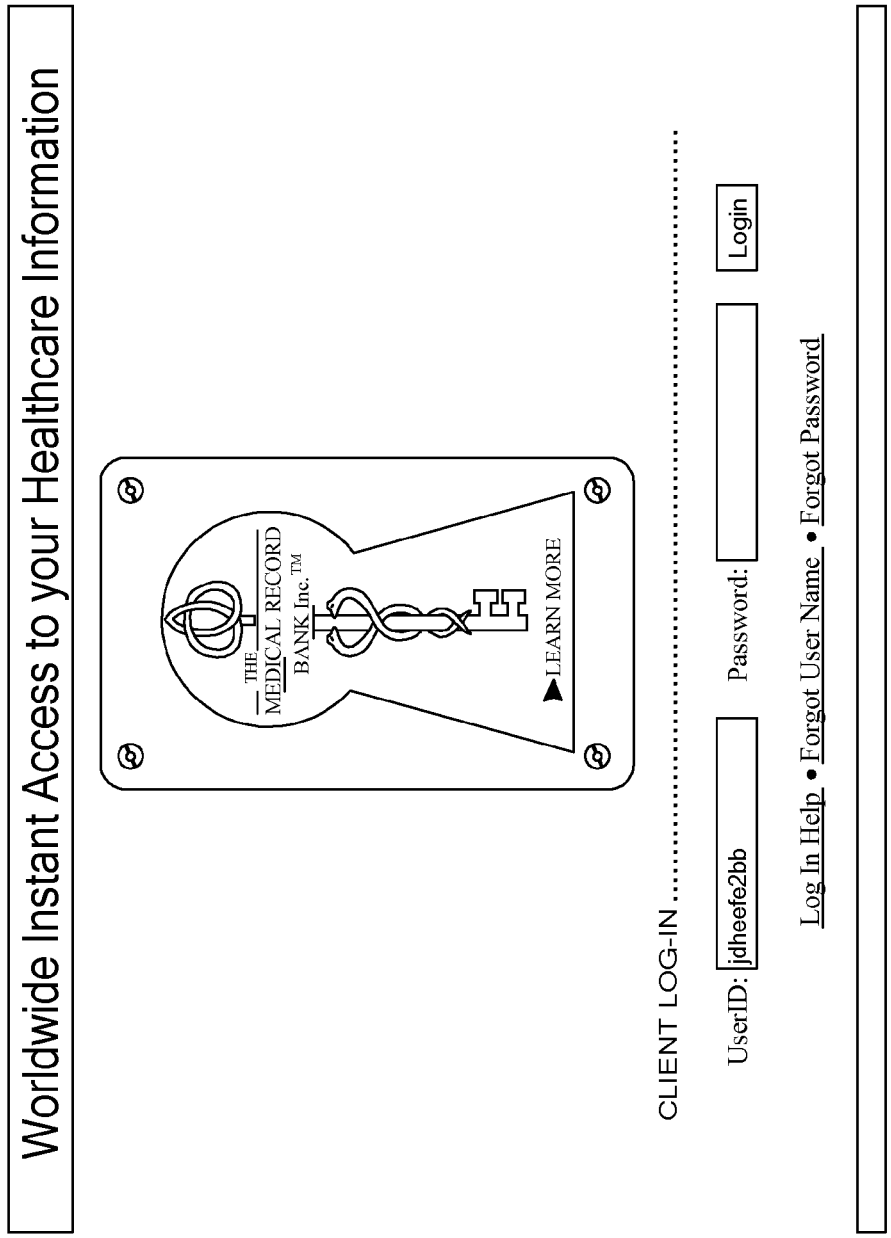
FIG. 31 is an illustration of a web page for providing a centralized medical history in accordance with the embodiment of FIG. 30.

FIG. 30 is a flow diagram illustrating an overview of another method of providing a centralized medical history in accordance with another embodiment of the invention. In accordance with the embodiment of FIG. 30, a client registers with a CMRS service provider over a computer network via a registration process described below. Again, the client may register via one or more graphical user interfaces which may be a series of web pages associated with a website of the CMRS service provider such as the web page illustrated in FIG. 31 and the software associated with the CMRS service will create a client homepage and create and begin processing an emergency card to be sent to the client. From the client homepage, the client may create and maintain a his or her account, create and access a critical health information summary and client diary, make arrangements to collect medical data and records (which will be scanned by the CMRS service provider), review and label the medical data collected, record client comments related to the medical data, and retrieve medical data in preparation of healthcare encounters.

In accordance with the embodiment of FIG. 30, the client accesses the home page of the CMRS service provider and chooses from navigation options provided by the CMRS (such as the "Sign Up Now" hyperlink discussed above). The client may then navigate, via hyperlinks, to another web page, whereby the client is provided with general information regarding how the CMRS service works. The client may then be provided with one or more web pages whereby the client may view a client agreement. Such an agreement (or contract) may include a fee schedule, descriptions of services, description of client obligations, etc. Upon acceptance of the agreement (e.g., by clicking on a hyperlink labeled "accept"), the client may proceed to payment for the CMRS service. Payment for the CMRS service may be processed using Verisign Payflo Pro which is accessed through the CMRS web site. During the payment process, client demographic data may be collected and used to populate the client's account.

In accordance with the embodiment of FIG. 30, the client will required to choose either an adult or a custodial account and parents will complete a custodial account for their children. If the client is a custodian her or she will click on a hyperlink that designates her as a custodian client and use one or more interfaces similar to that shown to enter data about herself or himself as well as data about his or her child or ward including the name, date of birth, etc. The CMRS service provider may poll the dates of birth of each child/ward and automatically notify the parent or guardian when a child/ward is approaching the age of 18. Again, an adult may establish several different types of accounts (one for herself, one for her child, one for her ward) if she so desires. If the client is setting up an adult account and the name on the account is different than the name on a credit card used for payment, the adult must enter data about him or herself (i.e., date of birth, e-mail address, telephone numbers, billing address, etc.).

The CMRS service provider processes the account order and generates an email to the client advising them of a primary username and password in which permits read and write access. Again, all emails to the client from the CMRS may feature a hyperlink to a CMRS web page. The CMRS service provider may poll existing system accounts daily to find client activation dates that indicate that the account is about to expire. (As above, in this embodiment, an account will last 12 months, thus the CMRS service provider will poll the system for client accounts that are 11 months old. For those accounts that are 11 months old, the CMRS service provider may send a renewal notification some time prior to the expiration date, here four weeks, so that a client may renew his or her account. In accordance with this embodiment, renewal will require the client to again agree to the terms of the client agreement. (Client accounts may also be renewed automatically using a feature of Verisign. That is, if the client does not terminate his or her account and if his or her credit card is valid, the account may be auto-renewed. In this case, the client may notified of any changes to the client agreement by e-mailing a new agreement to client and giving him or her an opportunity to terminate their accounts if the agreement is not acceptable.) The CMRS service provider tracks client accounts, membership terms, renewal dates and overdue accounts. The CMRS service provider may reserve the right to terminate client accounts that are a predetermined amount of time in arrears. In some cases, the CMRS service provider may permit continued access to the account without permitting additional updates of the account.

Figure 32:
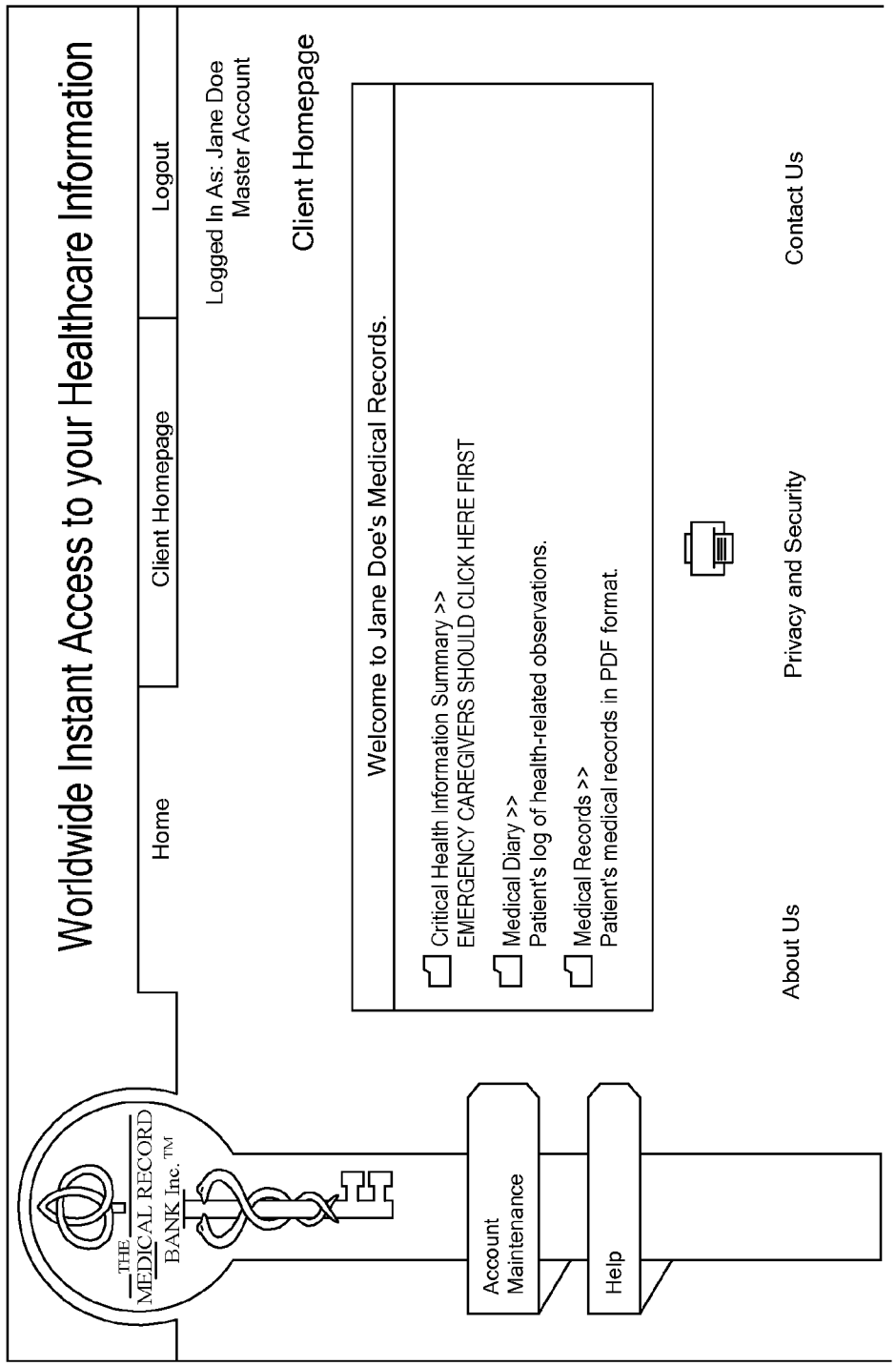
FIG. 32 is an illustration of a web page for providing a client homepage in accordance with the embodiment of FIG. 30.
Figure 37:
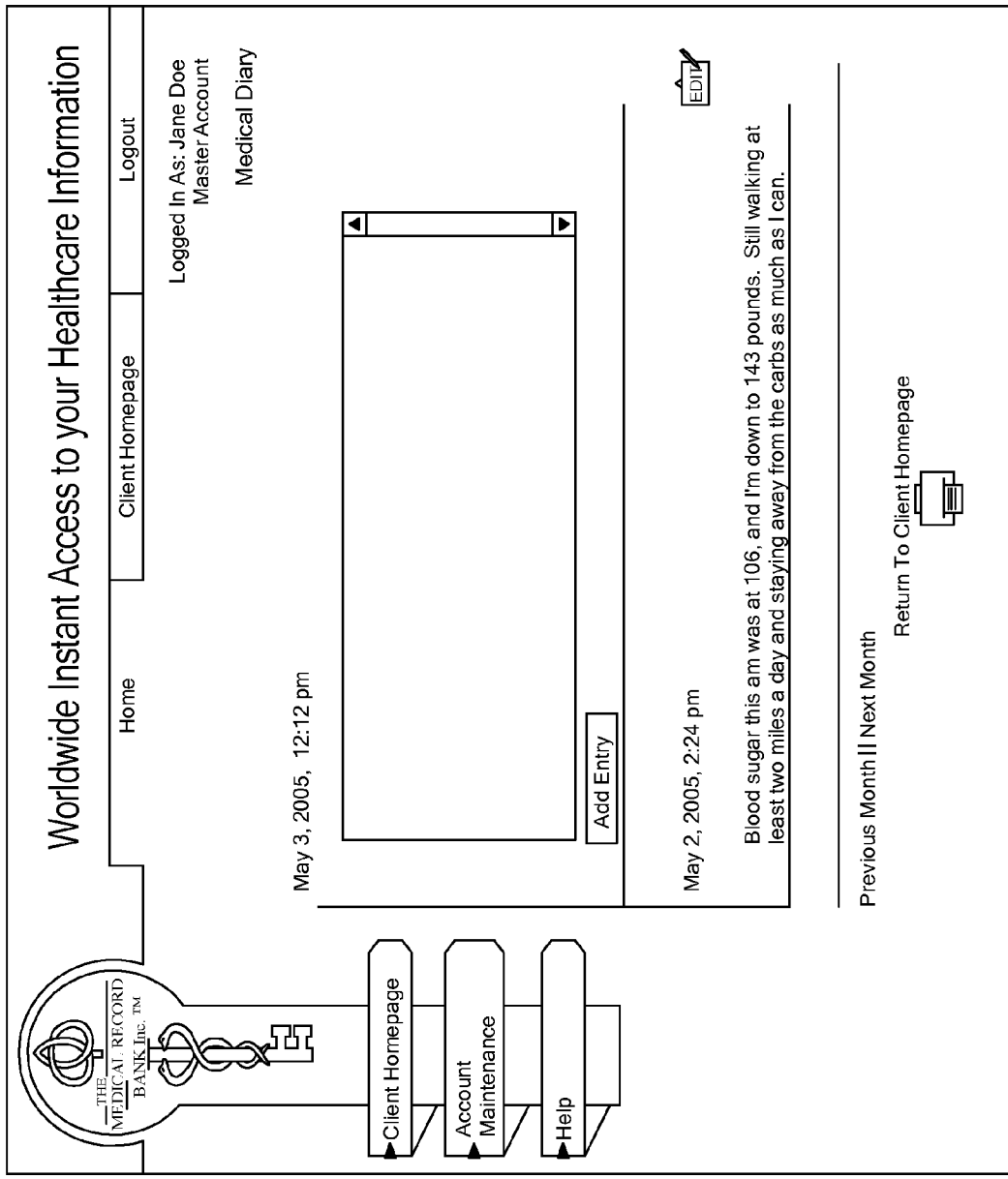
FIG. 37 is an illustration of a web page for providing a medical diary in accordance with the embodiment of FIG. 30.
Figure 38:
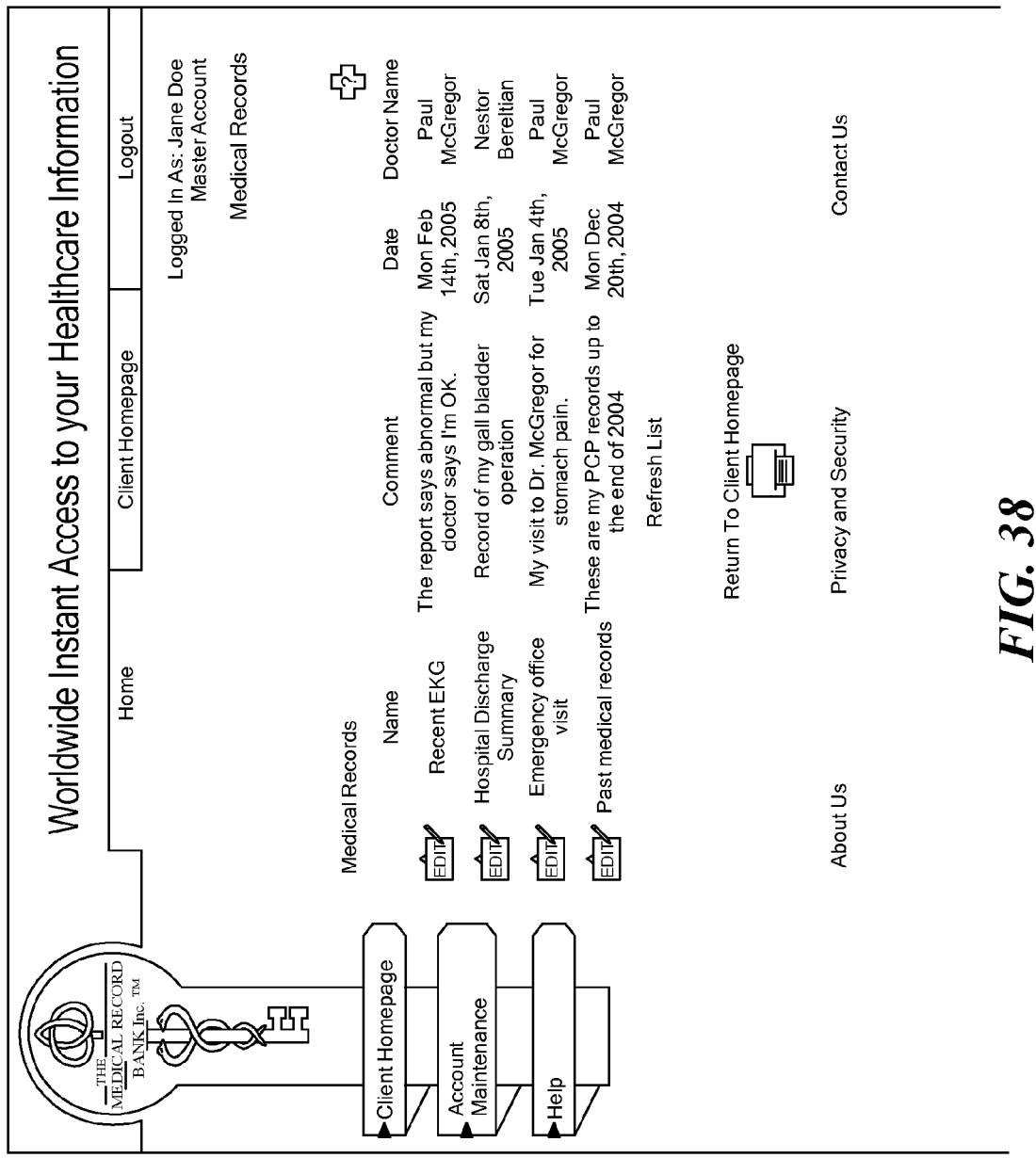
FIG. 38 is an illustration of a web page for providing medical records to a client in accordance with the embodiment of FIG. 30.
Figure 39:
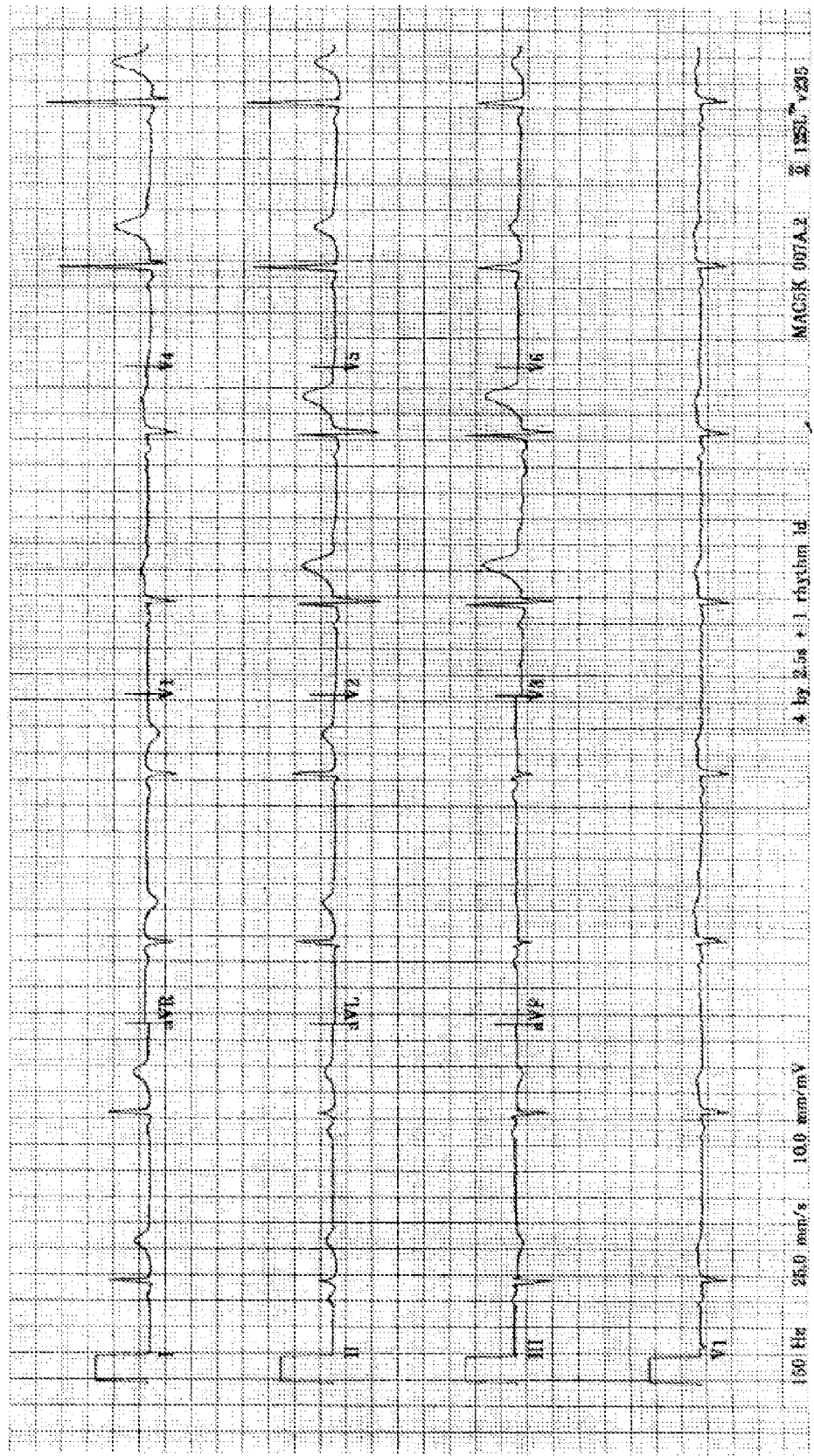
FIG. 39 is an illustration of an EKG record that may be accessed in accordance with the web page of FIG. 38.

The CMRS service provider creates a homepage for the client, such as the homepage illustrated in FIG. 32, whereby the client may access his or her critical health information summary (an example of which is illustrated in FIGS. 33-36), medical diary (an example of which is illustrated in FIG. 37), and medical data or records (such as the EKG shown in FIG. 39 accessed via a web page such as that illustrated in FIG. 38). The CMRS staff is notified that an emergency card should be created and mailed to the client. The emergency card may be a wallet sized card that features a secondary CMRS password that permits access to the client's record in case of a medical emergency but does not allow the user edit the record. The emergency card is mailed to the client with instructions associated with emergency card use.

The client is also asked to email the CMRS service provider to confirm that the client has received his or her emergency card. In accordance with this embodiment, the emergency card is sent inactive and the client must activate it by going into their account with the primary username and password set, going to the account maintenance folder and clicking on the emergency card maintenance folder. There they can activate their new card and/or terminate an old card, and or order a new card. When a new card is activated the old card is automatically inactivated unless the client had previously inactivated the card. FIGS. 85-89 are illustrations of web pages whereby a client may maintain, order, activate and de-activate an emergency access card in accordance with the embodiment of FIG. 30.

Figure 70:
Figure 71:
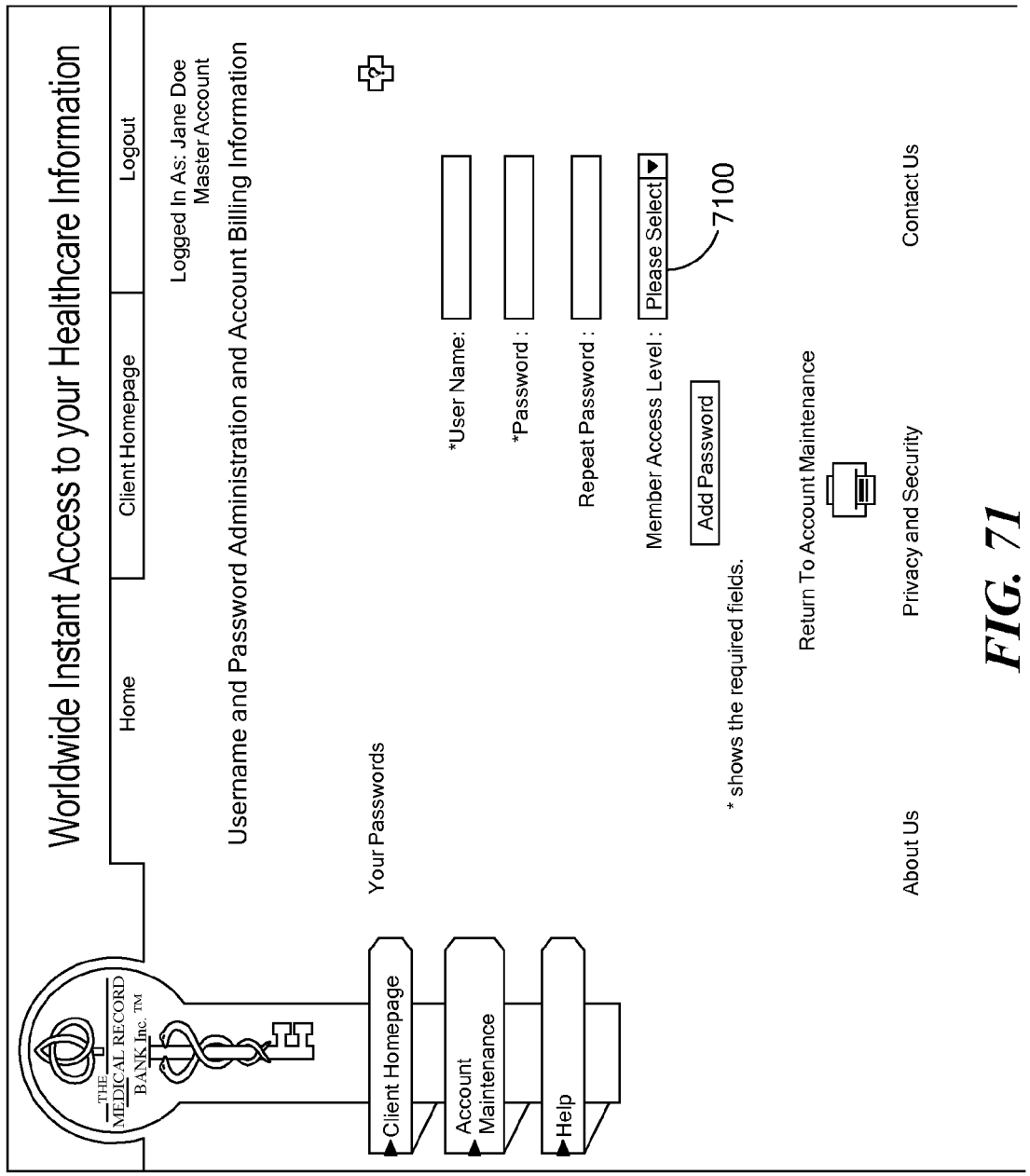
FIG. 71 is an illustration of a web page for adding a new user name and password in accordance with the embodiment of FIG. 30.
Figure 72:
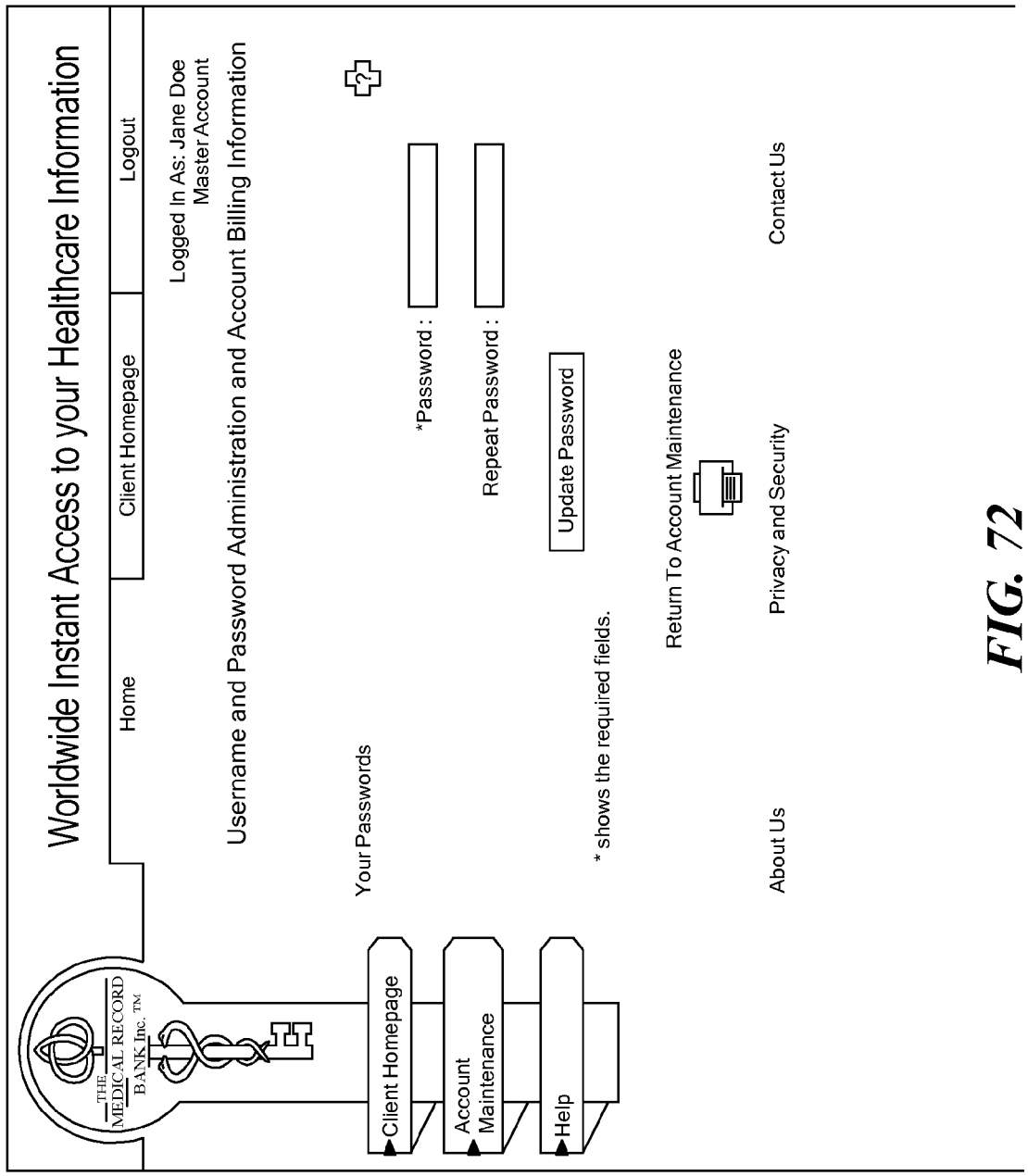
FIG. 72 is an illustration of a web page for editing a user name and password in accordance with the embodiment of FIG. 30.

FIGS. 69-70 are illustrations of a web page for creating and maintaining one or more user name and password sets in accordance with the embodiment of FIG. 30. Note that the client authorizes the password sets as well as the access to that each password set provides. For example, FIG. 71 is an illustration of a web page for adding a new user name and password in accordance with the embodiment of FIG. 30. In accordance with FIG. 71, the client may use the pull down menu 7100 to select the access he or she wants the username and password set to supply. Access options associated with the pull down menu may include "read only" (or "record reader"), "read and write" (or "master"), etc. FIG. 72 is an illustration of a web page for editing or updating a username and password in accordance with the embodiment of FIG. 30.

The CMRS may generate an email a predetermined amount of time after mailing out the emergency card, such a one week later, advising the client to confirm receipt of his or her emergency card or to contact the CMRS service provider if the card was not received. If a client loses his or her emergency card, the CMRS service provider may, upon notification of the loss, provide are placement card.

Figure 43:
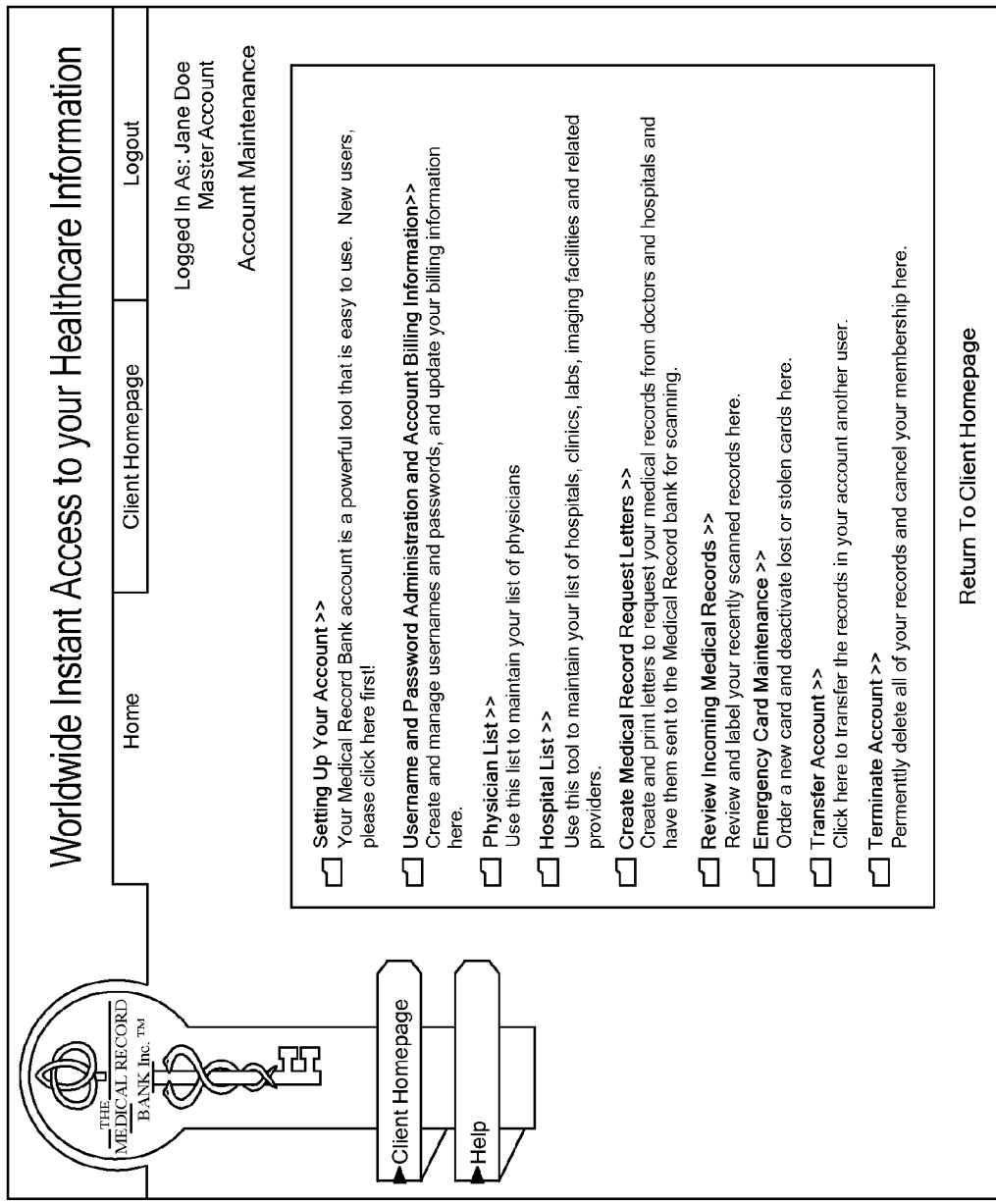
FIG. 43 is an illustration of a web page for allowing a client to maintain an account in accordance with the embodiment of FIG. 30.
Figure 44:
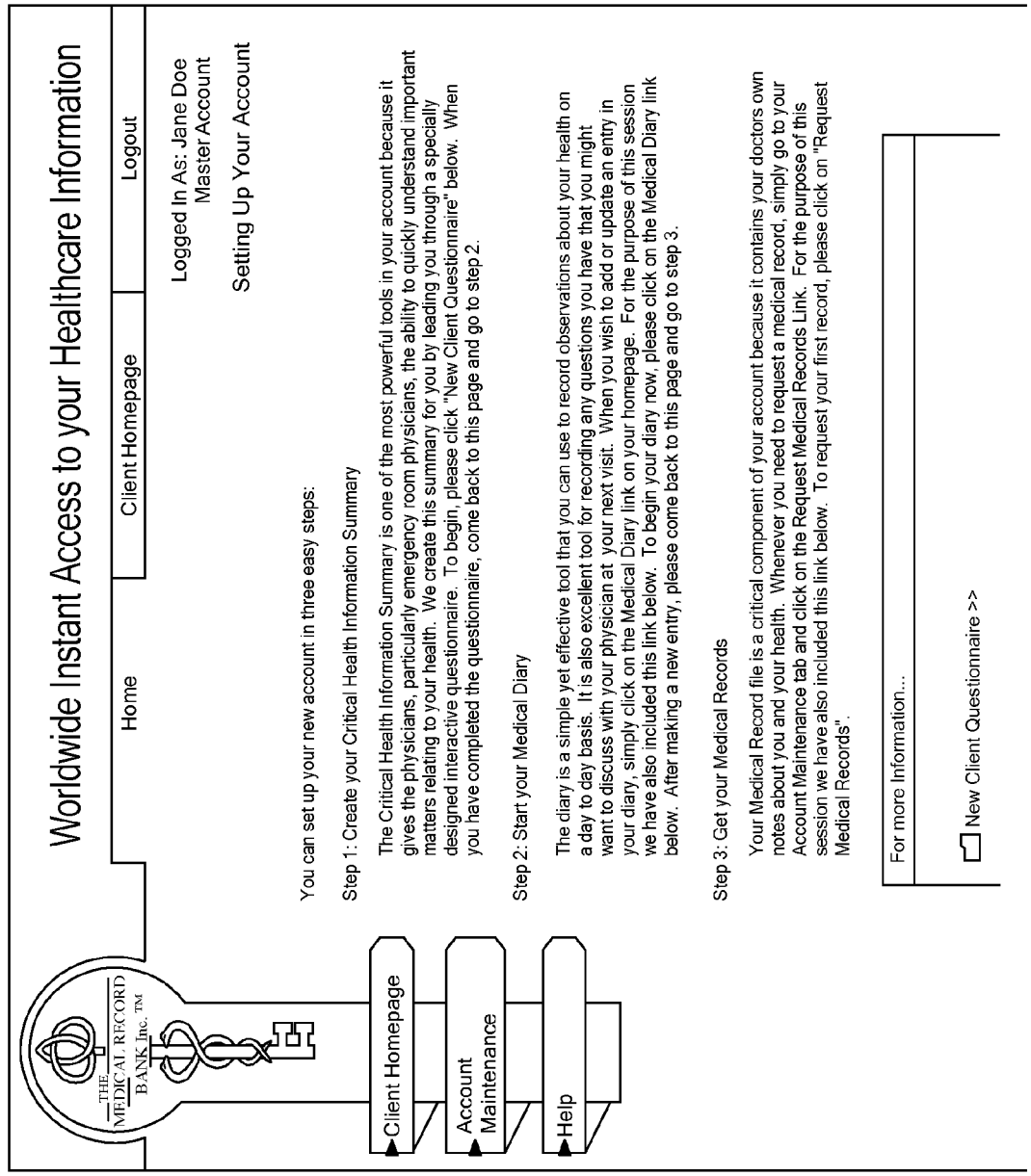
FIGS. 44-45 are illustrations of a web page for allowing a client to set up an account in accordance with the embodiment of FIG. 30.
Figure 45:
Figure 49:
Figure 58:
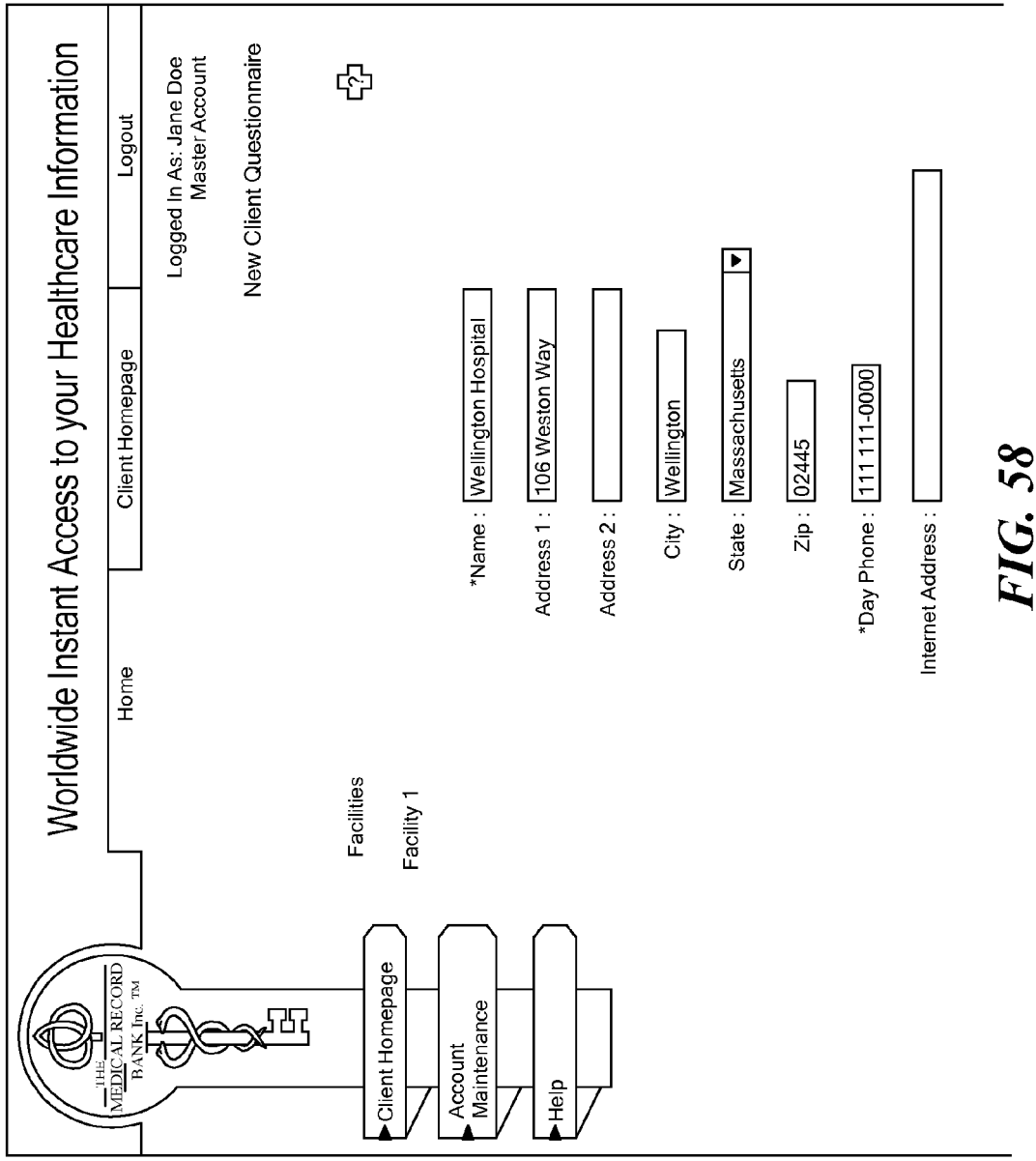
Figure 60:
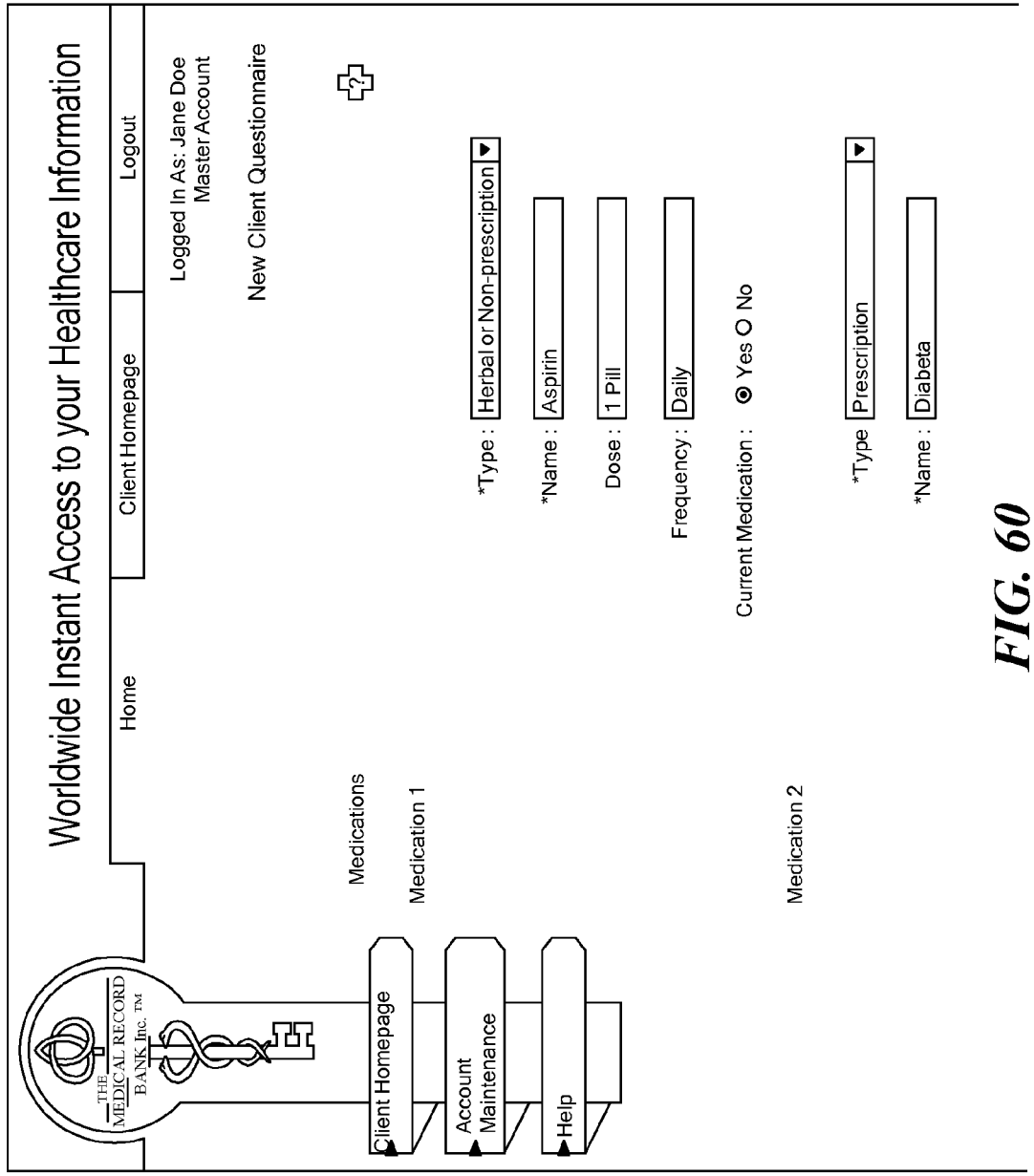
Figure 64:
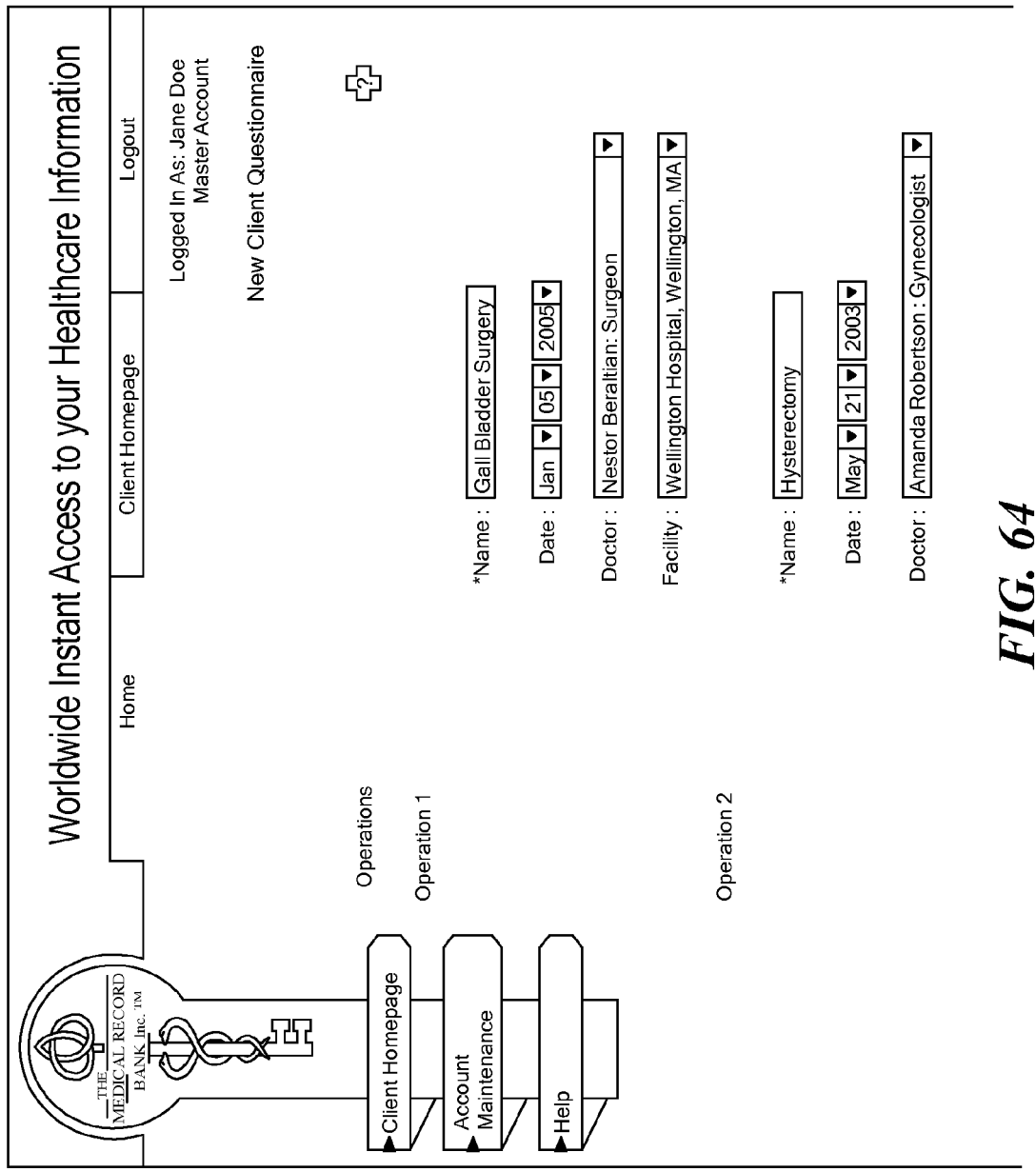
Figure 66:
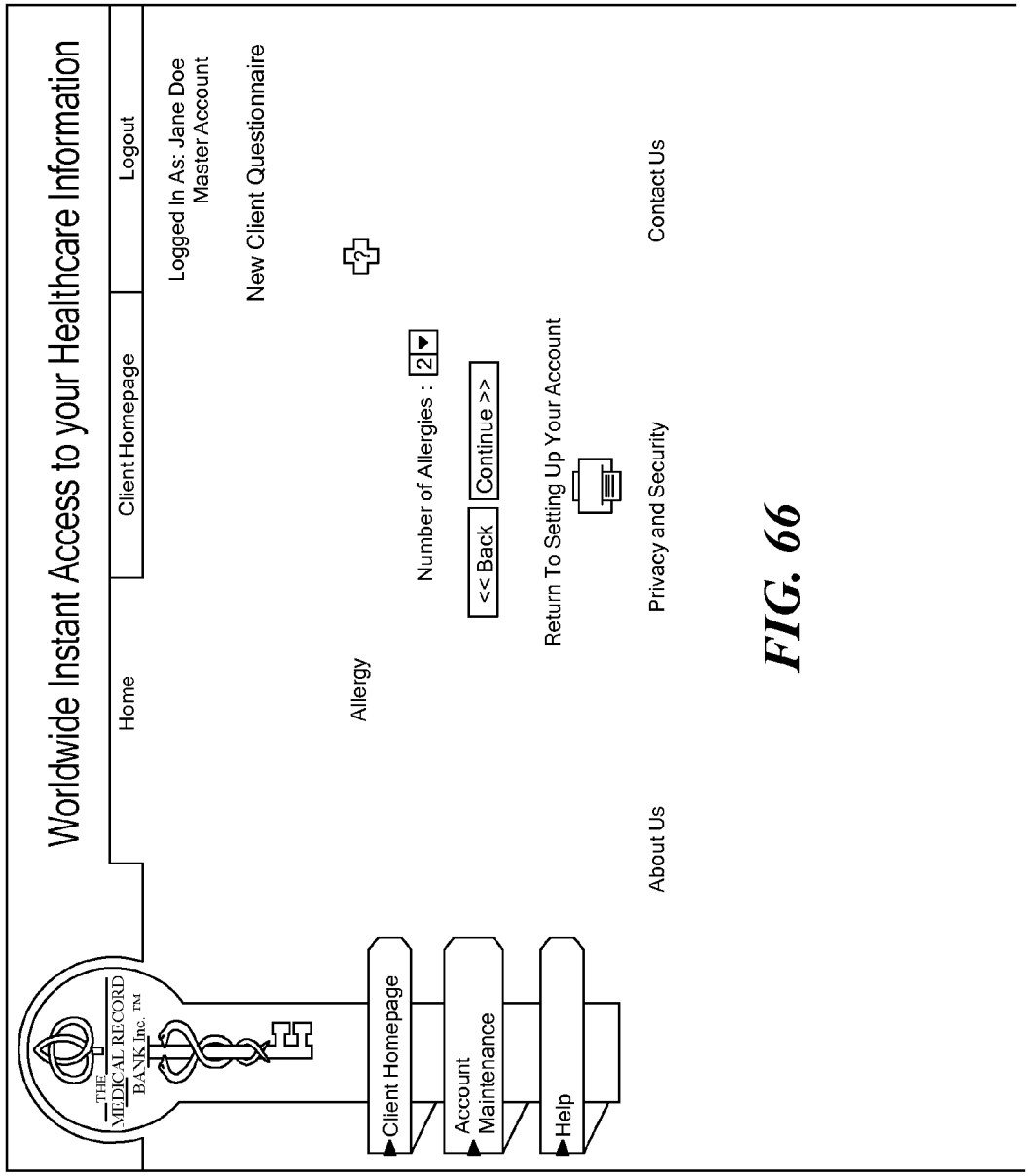
Figure 67:
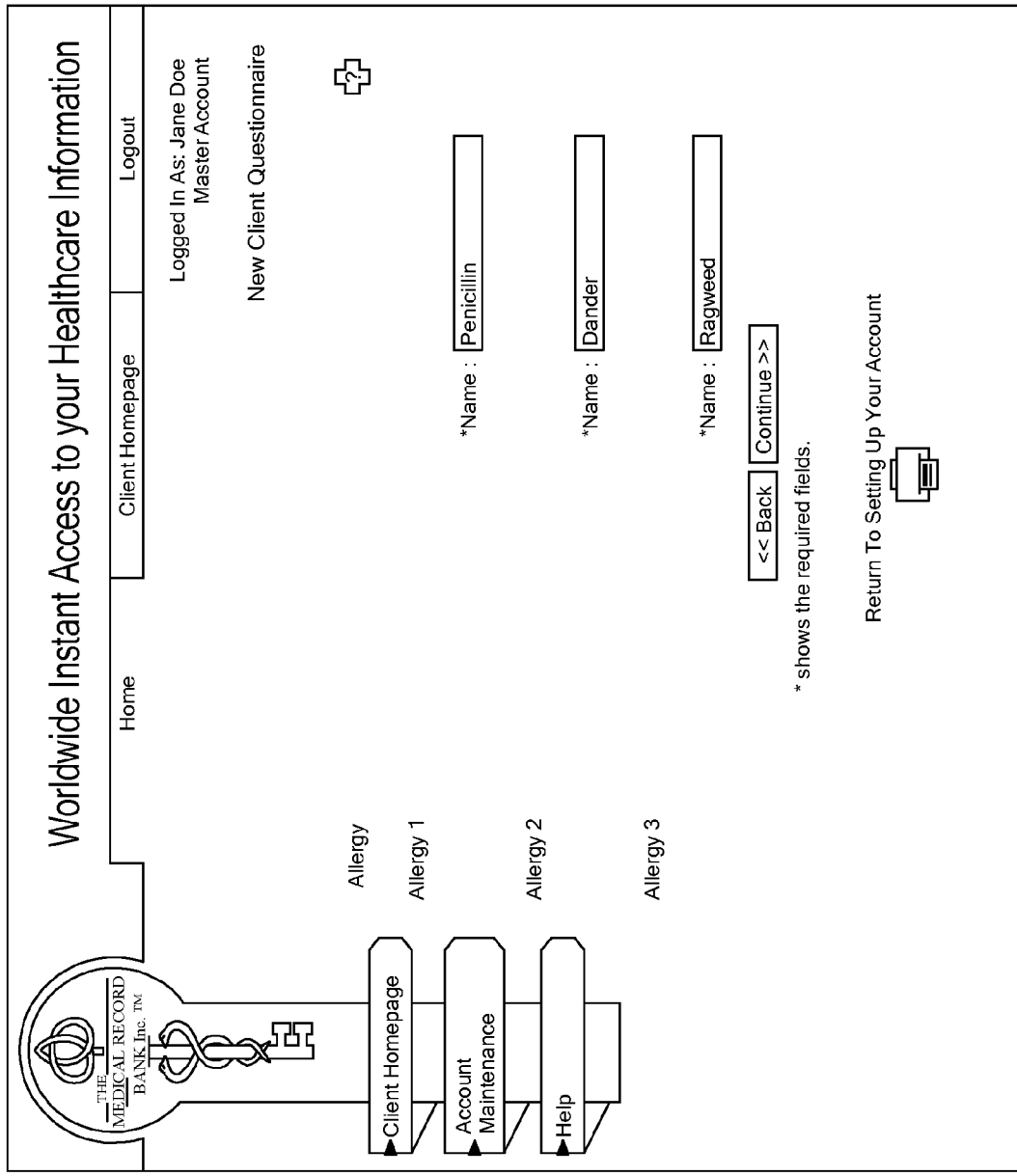

The client creates and maintains an account via the CMRS. In accordance with the embodiment of FIG. 30, the client may set up or create and maintain an account by accessing an account maintenance module via a web page as shown in FIG. 43. FIGS. 44-45 is an illustration of a web page whereby a client may set up an account. To set up an account, a client fills out a new client questionnaire (accessed via a web page such as that shown in FIG. 46). An example of a new client questionnaire is shown in FIGS. 47-68. Once the new client questionnaire is completed and submitted, a critical health information summary (such as, for example, the critical health information summary shown in FIGS. 33-36) is generated by the CMRS based on the data collected in the questionnaire.

The account maintenance module may provide the client with an on-line tutorial that includes instructions related to use of the CMRS system, access to the CMRS system, information regarding medical emergencies, information regarding mining or searching a medical history, information regarding labeling medical data, and procedures for using the medical diary (or a disease-specific on-line diary). Procedures and tools for collecting medical records and data and updating medical records and data are also provided by the account maintenance module. These may include procedures for securing data from primary care physicians, specialists, hospitals and clinics. Procedures and tools for emergency card maintenance, billing, account transfers, password maintenance and account termination (see FIG. 43) may also be provided.

Figure 74:
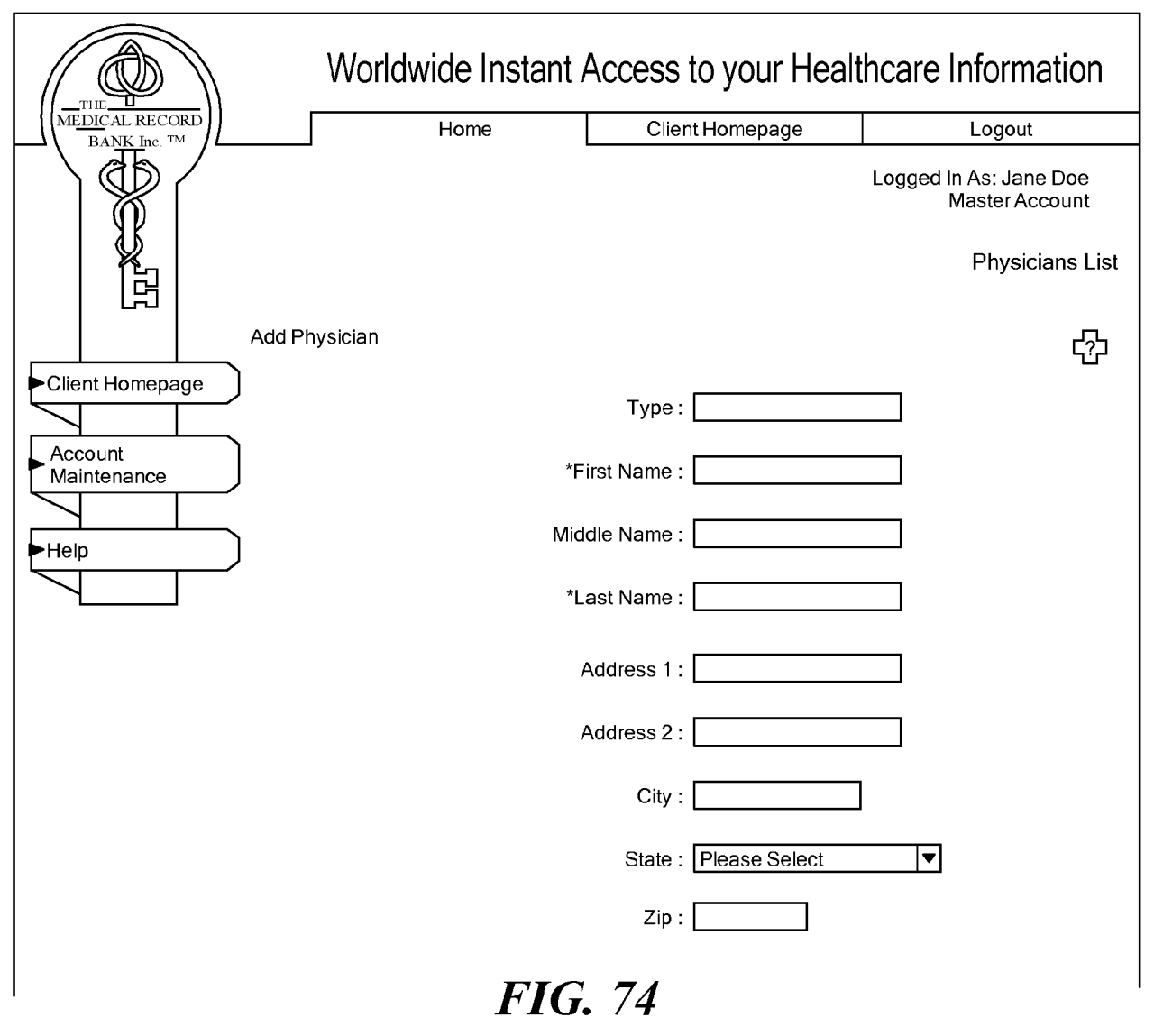
Figure 75:
Figure 77:
Figure 78:
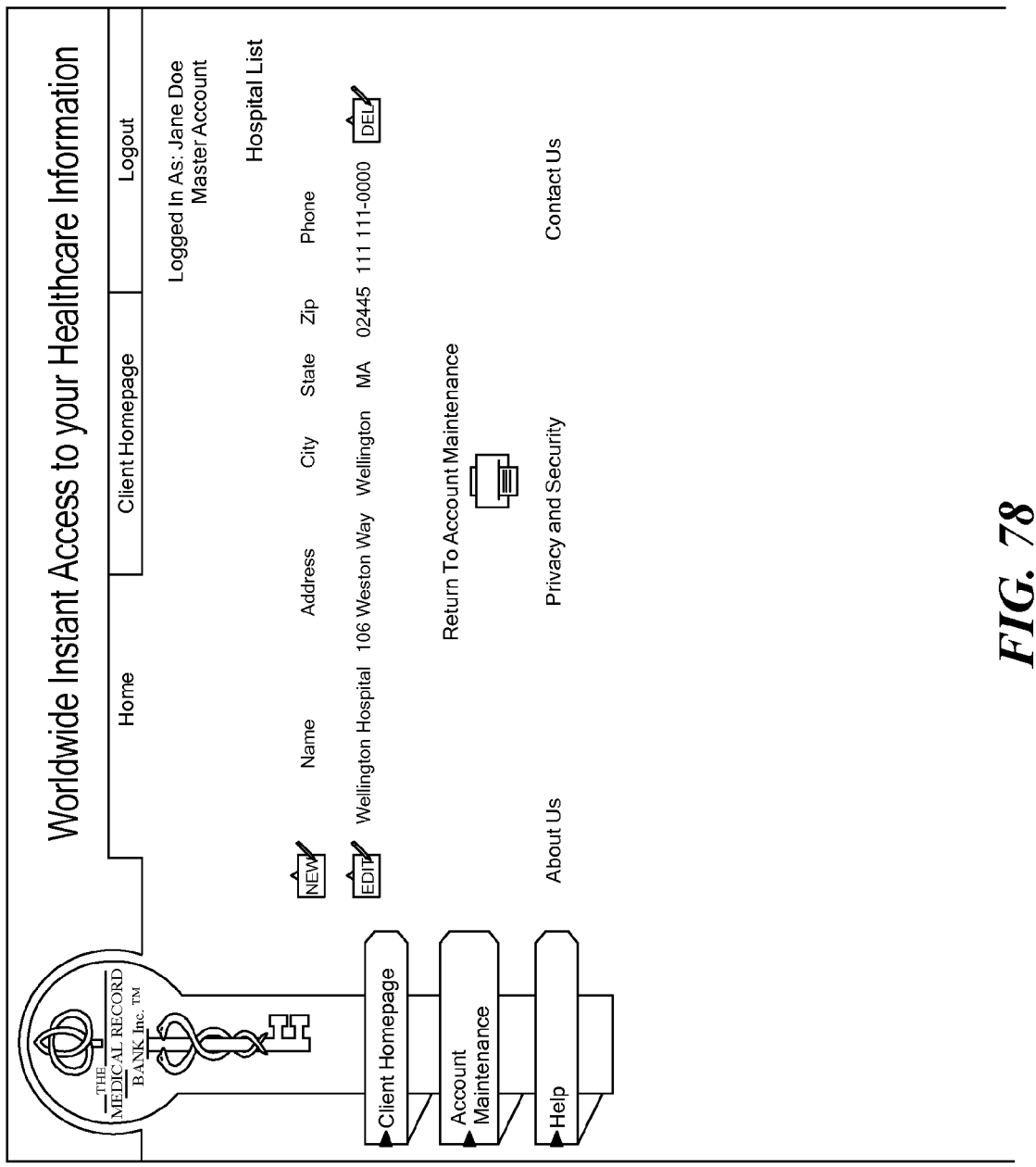
FIGS. 78-79 are illustrations of web pages for creating and maintaining a facility list in accordance with the embodiment of FIG. 30.
Figure 79:

Further, via the account maintenance module the client may create and maintain a physician of healthcare facility or entity list as illustrated in FIG. 73. FIGS. 74-75 is an illustration of web page for adding a physician to the physician list. FIGS. 76-77 is an illustration of a web page for editing physician information associated with the list and FIGS. 78-79 are illustrations of web pages for creating and maintaining a facility list.

Physician and hospital finder tools may be provided via the account maintenance module, as well as hyperlinks that allow clients to connect to state boards of medicine and search for the address of former physicians. Procedures for sending client medical records and data to the CMRS service provider and for using a record submission form may be provided. For example, clients may submit any medical records or data that the client has collected (in, for example, in a file called a "safety deposit box") for scanning by the CMRS service provider. To submit such data in the form of one or more page documents, the document may be accompanied by a CMRS record submission form. As mentioned above with respect to FIG. 3, the form may require the client to provide a page count and identification of a file (such as hospital record, physician office record, etc.) that the client wants the document to be stored in. The record submission form may also be scanned as a cover page of the document.

The CMRS service provider may also provide letter templates (or letters that are generated automatically subsequent to identification of the recipient) for the client to use to initially request that medical data be forwarded to the CMRS service provider. As noted above, a letter template may cause the letter to be imprinted with a machine readable code identifying at least the client. The code may in addition, or in the alternative, identify the source of the medical data. Such letter templates may include code which may be scanned, such as bar code, which identifies the client, the health care entity, the letter, the purpose of the letter, the contents of the letter or other information associated with the letter.

Figure 80:
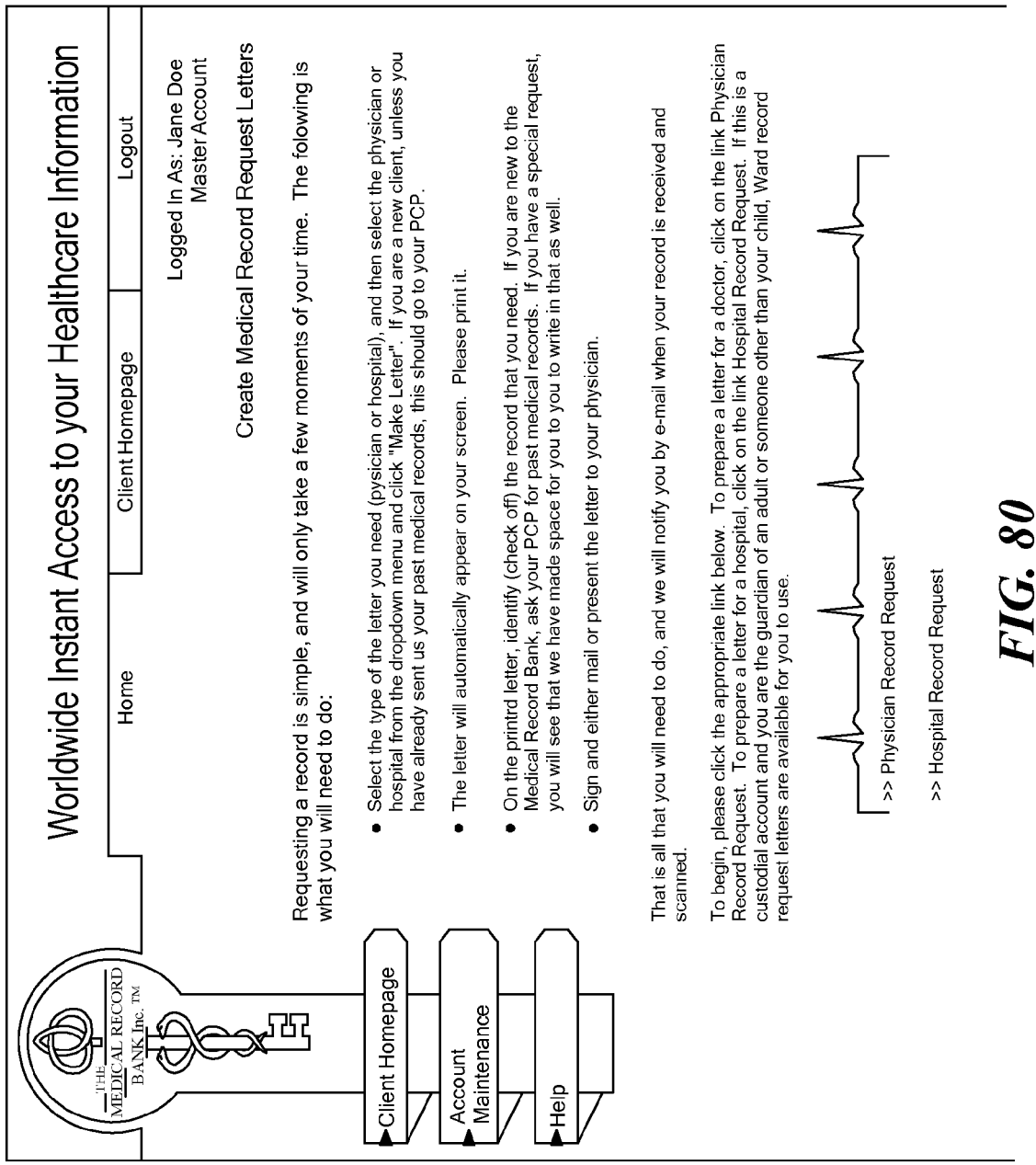
FIGS. 80-82 are illustrations of web pages for creating medical record request letters in accordance with the embodiment of FIG. 30.
Figure 81:
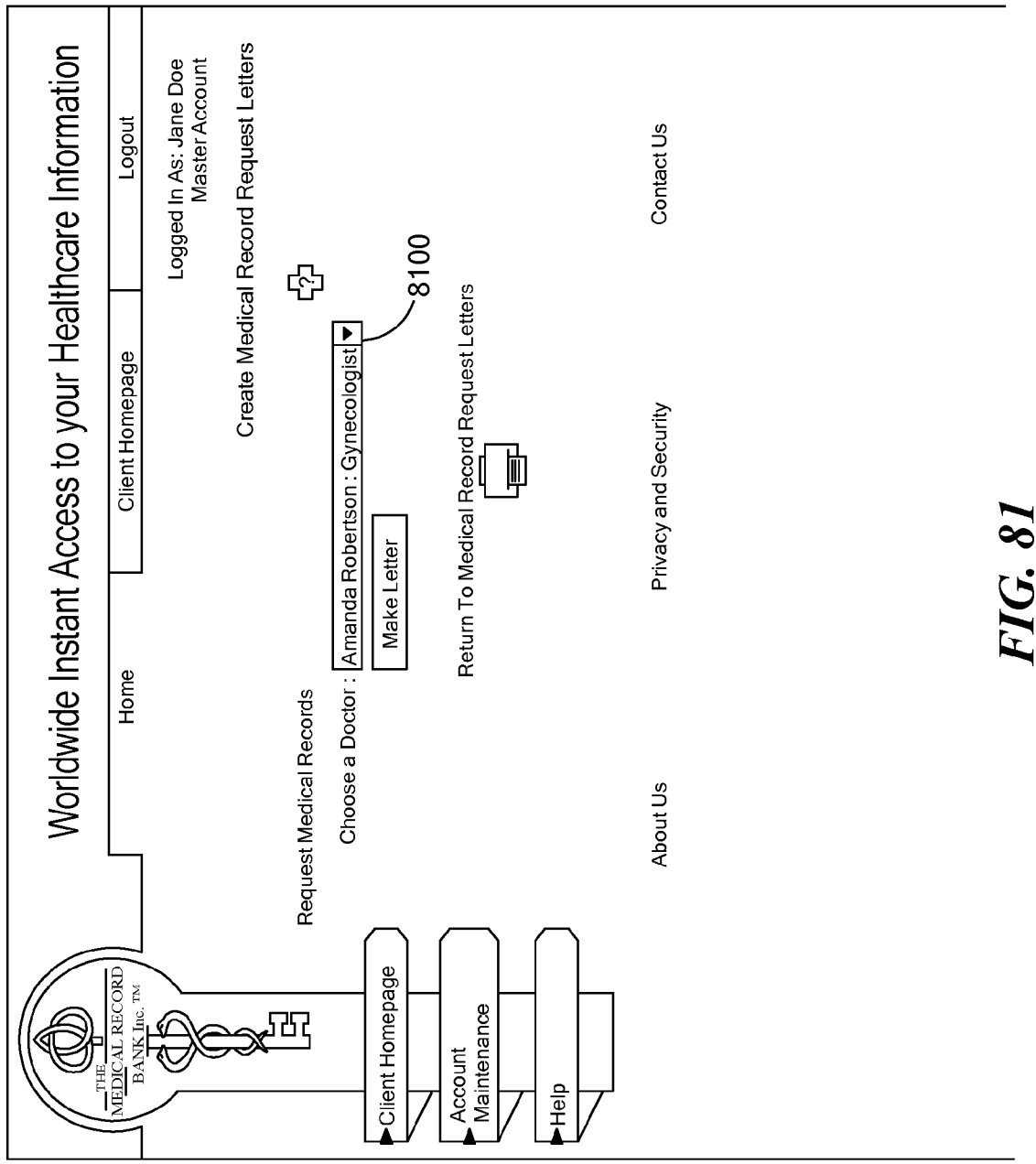
Figure 82:
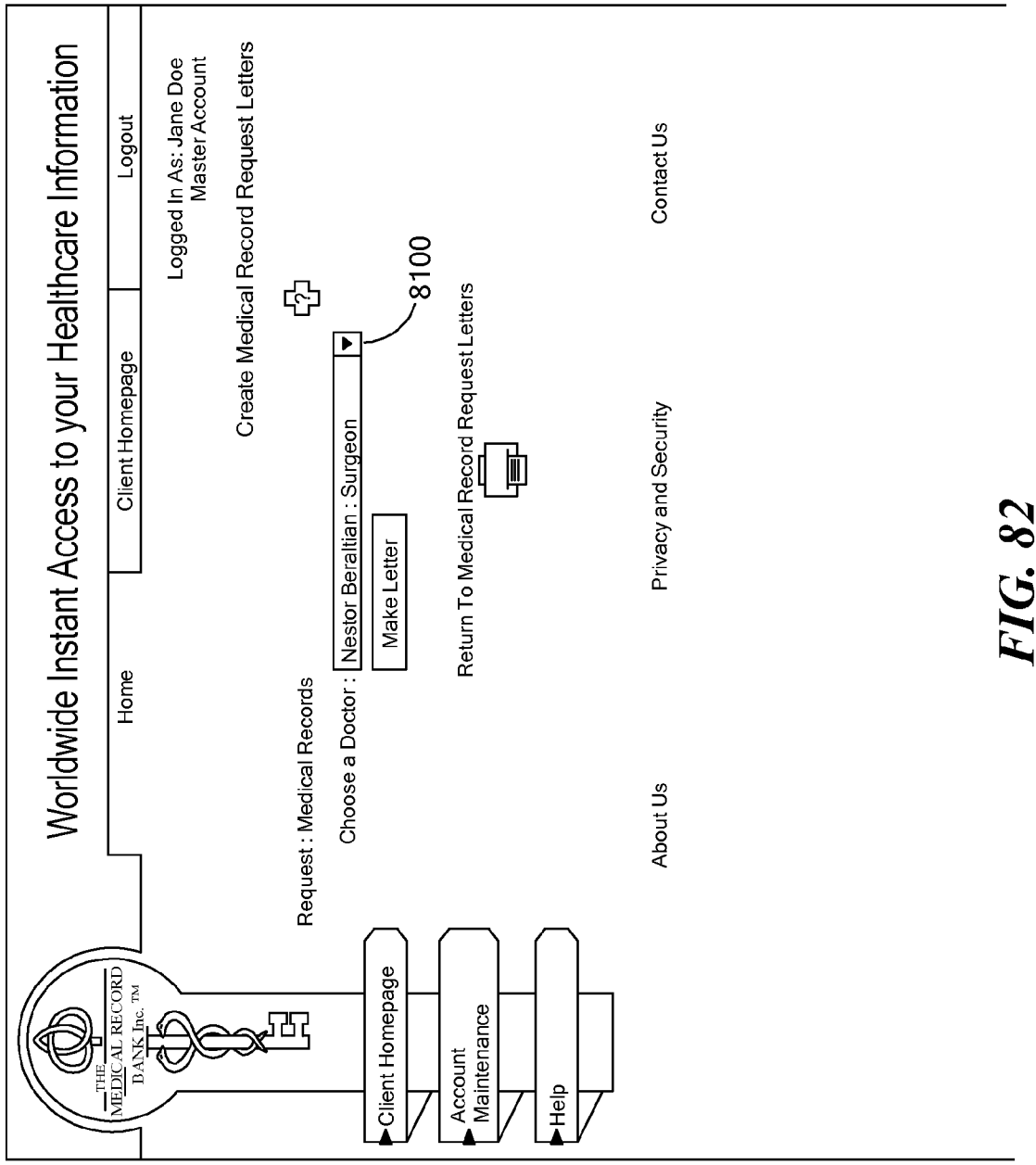

FIGS. 80-82 are an illustrations of a web pages whereby the user may access and/or create a record (or medical data) request letters in accordance with the embodiment of FIG. 30. Physician and hospital information captured in the online questionnaire that the client completes when they open their new account is stored and once that information is in the system, the client simply has to choose a recipient physician or healthcare facility or entity form a drop down menu 8100. The CMRS populates the letter with a unique client identifier and appropriate information for the client, be it an adult, or child/custodial account. A letter to that physician or healthcare facility or entity is automatically generated by clicking on an appropriate link (here the "Make a Letter" link). The client may then print the letter out, sign it and mail it to the physician or facility. FIG. 83 is an illustration of a letter automatically generated by the CMRS requesting medical data from a physician. The recipient may be directed to send record(s) to client Care Of the CMRS.

Figure 84:
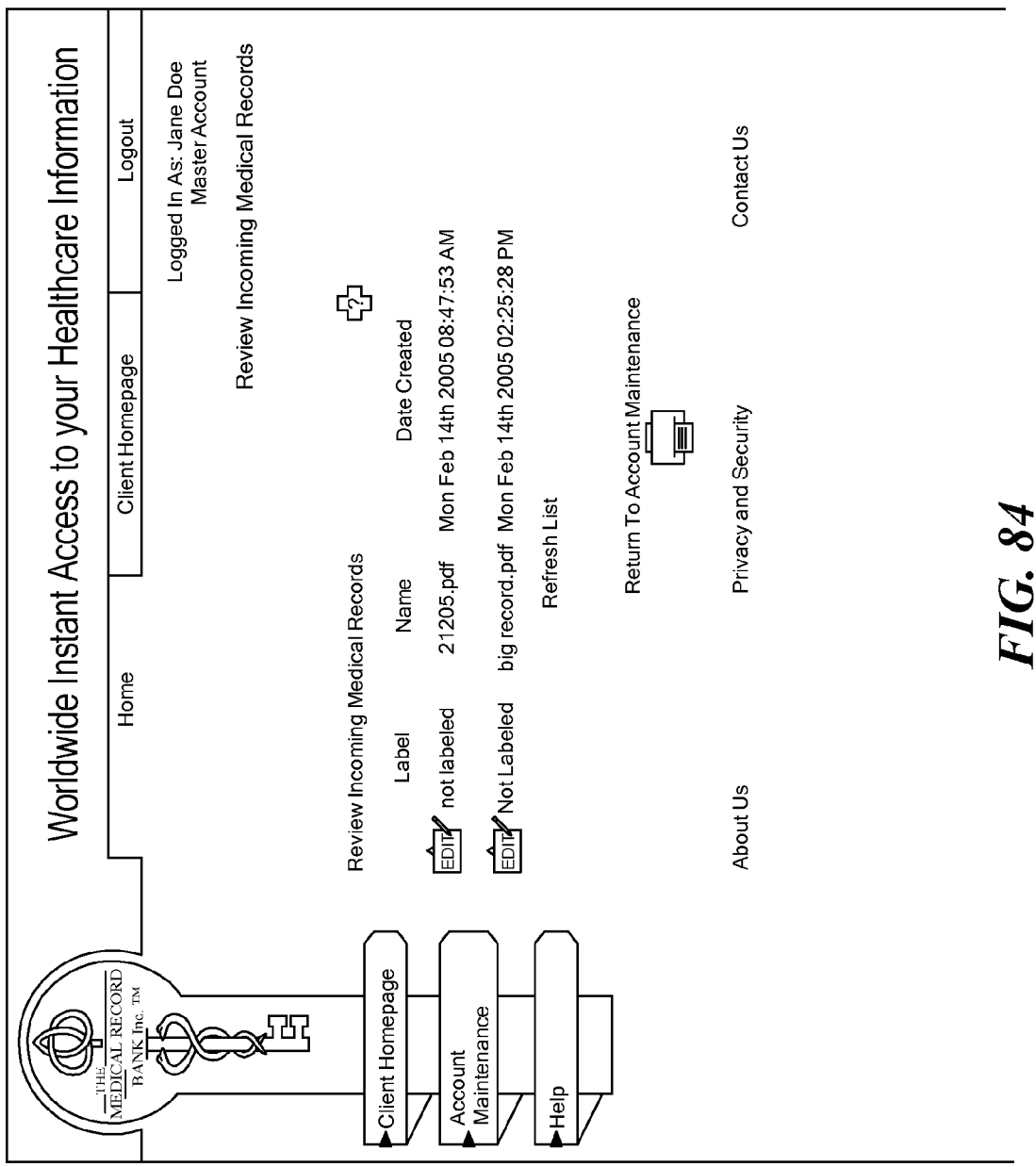
FIG. 84 is a an illustration of a web page whereby a client may review and notate incoming medical records in accordance with the embodiment of FIG. 30.
Figure 85:
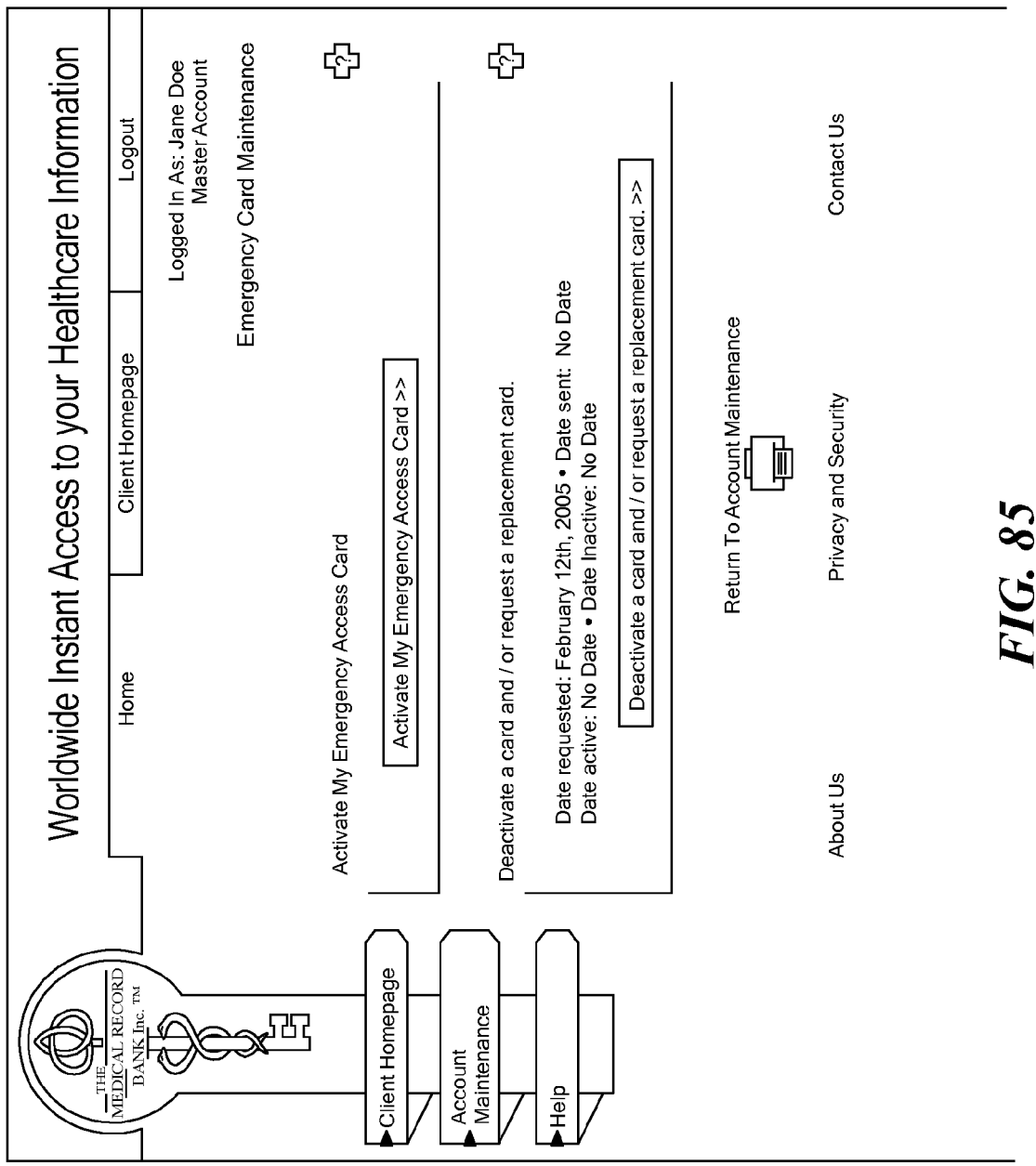
Figure 86:
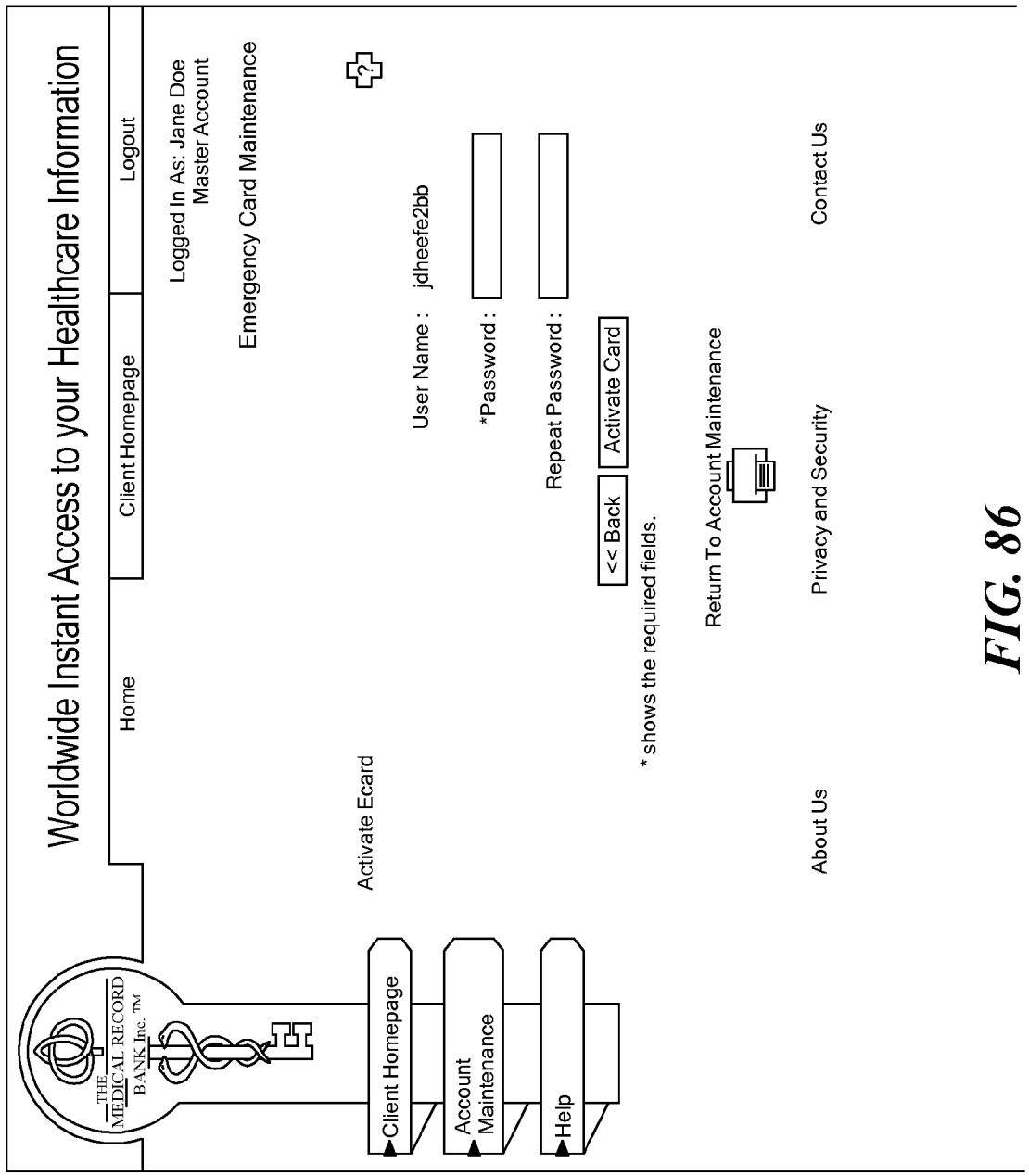
Figure 89:

Medical records and data are received by the CMRS service provider. The client's name and identifier number are noted from the mailing package or from client's email. Pages of documents containing the medical records or data are counted manually or mechanically and scanned. The scanned page count is compared or matched with the page count of the document prior to scanning and the pages are inspected visually for focus and alignment. If necessary, the pages may be re-scanned. The scanned pages are placed in a folder identified as the "review incoming medical records" folder and may be labeled with a scan date and/or time and/or other pertinent information. FIG. 84 is an illustration of a web page whereby a client may review, notate and label incoming medical data or records. Incoming medical data or records may be reviewed by the client using only the primary read/write username and password set.

Figure 40:
Figure 41:

FIGS. 40-42 are illustrations of web pages whereby a client may edit a notation to, label of or comment on medical data and review, accept or reject a medical record or data in accordance with the embodiment of FIG. 30. If a client rejects medical data, he or she may be asked to explain why they are rejecting the record. The CMRS service provider may review rejections to ensure that a mistake has not been made. Note, that in accordance with this embodiment, any medical data or record not approved by the client is not moved from the "review medical record folder" to the medical record and is thus not visible to a user with read only access.

Again, an email is sent to the client whereby the client is notified of a medical record update. The client may click on a hyperlink in the email to view the updated information. Upon viewing the updated information, the client may opt to review, reject, or accept the data (as shown in FIGS. 40-42). If the client chooses to review the data, the data stays in the review file. If the client chooses to reject the data, data or record is deleted and the CMRS service provider receives an error report complete with the client's reason for rejection. The CMRS operations staff may follow-up with the client if necessary. If the client chooses to accept the medical data, the client may be allowed a predetermined number of data/file scan(s) per year and the CMRS service provider may track the number of scans for each client.

The client may make notations or comments with respect to and/or label the updated information with the appropriate physician, hospital, laboratory, clinic or other name. During the labeling process, the client may be prompted by the CMRS to provide an online description of the medical record or data and a service date. After labeling and commenting is complete, the medical data or record is placed on the client homepage in the "medical records" folder or, alternatively, in the aforementioned safety deposit box. (For each record, the client, may be asked to identify the proper filing location, such as "medical record" or "safety deposit box." The client may then be prompted to date the document using a dropdown menu, name the document in an open text field, and enter the name of the physician associated with the data in another text field. The client may also be given an opportunity to comment on the record to draw attention to a part of it, or note something additional.

The medical records and/or data may be retrieved and prepared for healthcare encounters. A client may navigate through a medical history to retrieve medical records or data by accessing the CMRS homepage and choosing, navigation options. The client must enter a user name (such as a first initial, last name, and/or alphanumeric code) as well as his or her primary password (see FIG. 31). The client will be allowed access to his or her client home page such as the client home page illustrated in FIG. 32. The client may access an account maintenance file or folder via his or her homepage. Further, the CMRS service provider may provide a folder that allows a client to store any type of document he or she wishes to be included in the online file. Access to such a file may be provided to the client via the client's primary password. As mentioned above, the client may access other medical resources via his or her home page. When the client or other user accesses these resources, the CMRS may provide, physician and hospital finder tools, such as hyperlinks that allow the client or user to connect to state boards of medicine and search for information about physicians (such as a former physician's address). The CMRS may also provide links to foundations, associations and instructions relating to standards of care and treatment regimens.

Figure 90:
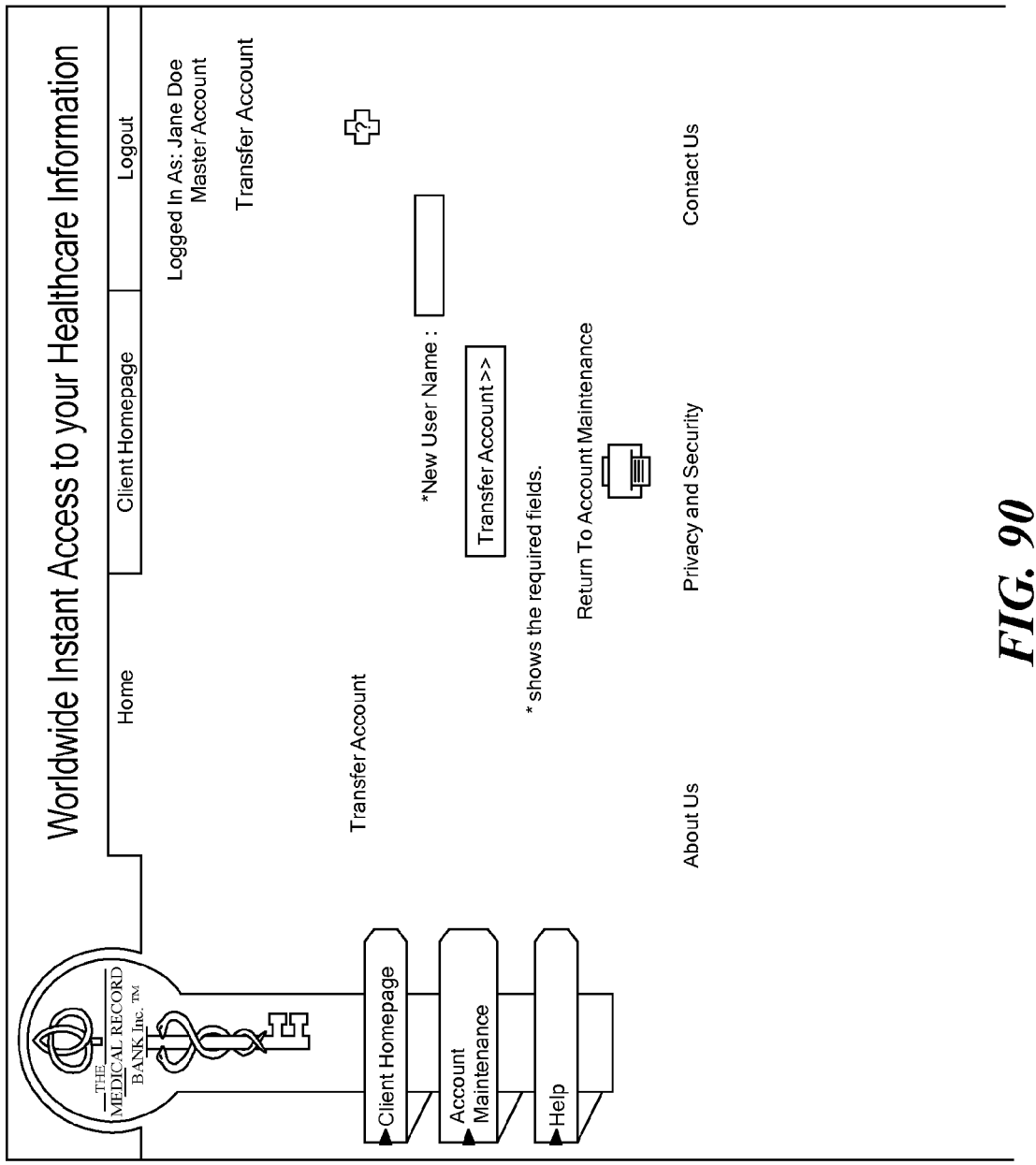
FIG. 90 is a an illustration of web page whereby a client may transfer an account in accordance with the embodiment of FIG. 30.

FIG. 90 is an illustration of web page whereby a client may transfer an account in accordance with the embodiment of FIG. 30. For example, if the child of a custodial client turns 18, the custodial client may transfer the child's medical data or record to an account that the (now adult) child has set up in the CMRS. The custodial client submits the new user account name created by the child via field 9001, clicks on the "transfer account" hyperlink and the child's new account will be populated with medical data and information once associated with the custodial account.

Figure 91:
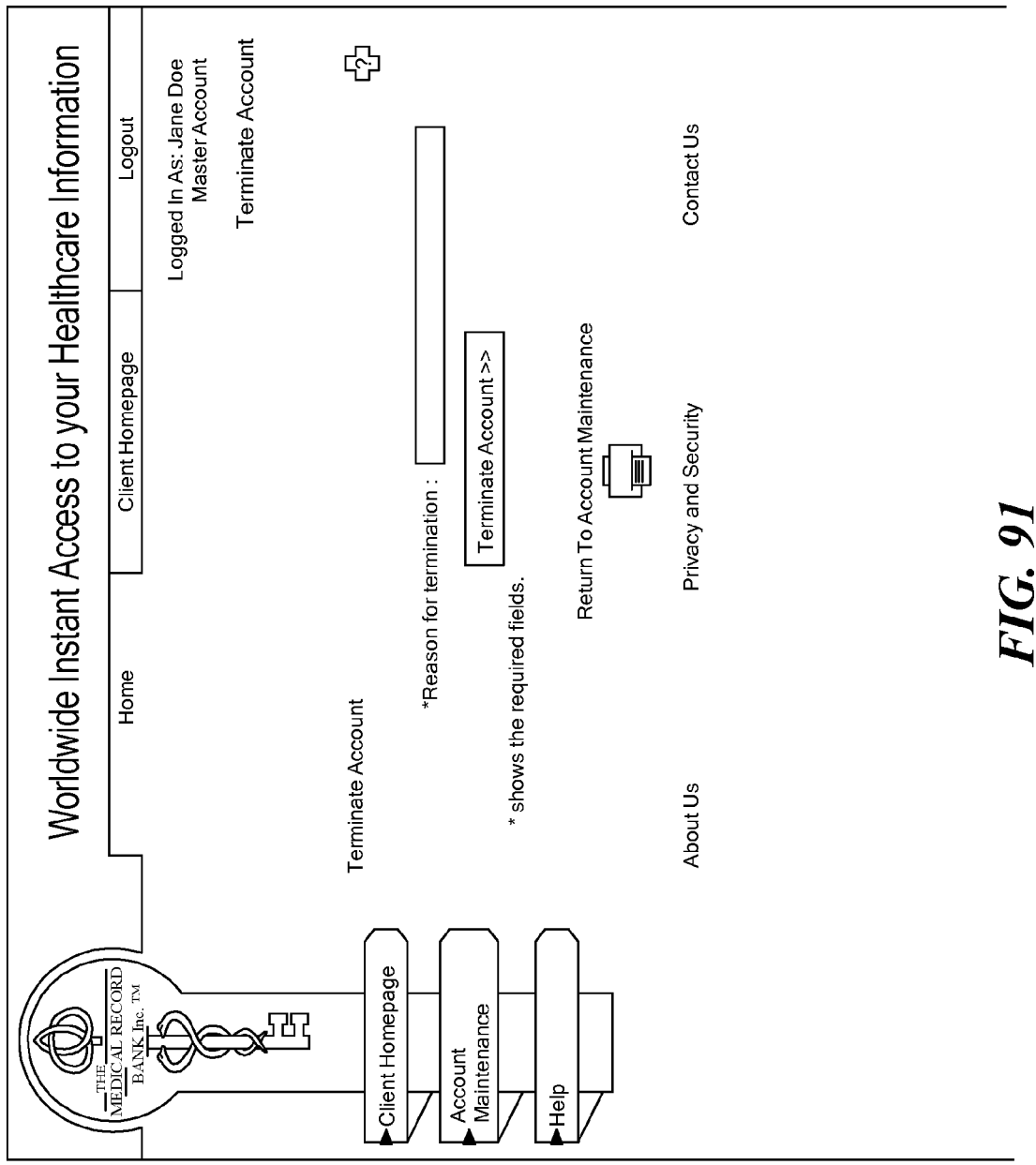
FIG. 91 is an illustration a web page whereby a client may terminate an account in accordance with the embodiment of FIG. 30.
Figure 92:
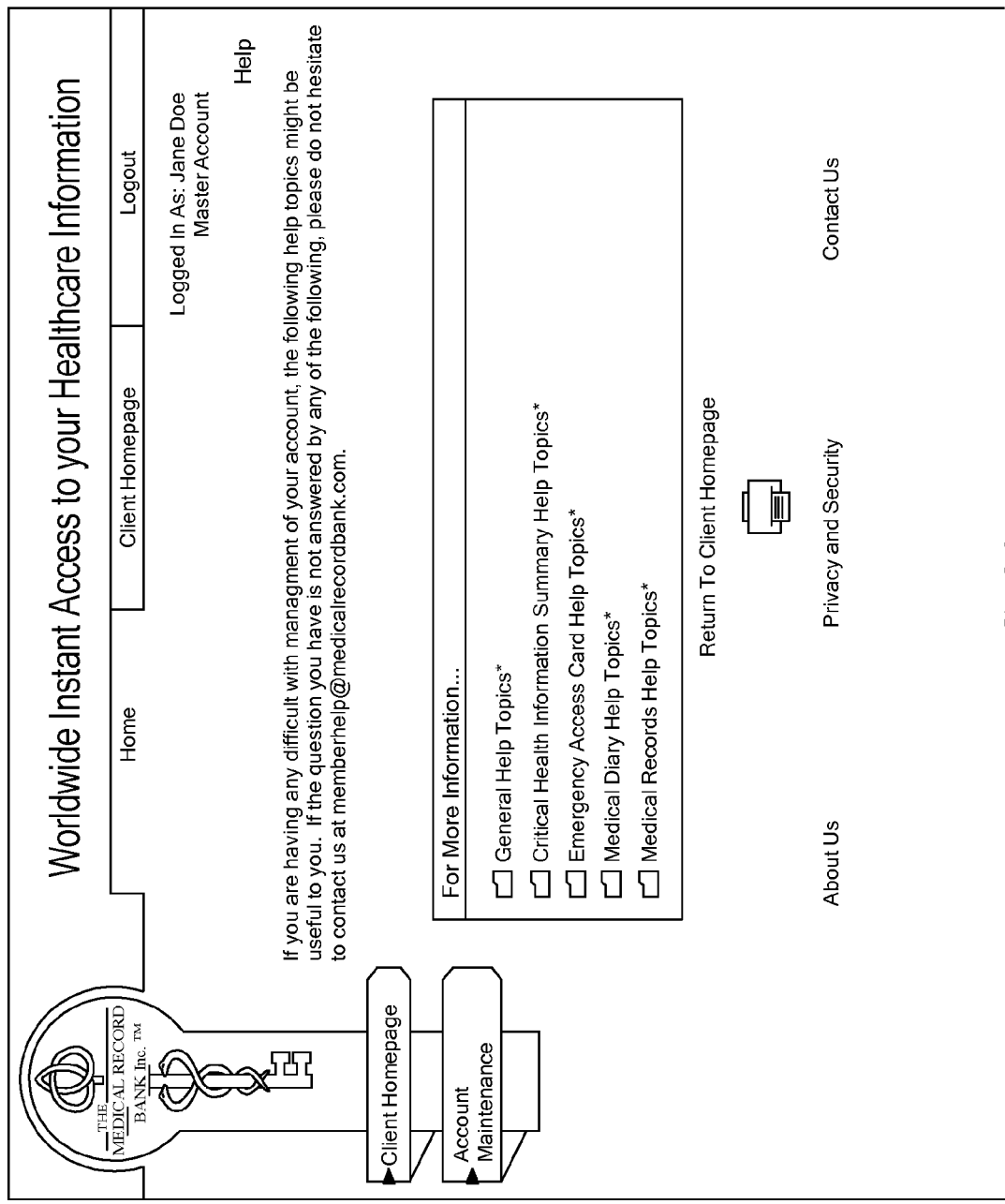
FIG. 92 is an illustration of a web page whereby a client may access help topics in accordance with the embodiment of FIG. 30.

FIG. 91 is an illustration a web page whereby a client may terminate an account in accordance with the embodiment of FIG. 30 and FIG. 92 is an illustration of a web page whereby a client may access help topics in accordance with the embodiment of FIG. 30.

While the invention has been described in connection with specific embodiments thereof, it will be understood that it is capable of further modification. This application is intended to cover any variation, uses, or adaptations of the invention and including such departures from the present disclosure as come within known or customary practice in the art to which invention pertains.

What is claimed is:

1. A method of creating and maintaining a centralized medical record system comprising:
   establishing, in a computer system, a record associated with an account of a client, wherein the client is a patient or a guardian of the patient, the computer system being in communication with a network to which the client has access;
   receiving a copy of at least one medical record or item of data, from one or more of a multiplicity of health care entity sources, sent to the centralized medical record system pursuant to a written request by the client to each of the health care entity sources;
   producing an electronic representation of each copy received from each of the multiplicity of health care entity sources;
   storing, in the centralized medical record system, the representation received and logically associating, with each representation, client information related to the client; and
   providing the client with access, via a web page, to each of the representations over the network, each of the representations constituting an accessible entry in the web page, such that the client can review the representations, wherein the web page includes a facility by which the client can provide information describing each representation, such information being stored in logical association with such representation so as to permit subsequent access to and retrieval thereof via the web page, such information including a client-described label that is used in identifying the representation on the web page.

2. A method according to claim 1, wherein at least one health care entity source is a physician.

3. A method according to claim 1, wherein at least one health care entity source is a clinic.

4. A method according to claim 1, wherein at least one health care entity source is a hospital.

5. A method according to claim 1, wherein providing the client with access to each of the representations over the network includes providing the client with access to the representations via the Internet.

6. A method according to claim 1, further comprising:
   providing the client with access to a letter template for generating a letter to request that the copy of the medical records and items of data be sent from a source.

7. A method according to claim 6, wherein the letter template causes the letter to be imprinted with a machine readable code identifying at least the client.

8. A method according to claim 6, wherein the letter template causes the letter to be imprinted with a machine readable code identifying at least the health care entity source of the medical records or items of data.

9. A method according to claim 1, further comprising:
providing the client with an interface that enables the client to accept or reject the association of the representations with the client.

10. A method according to claim 1, wherein the information includes a date associated with the medical record or item of data.

11. A method according to claim 1, wherein the information includes a name of a health care entity associated with the medical record or item of data.

12. A method according to claim 1, wherein the information includes the client's comments regarding the medical record or item of data.

13. A method according to claim 1, wherein providing the client with access to each of the representations over the network includes providing the client with at least one set of passwords.

14. A method according to claim 13, wherein the client may restrict access provided by one or more of the set of passwords to the representation.

15. A method according to claim 1, wherein providing the client with access to each of the representations includes permitting another party to obtain access to the representation via a password previously forwarded to the client so that the client may grant access to the representation by communicating the password to the other party.

16. A method according to claim 15, wherein the other party has been identified by the client as being in a category of authorized parties.

17. A method according to claim 1, further comprising providing the client with an interface that enables the client to activate one or more emergency cards.

18. A method according to claim 1, further comprising:
providing the client with an interface that allows the client to maintain a medical record diary that the client may enter medical information into on a regular basis, each entry of the medical information being dated and stored in the computer system.

19. A method according to claim 18, wherein the interface includes a place for entry by the patient of a particular illness or condition.

20. A method according to claim 1, wherein the account includes an adult account or a custodial account.

21. A method according to claim 20, further comprising:
transferring the custodial account to a child or ward once the child or ward is no longer under the supervision of a parent or custodian.

22. A method according to claim 1, wherein storing includes
placing the representation in a review folder awaiting review by the client, wherein the representations in the review folder are only accessible to the client and not accessible to authorized parties viewing the centralized medical record system.

23. A method according to claim 22, further comprising:
allowing the client to accept or reject the representation in the review folder;
if the client accepts, moving the representation from the review folder to a medical record folder so that the representations are accessible to authorized parties viewing the centralized medical record system; and
if the client rejects, removing the representation from the centralized medical record system.

24. A method of accessing a patient's medical record or item of data in a centralized medical record system, the method comprising:
storing, in a computer system, copies of medical records and items of data collected from a multiplicity of health care entity sources pursuant to a written request by the patient, the medical records and items of data associated with the patient, the computer system being in communication with a network to which the patient has access;
permitting the patient to provide information describing each copy and storing the information in logical association therewith, such information including a patient-described label that is used in identifying the copy on a graphical user interface; and
accessing the copy via the graphical user interface that displays the stored information.

25. A method according to claim 24, further comprising:
allowing the patient to accept or reject the copy; and
if the patient rejects, removing the copy from the centralized medical record system.

26. A method according to claim 24, wherein the information includes a date associated with the medical record or item data.

27. A method according to claim 24, wherein the information includes a name of a health care entity source associated with the medical record or item data.

28. A method according to claim 24, wherein the information includes the patient's comments regarding the medical record or item data.

* * * * *